(12) United States Patent
Strothmann et al.

(10) Patent No.: US 8,261,742 B2
(45) Date of Patent: Sep. 11, 2012

(54) METHOD AND APPARATUS FOR ADJUSTING DESIRED PRESSURE IN POSITIVE AIRWAY PRESSURE DEVICES

(75) Inventors: Thomas Strothmann, Bramsche (DE); Joseph B. Richey, II, Chagrin Falls, OH (US)

(73) Assignee: Invacare Corporation, Elyria, OH (US)

( * ) Notice: Subject to any disclaimer, the term of this patent is extended or adjusted under 35 U.S.C. 154(b) by 811 days.

(21) Appl. No.: 12/197,692

(22) Filed: Aug. 25, 2008

(65) Prior Publication Data

US 2009/0050154 A1    Feb. 26, 2009

Related U.S. Application Data

(60) Provisional application No. 60/957,499, filed on Aug. 23, 2007.

(51) Int. Cl.
*A61M 16/00* (2006.01)
*A62B 7/00* (2006.01)
*A62B 7/04* (2006.01)
*F16K 31/02* (2006.01)
*F16K 31/26* (2006.01)

(52) U.S. Cl. ............... 128/204.23; 128/204.26

(58) Field of Classification Search ............ 128/204.18, 128/204.22, 204.23, 204.26, 205.11; *A61M 16/00; A62B 7/00, 7/04; F16K 31/02*
See application file for complete search history.

(56) References Cited

U.S. PATENT DOCUMENTS

| | | | |
|---|---|---|---|
| 3,822,698 A | 7/1974 | Guy | |
| 3,921,628 A | 11/1975 | Smythe et al. | |
| 4,011,859 A | 3/1977 | Frankenberger | |
| 4,121,578 A | 10/1978 | Torzala | |
| 4,350,166 A | 9/1982 | Mobarry | |
| 4,506,678 A | 3/1985 | Russell et al. | |
| 4,590,951 A | 5/1986 | O'Connor | |
| 4,648,396 A | 3/1987 | Raemer | |
| 4,651,729 A | 3/1987 | Rae | |
| 4,655,213 A | 4/1987 | Rapoport et al. | |

(Continued)

FOREIGN PATENT DOCUMENTS

EP    164946    12/1985

(Continued)

OTHER PUBLICATIONS

International Search Report from PCT/US01/30768 dated May 31, 2002.

(Continued)

*Primary Examiner* — Oren Ginsberg
(74) *Attorney, Agent, or Firm* — Calfee, Halter & Griswold LLP

(57) ABSTRACT

Systems and methods for adjusting a desired pressure in a positive airway pressure (PAP) device are provided. In one embodiment, the method includes: a) providing breathing gas under positive pressure to a patient via a PAP device based on current desired pressure, b) monitoring a characteristic of the breathing gas, patient, or PAP device indicative of respiration, c) creating a breathing cycle signal having a first level associated with inhalation and a second level associated with exhalation, the signal being based on the monitored respiration characteristic, d) performing an abnormal breathing check based on the monitored respiration characteristic and the breathing cycle signal, and e) if abnormal breathing is detected, increasing the current desired pressure until a maximum desired pressure is reached, otherwise, decreasing the current desired pressure until a minimum desired pressure is reached. Several embodiments of an apparatus associated with the method are also provided.

43 Claims, 50 Drawing Sheets

U.S. PATENT DOCUMENTS

| | | |
|---|---|---|
| 4,713,558 A | 12/1987 | Russell et al. |
| 4,728,499 A | 3/1988 | Fehder |
| 4,773,411 A | 9/1988 | Downs |
| 4,817,013 A | 3/1989 | Corenman et al. |
| 4,821,736 A | 4/1989 | Watson |
| 4,944,310 A | 7/1990 | Sullivan |
| 4,994,117 A | 2/1991 | Fehder |
| 5,044,362 A | 9/1991 | Younes |
| 5,065,756 A | 11/1991 | Rapoport |
| 5,094,235 A | 3/1992 | Westenskow et al. |
| 5,117,819 A | 6/1992 | Servidio et al. |
| 5,124,129 A | 6/1992 | Riccitelli et al. |
| 5,134,995 A | 8/1992 | Gruenke et al. |
| 5,148,802 A | 9/1992 | Sanders et al. |
| 5,166,075 A | 11/1992 | Fehder |
| 5,179,002 A | 1/1993 | Fehder |
| 5,193,544 A | 3/1993 | Jaffe |
| 5,199,424 A | 4/1993 | Sullivan et al. |
| 5,203,343 A | 4/1993 | Axe et al. |
| 5,239,995 A | 8/1993 | Estes et al. |
| 5,245,995 A | 9/1993 | Sullivan et al. |
| 5,251,632 A | 10/1993 | Delpy |
| 5,279,289 A | 1/1994 | Kirk |
| 5,303,701 A | 4/1994 | Heins et al. |
| 5,313,937 A | 5/1994 | Zdrojkowski |
| 5,332,901 A | 7/1994 | Eckles et al. |
| 5,335,650 A | 8/1994 | Shaffer et al. |
| 5,335,654 A | 8/1994 | Rapoport |
| 5,343,878 A | 9/1994 | Scarberry et al. |
| 5,353,788 A | 10/1994 | Miles |
| 5,372,130 A | 12/1994 | Stern et al. |
| 5,394,882 A | 3/1995 | Mawhinney |
| 5,433,193 A | 7/1995 | Sanders et al. |
| 5,438,980 A | 8/1995 | Phillips |
| 5,445,160 A | 8/1995 | Culver et al. |
| 5,456,249 A | 10/1995 | Kirk |
| 5,458,137 A | 10/1995 | Axe et al. |
| 5,490,502 A | 2/1996 | Rapoport et al. |
| 5,492,113 A | 2/1996 | Estes et al. |
| 5,503,146 A | 4/1996 | Froehlich et al. |
| 5,522,382 A | 6/1996 | Sullivan et al. |
| RE35,295 E | 7/1996 | Estes et al. |
| 5,535,738 A | 7/1996 | Estes et al. |
| 5,535,739 A | 7/1996 | Rapoport et al. |
| 5,537,997 A | 7/1996 | Mechlenburg et al. |
| 5,538,000 A | 7/1996 | Rudolph |
| 5,540,219 A | 7/1996 | Mechlenburg et al. |
| 5,546,933 A | 8/1996 | Rapoport et al. |
| 5,549,106 A | 8/1996 | Gruenke et al. |
| 5,551,418 A | 9/1996 | Estes et al. |
| 5,551,419 A | 9/1996 | Froehlich et al. |
| 5,558,638 A | 9/1996 | Evers et al. |
| RE35,339 E | 10/1996 | Rapoport |
| 5,592,938 A | 1/1997 | Scarberry et al. |
| 5,598,838 A | 2/1997 | Servidio et al. |
| 5,630,411 A | 5/1997 | Holscher |
| 5,632,269 A | 5/1997 | Zdrojkowski |
| 5,645,054 A | 7/1997 | Cotner et al. |
| 5,655,522 A | 8/1997 | Mechlenburg et al. |
| 5,679,884 A | 10/1997 | Kirk |
| 5,682,878 A | 11/1997 | Ogden |
| 5,694,923 A | 12/1997 | Hete et al. |
| 5,701,883 A | 12/1997 | Hete et al. |
| 5,704,345 A | 1/1998 | Berthon-Jones |
| 5,715,812 A | 2/1998 | Deighan et al. |
| 5,738,106 A | 4/1998 | Yamamori et al. |
| 5,740,795 A | 4/1998 | Brydon |
| 5,765,563 A | 6/1998 | Vander Schaaf |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,845,636 A | 12/1998 | Gruenke et al. |
| 5,865,173 A | 2/1999 | Froehlich |
| 5,881,717 A | 3/1999 | Isaza |
| 5,881,723 A | 3/1999 | Wallace et al. |
| 5,901,704 A | 5/1999 | Estes et al. |
| 5,904,141 A | 5/1999 | Estes et al. |
| 5,915,379 A | 6/1999 | Wallace et al. |
| 5,915,380 A | 6/1999 | Wallace et al. |
| 5,927,274 A | 7/1999 | Servidio et al. |
| 5,937,851 A | 8/1999 | Serowski et al. |
| 5,947,115 A | 9/1999 | Lordo et al. |
| 5,953,713 A | 9/1999 | Estes et al. |
| 5,954,050 A | 9/1999 | Christopher |
| 5,970,975 A | 10/1999 | Estes et al. |
| 6,017,315 A | 1/2000 | Starr et al. |
| 6,024,089 A | 2/2000 | Wallace et al. |
| 6,026,312 A | 2/2000 | Shemwell et al. |
| 6,029,660 A | 2/2000 | Calluaud et al. |
| 6,029,664 A | 2/2000 | Zdrojkowski et al. |
| 6,029,665 A | 2/2000 | Berthon-Jones |
| 6,044,843 A | 4/2000 | O'Neil et al. |
| 6,071,237 A | 6/2000 | Weil et al. |
| 6,085,747 A | 7/2000 | Axe et al. |
| 6,091,973 A | 7/2000 | Colla et al. |
| 6,095,974 A | 8/2000 | Shemwell et al. |
| 6,099,481 A | 8/2000 | Daniels et al. |
| 6,102,042 A | 8/2000 | Hete et al. |
| 6,105,575 A | 8/2000 | Estes et al. |
| 6,123,074 A | 9/2000 | Hete et al. |
| 6,123,075 A | 9/2000 | Kirk et al. |
| 6,135,106 A | 10/2000 | Dirks et al. |
| 6,138,675 A | 10/2000 | Berthon-Jones |
| 6,142,952 A | 11/2000 | Behbehani et al. |
| 6,152,129 A | 11/2000 | Berthon-Jones |
| 6,155,257 A | 12/2000 | Lurie et al. |
| 6,155,986 A | 12/2000 | Brydon et al. |
| 6,182,657 B1 | 2/2001 | Brydon et al. |
| 6,183,423 B1 | 2/2001 | Gaumond et al. |
| 6,212,435 B1 | 4/2001 | Lattner et al. |
| 6,213,119 B1 | 4/2001 | Brydon et al. |
| 6,237,592 B1 | 5/2001 | Surjadi et al. |
| 6,237,593 B1 | 5/2001 | Brydon |
| 6,240,921 B1 | 6/2001 | Brydon et al. |
| 6,253,764 B1 | 7/2001 | Calluaud |
| 6,257,234 B1 | 7/2001 | Sun |
| 6,269,811 B1 | 8/2001 | Duff et al. |
| 6,269,812 B1 | 8/2001 | Wallace et al. |
| 6,279,569 B1 | 8/2001 | Berthon-Jones |
| 6,286,508 B1 | 9/2001 | Remmers et al. |
| 6,299,581 B1 | 10/2001 | Rapoport et al. |
| 6,305,105 B1 | 10/2001 | Wickham et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,347,631 B1 | 2/2002 | Hansen et al. |
| 6,349,724 B1 | 2/2002 | Burton et al. |
| 6,357,463 B1 | 3/2002 | Wickham et al. |
| 6,367,474 B1 | 4/2002 | Berthon-Jones et al. |
| 6,401,713 B1 | 6/2002 | Hill et al. |
| 6,435,184 B1 | 8/2002 | Ho |
| 6,443,154 B1 | 9/2002 | Jalde et al. |
| 6,467,477 B1 | 10/2002 | Frank et al. |
| 6,516,802 B2 | 2/2003 | Hansen et al. |
| 6,609,517 B1 | 8/2003 | Estes et al. |
| 6,636,021 B2 | 10/2003 | Schenkel et al. |
| 6,745,770 B2 | 6/2004 | McAuliffe et al. |
| 6,752,151 B2 | 6/2004 | Hill |
| 6,766,800 B2 | 7/2004 | Chu et al. |
| 6,796,305 B1 | 9/2004 | Banner et al. |
| 6,817,361 B2 | 11/2004 | Berthon-Jones et al. |
| 6,823,866 B2 | 11/2004 | Jafari et al. |
| 6,834,646 B2 | 12/2004 | Alon et al. |
| 6,866,040 B1 | 3/2005 | Bourdon |
| 6,895,964 B2 | 5/2005 | McAuliffe et al. |
| 6,932,084 B2 | 8/2005 | Estes et al. |
| 6,968,842 B1 | 11/2005 | Truschel et al. |
| 6,990,980 B2 | 1/2006 | Richey, II |
| 7,028,688 B1 | 4/2006 | Grove et al. |
| 7,066,173 B2 | 6/2006 | Banner et al. |
| 7,089,936 B2 | 8/2006 | Madaus et al. |
| 7,152,598 B2 | 12/2006 | Morris et al. |
| 7,168,429 B2 | 1/2007 | Matthews et al. |
| 7,621,270 B2 | 11/2009 | Morris et al. |
| 8,066,004 B2 | 11/2011 | Morris et al. |

| | | |
|---|---|---|
| 2001/0004894 A1 | 6/2001 | Bourdon |
| 2001/0015204 A1 | 8/2001 | Hansen et al. |
| 2001/0027791 A1 | 10/2001 | Wallace et al. |
| 2001/0027792 A1 | 10/2001 | Berthon-Jones et al. |
| 2001/0035186 A1 | 11/2001 | Hill |
| 2001/0035187 A1 | 11/2001 | Smith et al. |
| 2002/0104536 A1 | 8/2002 | Richey, II |
| 2003/0159695 A1 | 8/2003 | Younes |
| 2004/0035422 A1 | 2/2004 | Truitt et al. |
| 2004/0103896 A1 | 6/2004 | Jafari et al. |
| 2004/0107953 A1 | 6/2004 | Hegge et al. |
| 2004/0123866 A1 | 7/2004 | Berthon-Jones |
| 2004/0187870 A1 | 9/2004 | Matthews et al. |
| 2004/0255943 A1 | 12/2004 | Morris |
| 2005/0016536 A1 | 1/2005 | Rapoport et al. |
| 2005/0020932 A1 | 1/2005 | Haberland et al. |
| 2005/0034724 A1 | 2/2005 | O'Dea |
| 2005/0080461 A1 | 4/2005 | Stahmann et al. |
| 2005/0166922 A1 | 8/2005 | Knepper |
| 2005/0224078 A1 | 10/2005 | Zdrojkowski et al. |
| 2005/0241639 A1 | 11/2005 | Zilberg |
| 2005/0247310 A1 | 11/2005 | Grove et al. |
| 2005/0268913 A1 | 12/2005 | Morris |
| 2005/0279358 A1 | 12/2005 | Richey |
| 2006/0000475 A1 | 1/2006 | Matthews et al. |
| 2006/0011200 A1 | 1/2006 | Remmers et al. |
| 2006/0162728 A1 | 7/2006 | Delache et al. |
| 2006/0174889 A1 | 8/2006 | Noble |
| 2006/0180149 A1* | 8/2006 | Matarasso ............... 128/204.18 |
| 2007/0000494 A1 | 1/2007 | Banner et al. |
| 2007/0016093 A1 | 1/2007 | Rapoport et al. |
| 2007/0028921 A1 | 2/2007 | Banner et al. |
| 2007/0051371 A1 | 3/2007 | Sullivan et al. |
| 2007/0167843 A1 | 7/2007 | Cho et al. |
| 2008/0060647 A1 | 3/2008 | Messenger et al. |
| 2008/0251079 A1 | 10/2008 | Richey |

FOREIGN PATENT DOCUMENTS

| | | |
|---|---|---|
| EP | 0 722 747 | 7/1996 |
| JP | 7-096035 | 4/1995 |
| JP | 10-505765 | 6/1998 |
| JP | 3090468 | 7/2000 |
| JP | 2001-000547 | 1/2001 |
| WO | 90/14121 | 11/1990 |
| WO | 02/26283 | 4/2002 |
| WO | 02/26287 | 4/2002 |
| WO | 2005/004780 | 1/2005 |
| WO | 2005/028009 | 3/2005 |
| WO | 2005/063323 | 7/2005 |
| WO | 2006/009939 | 1/2006 |
| WO | 2008/127986 | 10/2008 |

OTHER PUBLICATIONS

Written Opinion from PCT/US01/30768 dated Dec. 12, 2002.
International Preliminary Examination Report from PCT/US01/30768 dated Apr. 15, 2003.
International Search Report and Written Opinion from PCT/US04/007170 dated Jan. 27, 2005.
Office action from U.S. Appl. No. 11/519,532 dated Jul. 1, 2010.
Declaration of Non-Establishment of International Search Report and Written Opinion from PCT/US05/21638 dated Sep. 23, 2005.
International Search Report from PCT/US08/59915 dated Sep. 17, 2008.
Written Opinion from PCT/US08/59915 dated Sep. 17, 2008.
Response from Chinese Application No. 200580028591.2 dated Jun. 16, 2010.
Office action from U.S. Appl. No. 09/967,274 dated Apr. 23, 2003.
Response from U.S. Appl. No. 09/967,274 dated Sep. 23, 2003.
Office action from U.S. Appl. No. 09/967,274 dated Jan. 14, 2004.
Response from U.S. Appl. No. 09/967,274 dated Apr. 13, 2004.
Office action from U.S. Appl. No. 09/967,274 dated Jul. 27, 2004.
Response from U.S. Appl. No. 09/967,274 dated Oct. 27, 2004.
Office action from U.S. Appl. No. 09/967,274 dated Jan. 25, 2005.
Response from U.S. Appl. No. 09/967,274 dated May 23, 2005.
Notice of Allowance from U.S. Appl. No. 09/967,274 dated Jul. 11, 2005.
Office action from U.S. Appl. No. 10/601,720 dated Jan. 6, 2005.
Response from U.S. Appl. No. 10/601,720 dated Mar. 28, 2005.
Office action from U.S. Appl. No. 10/601,720 dated Jun. 21, 2005.
Response from U.S. Appl. No. 10/601,720 dated Nov. 21, 2005.
Office action from U.S. Appl. No. 10/601,720 dated Feb. 7, 2006.
Response from U.S. Appl. No. 10/601,720 dated Jun. 7, 2006.
Notice of Allowance from U.S. Appl. No. 10/601,720 dated Aug. 8, 2006.
Office action from U.S. Appl. No. 11/157,089 dated Feb. 23, 2009.
Response from U.S. Appl. No. 11/157,089 dated May 26, 2009.
Notice of Allowance from U.S. Appl. No. 11/157,089 dated Jul. 15, 2009.
Supplemental Notice of Allowance from U.S. Appl. No. 11/157,089 dated Aug. 24, 2009.
Office action from U.S. Appl. No. 11/206,410 dated May 28, 2008.
Response from U.S. Appl. No. 11/206,410 dated Aug. 28, 2008.
Office action from U.S. Appl. No. 11/206,410 dated Feb. 6, 2009.
Response from U.S. Appl. No. 11/206,410 dated Jun. 8, 2009.
Office action from U.S. Appl. No. 11/206,410 dated Oct. 8, 2009.
Response from U.S. Appl. No. 11/206,410 dated Jan. 27, 2010.
Office action from U.S. Appl. No. 11/519,532 dated Nov. 16, 2009.
Response from U.S. Appl. No. 11/519,532 dated Apr. 6, 2010.
Office action from Chinese application No. 200580028591.2 dated Feb. 6, 2009.
Office action from Chinese application No. 200580028591.2 dated Jul. 24, 2009.
Office action from Chinese application No. 200580028591.2 dated Apr. 28, 2010.
Office action from U.S. Appl. No. 11/206,410 dated Jun. 25, 2010.
Office action from U.S. Appl. No. 11/206,410 dated Jan. 6, 2011.
International Search Report mailed on Dec. 3, 2008, for International Application No. PCT/US2008/074194.
Written Opinion mailed on Dec. 3, 2008, for International Application No. PCT/US2008/074194.
Lankford, Got Compliance?, ResMed Power Point presentation, 34 pgs.
Portier et al., Evaluation of Home versus Laboratory Polysomnography in the Diagnosis of Sleep Apnea Syndrome Am J Respir Crit Care Med. vol. 162, pp. 814-818, 2000.
Response from U.S. Appl. No. 11/206,410 dated Oct. 22, 2010.
Response from U.S. Appl. No. 11/519,532 dated Dec. 1, 2010.
Office action from Japanese Application No. 2007-516811 dated Sep. 29, 2010.
Office action from Chinese application No. 200580028591.2 dated Jan. 8, 2010.
Response from Chinese application No. 200580028591.2 dated Jun. 19, 2009.
Response from Chinese application No. 200580028591.2 dated Dec. 7, 2009.
Communication from EP Application No. 01973647.9 dated Aug. 13, 2009.
Response to EP Communication from Application No. 01973647.9 dated Dec. 2, 2009.
Communication from EP Application No. 04719190.3 dated Apr. 7, 2009.
Response to EP Communication from Application No. 04719190.3 dated Jun. 16, 2009.
Communication from EP Applciation No. 04719190.3 dated Nov. 12, 2009.
Communication from EP Application No. 05766008.6 dated Nov. 5, 2009.
Response to EP Communication from Application No. 05766008.6 dated Mar. 8, 2010.
Belozeroff et al., "Effects of CPAP therapy on cardiovascular variability in obstructive sleep apnea: a closed-loop analysis", Am J Physiol—Heart Circ Physiol, vol. 282, pp. H110-H121, Jan. 2002.
Bliss et al., "Performance of Auto-Titrating CPAP Devices in a Simulation of Varied Patient Breathing", AARC International Congress, San Antonio, TX, 6 pgs., Dec. 2001.
Cairo et al., "Mosby's Respiratory Care Equipment", Chapter 14—Sleep Diagnostics, pp. 682-698, 7th ed., Jul. 31, 2003.

Farre et al., "Response of Automatic Continuous Positive Airway Pressure Devices to Different Sleep Breathing Patterns—A Bench Study", Am. J. Respir. Crit Care Med, vol. 166, pp. 469-473, 2002.
Heitman et al. "Validation of nasal pressure for the identification of apneas/hypopneas during sleep", Am J Respir Crit Care Med, vol. 166, pp. 386-391, 2002.
Invacare Corp., Owner's Manual, Polaris/Polaris LT Nasal CPAP System, 20 pgs. Copyright 2002, Ref F, Jul. 2002.
Leung et al., Sleep Apnea and Cardiovascular Disease, Am J Respir Crit Care Med, vol. 164, pp. 2147-2165, 2001.
Liesching et al., "Evaluation of the Accuracy of SNAP Technology Sleep Sonography in Detecting Obstructive Sleep Apnea in Adults Compared to Standard Polysomnography, Chest—The Cardiopulmonary and Critical Care Journal", vol. 125, No. 3, pp. 886-891, Mar. 2004.
Mallinckrodt, Inc., Breath free to breeze and DreamSeal, Puritan-Bennett SleepGear, MS-AC/Breeze/GB, 6 pgs. Copyright 2000.
Nellcor Puritan Bennett, Inc., Breeze SleepGear and DreamSeal Assembly Coding Matrix, A.d. 0426v2-0304, ST03700, 2 pgs. Copyright 2004.
Nellcor Puritan Bennett, Inc., Breeze SleepGear Users Guide, pp. 3, 4, 6 and 13, copyright 2004.
Nellcor Puritan Bennett, Inc., Dreamfit Nasal Mask, www.puritanbennett.com/prod/Product.aspx?S1=SPT&S2=CPI&id=284, 2 pgs. Printed Oct. 2, 2006, copyright 2006.
Penzel et al., "Systemic comparison of different algorithms for apnea detection based on electrocardiogram recordsings", Medical & Biological Engineering & Computing, vol. 40, pp. 402-407 (2002).
Portier et al., Evaluation of Home versus Laboratory Polysomnography in the Diagnosis of Sleep Apnea Syndrome ' Am J Respir Crit Care Med. vol. 162, pp. 814-818, 2000.
Researchers create DNA-based nanosensors, Small Times Magazine, 1 pg, Stp. 16, 2005.
ResMed, S8 AutoSet Vantage—AutoSet Technology, resmed.com/portal/site/ResMedUS/?vgnCld=9ec827e4bd475010vbnVCMServerc6..., printed on Jun. 24, 2006, 3 pgs., copyright 2000-2006, last updated Sep. 12, 2005.
Ryan et al., Periodicity of Obstructive Sleep Apnea in Patients with and without heart failure, Chest Journal, vol. 127, No. 2, pp. 536-542, Feb. 2005.
Tamisier et al., "Expiratory Changes in Pressure: Flow Ratio During Sleep in Patients with Sleep-disordered breathing", Sleep, vol. 27, No. 2, pp. 240-248, 2004.
Tyco Healthcare UK Ltd., Breeze Sleep Gear CPAP Interface System, A.b. 1751-0504, ST00900, 2 pgs. Copyright 2004.
Tyco Healthcare UK Ltd., Breeze SleepGear CPAP Interface System, C-AD-Breeze/GB, 4 pgs., copyright 2004, Jul. 2004.
Tyco Healthcare UK Ltd., New Easy-to-Fit CPAP Interface [dreamfit nasalmask], A.ae 2175v2-0905, ST06604, 2 pgs., copyright 2005, Sep. 2005.
Response from Chinese application No. 200580028591.2 dated Mar. 19, 2010.
Response to EP Communication for Application No. 04719190.3 dated May 12, 2010.
Response from U.S. Appl. No. 11/206,410 dated Apr. 8, 2011.
Office action from U.S. Appl. No. 11/206,410 dated Jun. 29, 2011.
Office action from U.S. Appl. No. 11/519,532 dated Mar. 7, 2011.
Response from U.S. Appl. No. 11/519,532 dated Aug. 5, 2011.
Office action from EP Application No. 04719190-3 dated Jan. 4, 2011.
Response from EP Application No. 04719190-3 dated May 13, 2011.
Mosbacker, "Circulatory System", pp. 1-3, Art Today, Utah Education Network, www.uen.org/utahlink/activities/view_activity.cgi?activity_id=3043 printed Feb. 24, 2011.
Office action from U.S. Appl. No. 11/519,532 dated Oct. 11, 2011.
Issue Notification from U.S. Appl. No. 12/623,994 dated Nov. 29, 2011.
Office action from Canadian application No. 2,530,523 dated Dec. 1, 2011.
Office action from Chinese application No. 201010522527.2 dated Oct. 19, 2011.
Office action from EP Application No. 04719190-3 dated Nov. 4, 2011.
Exam Report from EP Application No. 05766008.6 dated Oct. 17, 2011.
Notice of Allowance from U.S. Appl. No. 12/623,994 dated Sep. 22, 2011.
Response from U.S. Appl. No. 11/206,410 dated Oct. 28, 2011.
Lankford, D. Alan, Got Compliance?, ResMed Power Point presentation, 34 pgs. (at least as early as Oct. 2005).
First Office Action from Chinese Application No. 200880020253.8 dated Jan. 18, 2012.
Response to First Office Action from Chinese Application No. 201010522527.2 dated Feb. 10, 2012.
Office action from Chinese application No. 201010522527.2 dated Feb. 20, 2012.
Response to Office Action from Chinese application No. 201010522527.5 dated Feb. 27, 2012.
Response to EP Communication No. 05766008.6 dated Mar. 16, 2012.

* cited by examiner

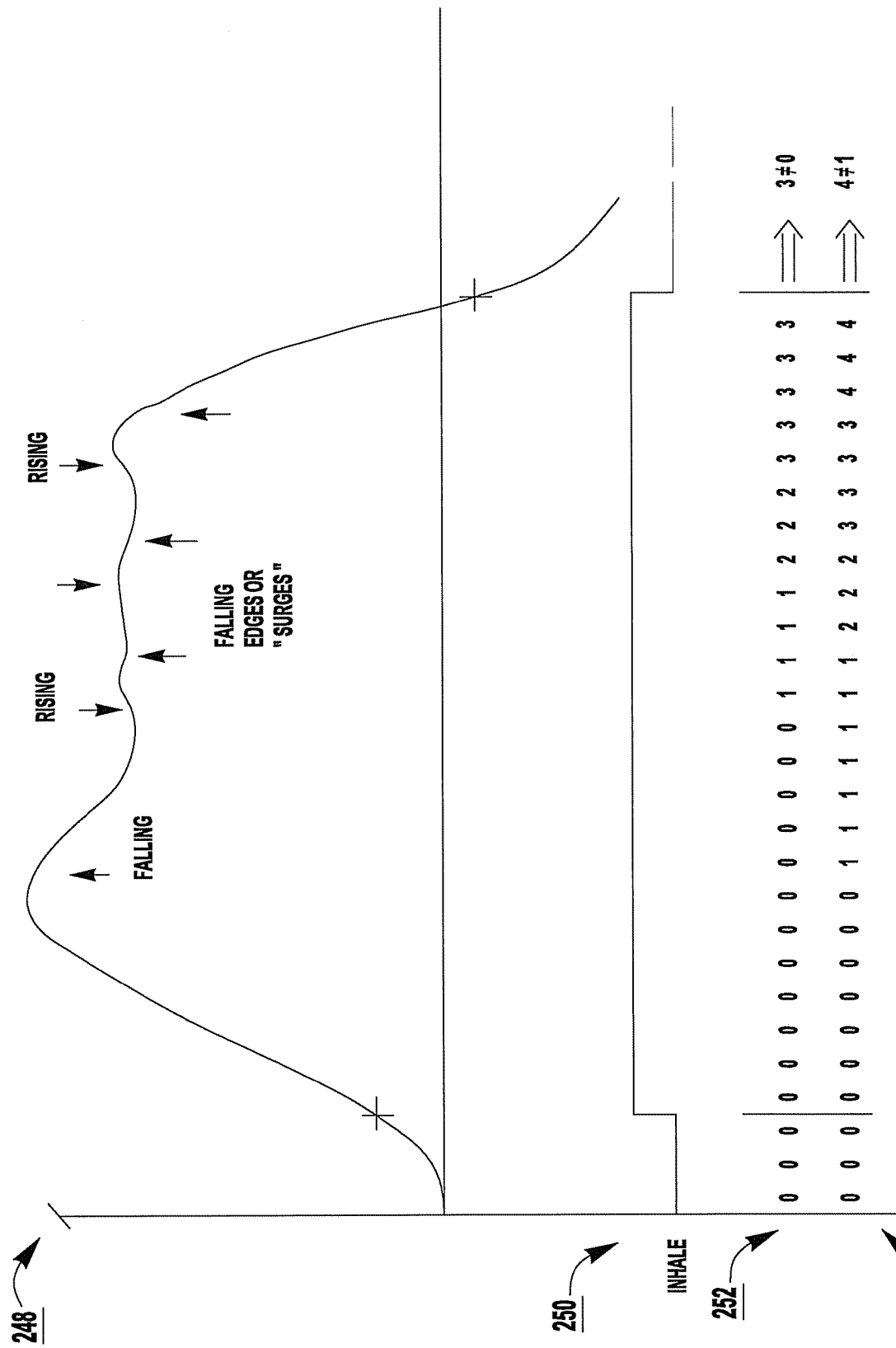

METHOD AND APPARATUS FOR ADJUSTING DESIRED PRESSURE IN POSITIVE AIRWAY PRESSURE DEVICES

CROSS-REFERENCE TO RELATED APPLICATIONS

This application claims priority to, and any other benefit of, U.S. Provisional Patent Application Nos. 60/957,499, filed Aug. 23, 2007, the contents of which are fully incorporated herein by reference. This case is also related to a corresponding PCT case, Int'l Application No. PCT/US2008/074164, filed Aug. 25, 2008 and entitled METHOD AND APPARATUS FOR ADJUSTING DESIRED PRESSURE IN POSITIVE AIRWAY PRESSURE DEVICES, the contents of which are fully incorporated herein by reference.

BACKGROUND

Abnormal breathing may be treated by applying a breathing gas under positive pressure to a patient's airway via a positive airway pressure (PAP) device. This positive pressure may effectively "splint" the airway, thereby maintaining an open passage to the lungs. The pressure of the breathing gas delivered to the patient may be desired to be kept relatively constant at a desired or prescribed pressure during positive pressure therapy. This therapy technique is commonly referred to as continuous positive airway pressure (CPAP). CPAP therapy may be provided using either open-loop or closed-loop control. CPAP therapy may be provided at a constant or continuously positive target pressure using a control unit that controls breathing gas pressure based on the fixed target pressure. Alternatively, the CPAP therapy may also be controlled using a softened exhalation target pressure (SoftX™). SoftX™ is a trademark of Invacare Corporation. In SoftX™, the breathing gas is delivered at a relatively constant pressure, like CPAP, and during an initial portion of exhalation, the pressure set point is reduced, but then increases toward the constant pressure during the latter portion of exhalation, to help maintain the positive airway pressure.

In another type of positive pressure therapy, the pressure of the breathing gas delivered to the patient may be varied with the patient's breathing cycle or varied with the patient's effort such that the pressure during exhalation is less than the pressure during inhalation. This therapy technique may increase comfort to the patient during the therapy and is commonly referred to as bi-level positive airway pressure (BiPAP). In another type of positive pressure therapy, the pressure of the breathing gas delivered to the patient is varied in proportion to the flow generated by the patient. This therapy technique is commonly referred to as proportional positive airway pressure (PPAP).

Any of the various types of PAP devices may also incorporate ramping of the positive pressure from a lower pressure level to a higher desired or prescribed pressure level over an extended period (e.g., 10-15 minutes). This ramping process is intended to reduce the airway pressure while the patient is awake and for a period during which the patient may be expected to fall asleep. The positive airway pressure reaches the desired or prescribed level as the ramping period expires.

SUMMARY

In one aspect a method for adjusting a desired pressure in a positive airway pressure device may be provided. In one embodiment, the method may include: a) providing a breathing gas under positive pressure to a patient via a positive airway pressure device based at least in part on a current desired pressure, b) monitoring a characteristic of the breathing gas that may be indicative of respiration, c) creating a breathing cycle signal with a first level associated with inhalation and a second level different from the first level and associated with exhalation, the breathing cycle signal being based at least in part on the monitored respiration characteristic, d) performing one or more abnormal breathing checks based at least in part on the monitored respiration characteristic and the breathing cycle signal, and e) if abnormal breathing is detected, increasing the current desired pressure by a first increment until a maximum desired pressure is reached, otherwise, decreasing the current desired pressure by a second increment until a minimum desired pressure is reached.

In another embodiment, the method may include: a) providing a breathing gas under positive pressure to a patient via a positive airway pressure device based at least in part on a current desired pressure, b) monitoring a characteristic of the breathing gas, a characteristic of the patient, or a characteristic of the positive airway pressure device that may be indicative of respiration, c) creating a breathing cycle signal having a first level associated with inhalation and a second level different from the first level and associated with exhalation, the breathing cycle signal being based at least in part on the monitored respiration characteristic, d) performing an abnormal breathing check based at least in part on the monitored respiration characteristic and the breathing cycle signal, and e) if abnormal breathing is detected, increasing the current desired pressure by a first increment until a maximum desired pressure is reached, otherwise, decreasing the current desired pressure by a second increment until a minimum desired pressure is reached.

In another aspect, an apparatus for adjusting a desired pressure in a positive airway pressure device may be provided. In one embodiment, the apparatus may include: a breathing gas flow path in operative communication with a closed loop control logic, the breathing gas flow path and closed loop control logic being adapted to provide a breathing gas under positive pressure to a patient based at least in part on a current desired pressure, a respiration characteristic monitoring logic in operative communication with the breathing gas flow path to monitor a characteristic of the breathing gas, a characteristic of the patient, or a characteristic of the apparatus that may be indicative of respiration, a breathing cycle signal logic in operative communication with the respiration characteristic monitoring logic to create a breathing cycle signal having a first level associated with inhalation and a second level different from the first level and associated with exhalation, the breathing cycle signal being based at least in part on the monitored respiration characteristic, an abnormal breathing check logic in operative communication with at least one of the breathing cycle signal logic and the respiration characteristic monitoring logic to perform an abnormal breathing check based at least in part on the monitored respiration characteristic and the breathing cycle signal, and a desired pressure adjustment logic in operative communication with the abnormal breathing check logic, breathing cycle signal logic, and closed loop control logic to increase the current desired pressure by a first increment until a maximum desired pressure is reached, if abnormal breathing is detected and to decrease the current desired pressure by a second increment until a minimum desired pressure is reached if abnormal breathing is not detected.

DRAWINGS

Exemplary features, aspects, and advantages of the present invention will become better understood with regard to the accompanying drawings, the following description, and appended claims.

Figure 4A:
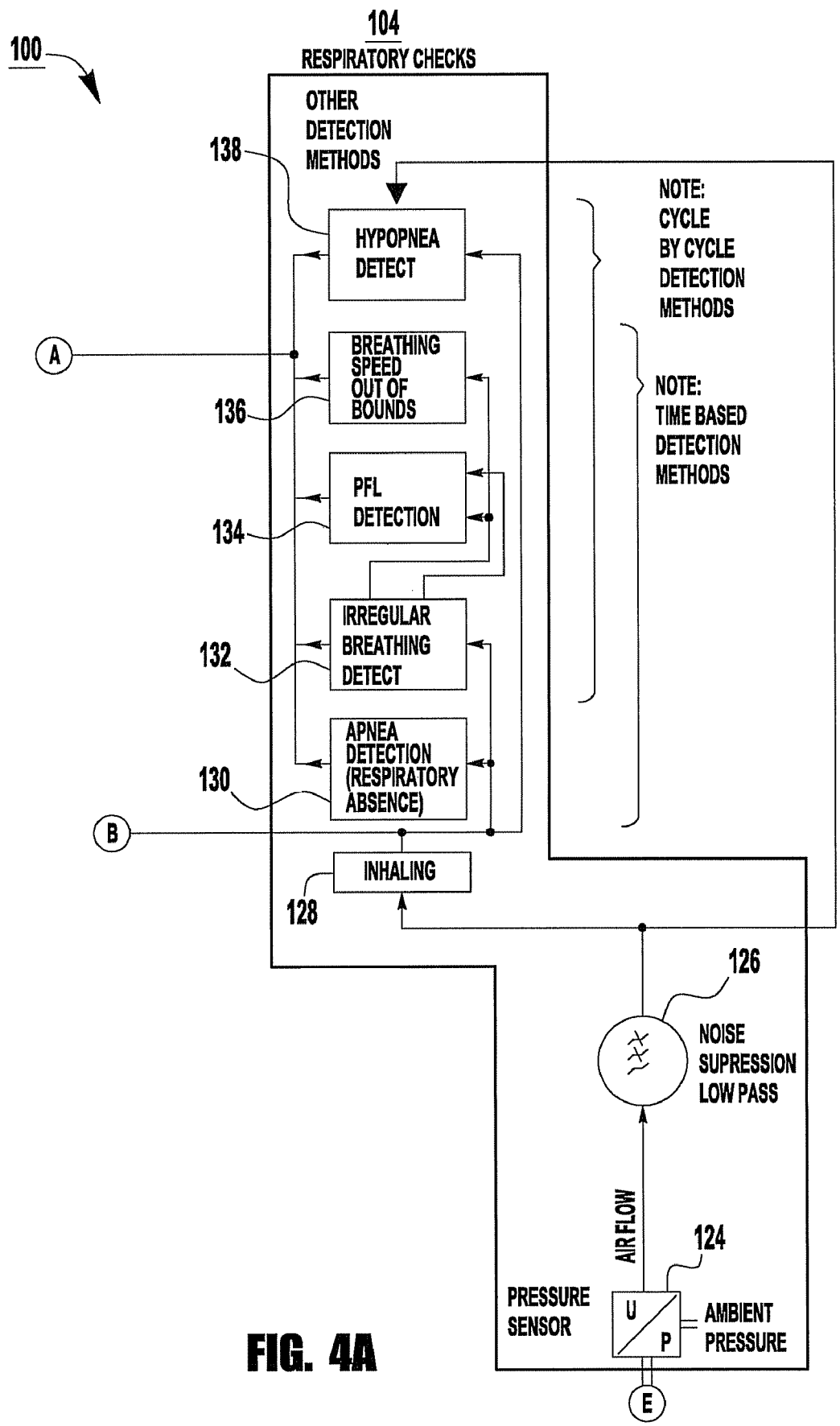
Figure 4B:
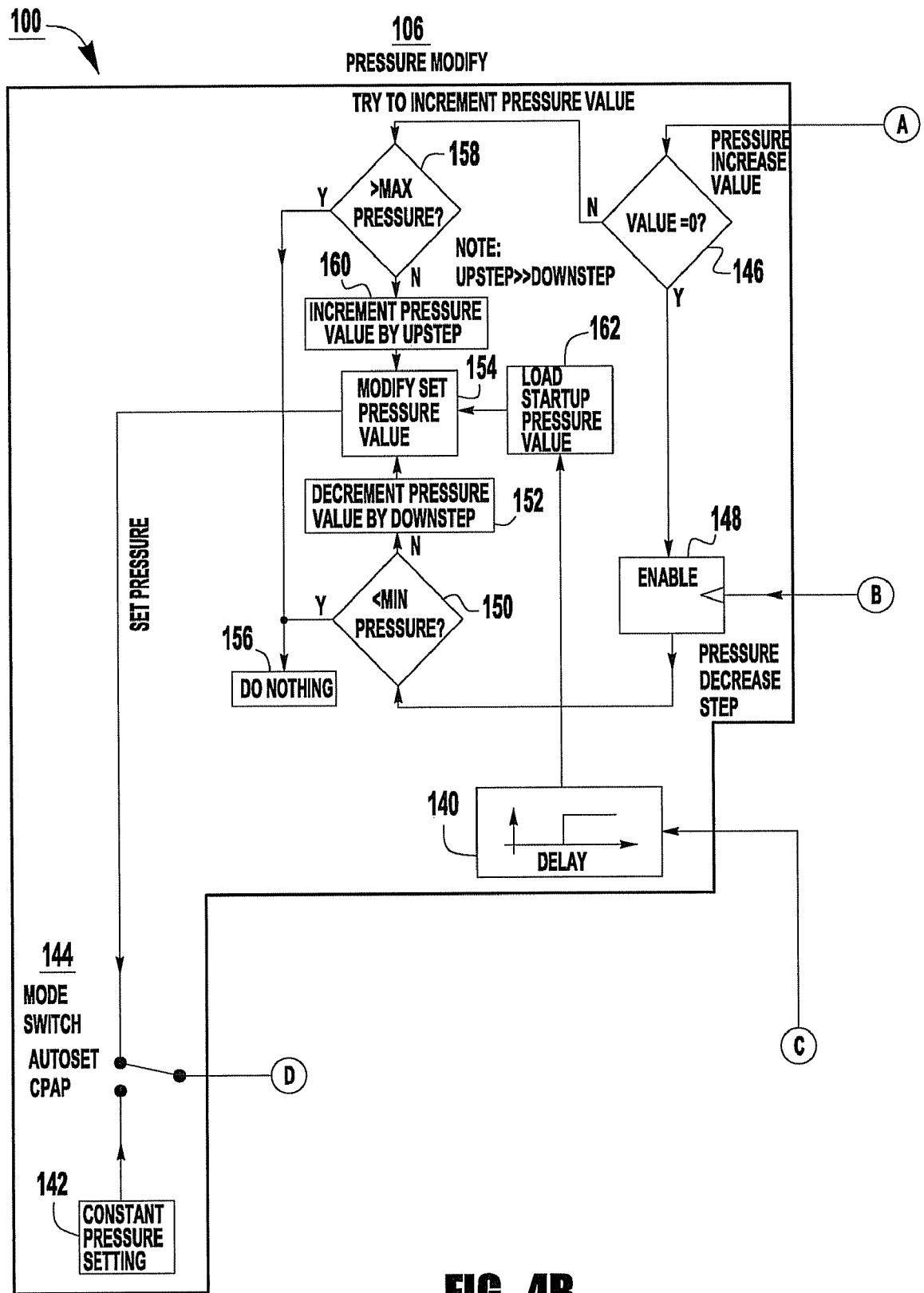
Figure 4C:
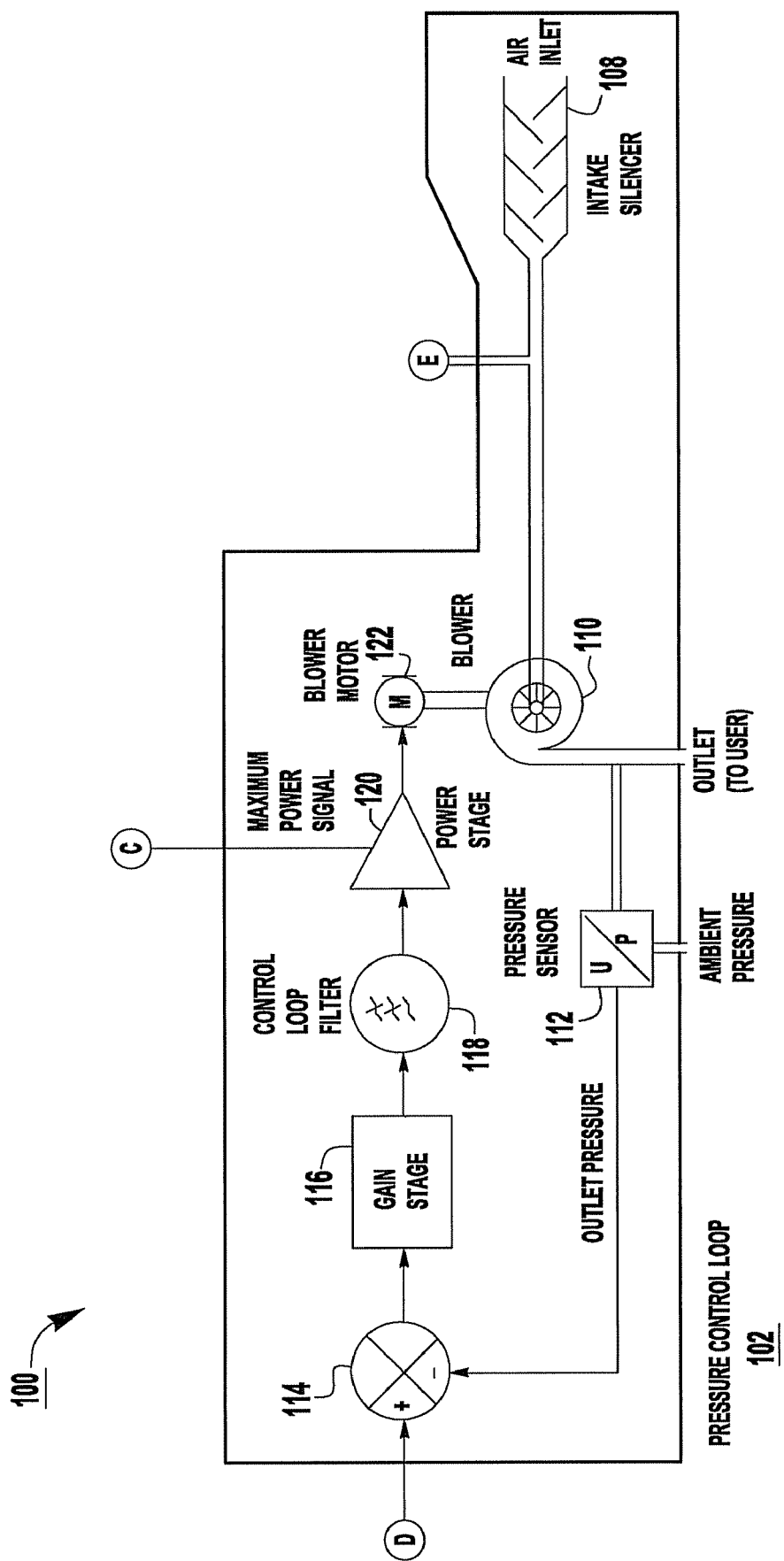

FIGS. 4A, 4B, and 4C are a block diagram of another embodiment of an exemplary PAP device.

Figure 5A:
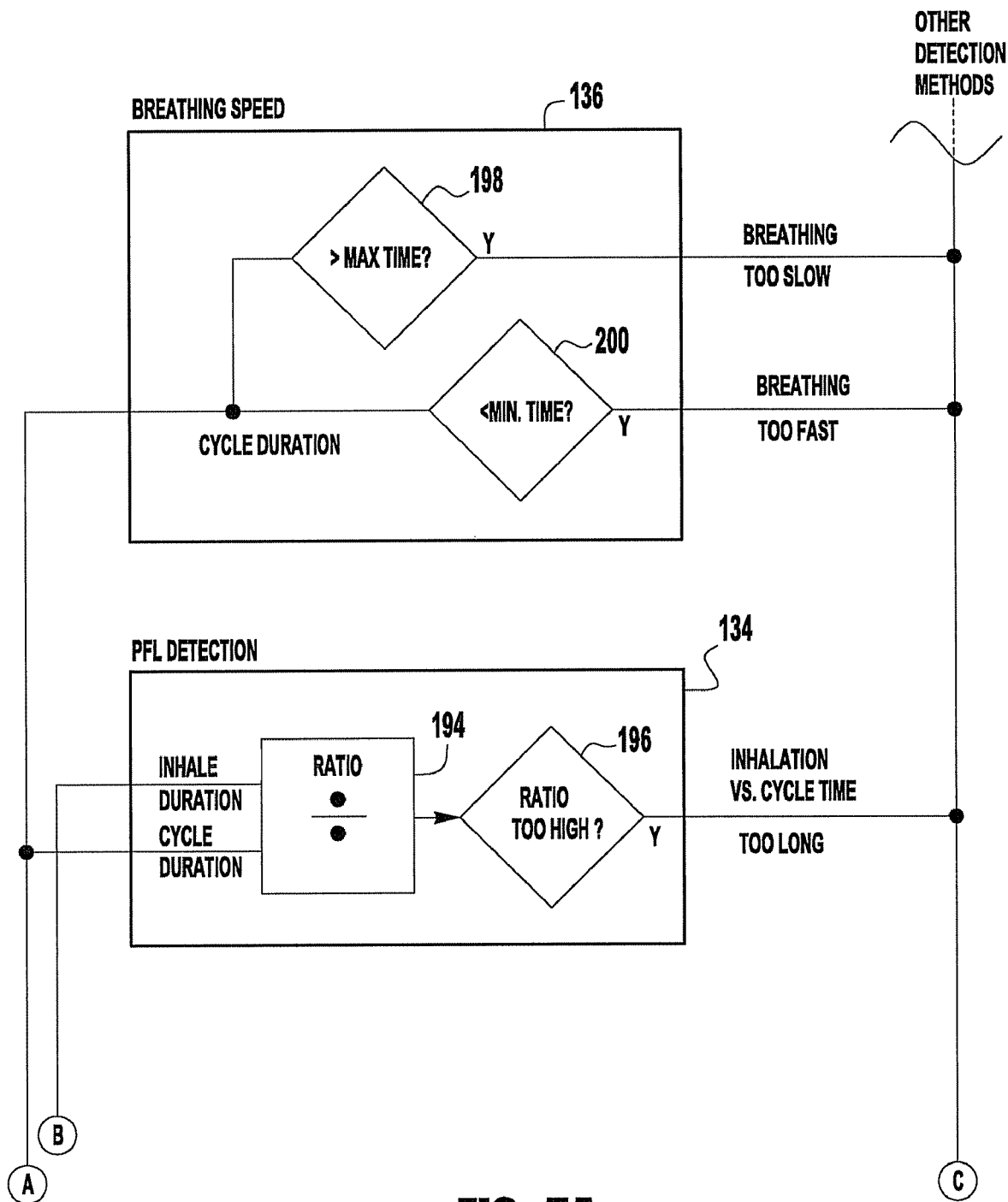
Figure 5B:
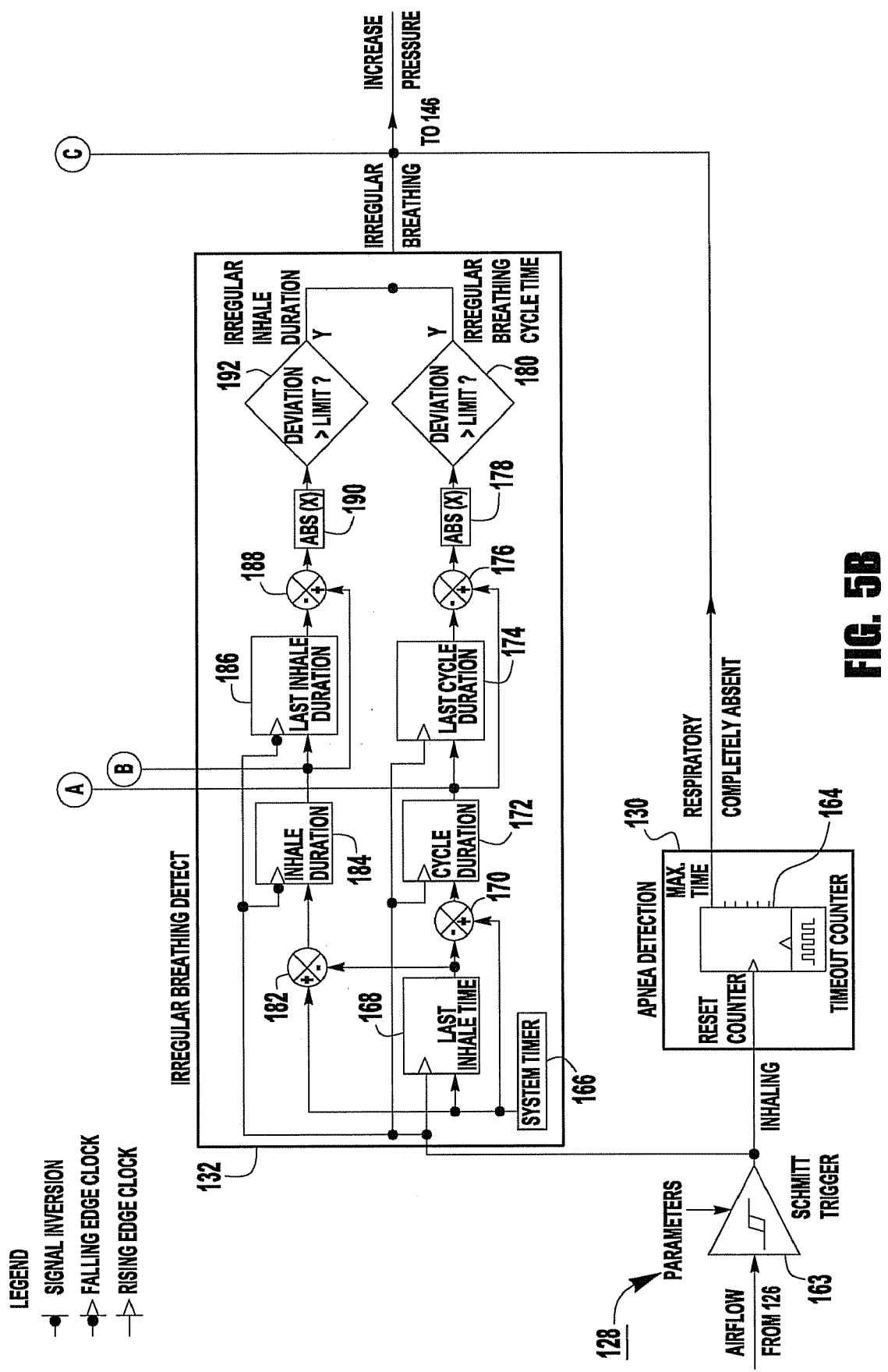

FIGS. 5A and 5B are a block diagram of an embodiment of an exemplary first portion of a respiratory checks logic for an exemplary PAP device.

Figure 6A:
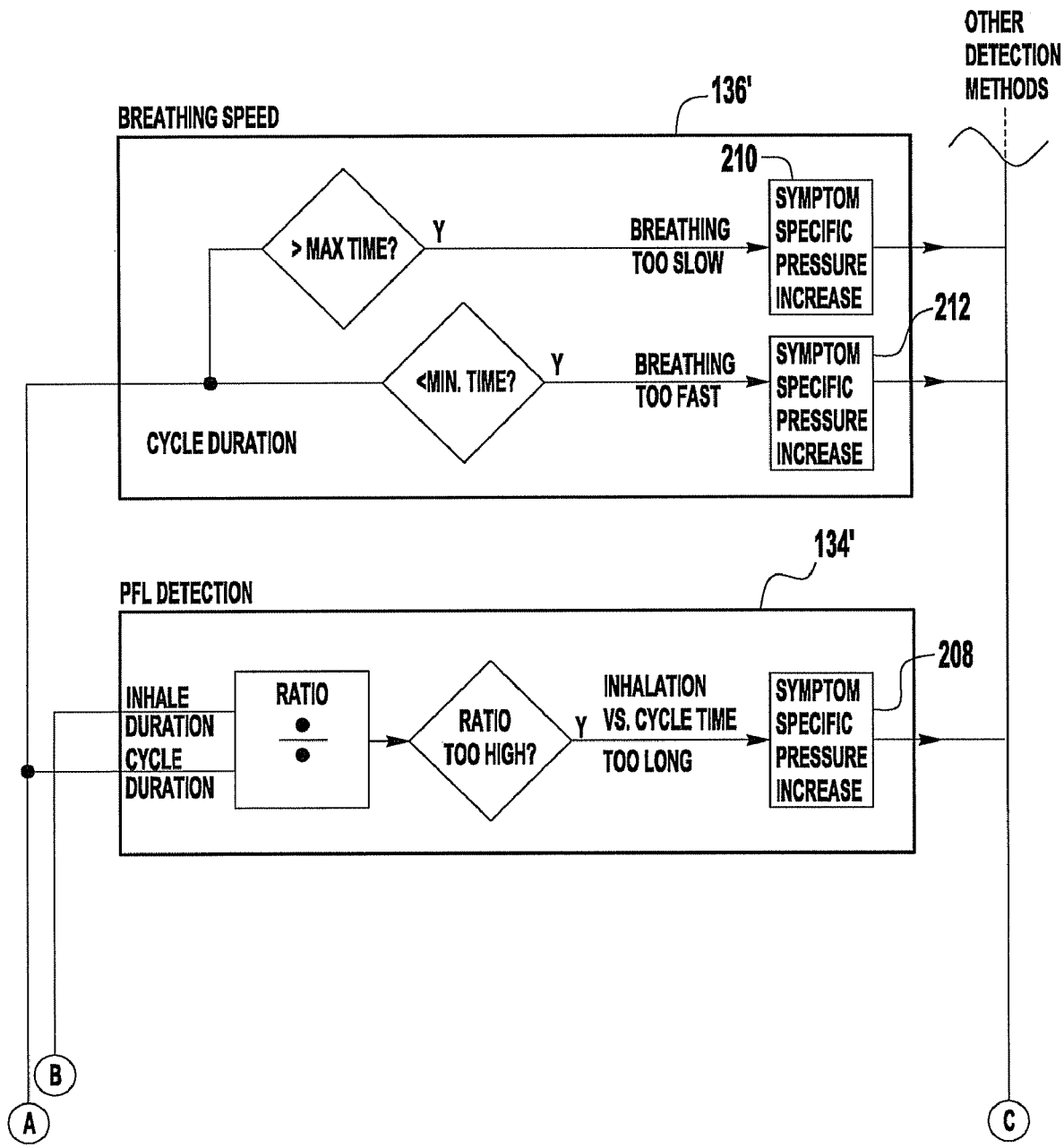
Figure 6B:
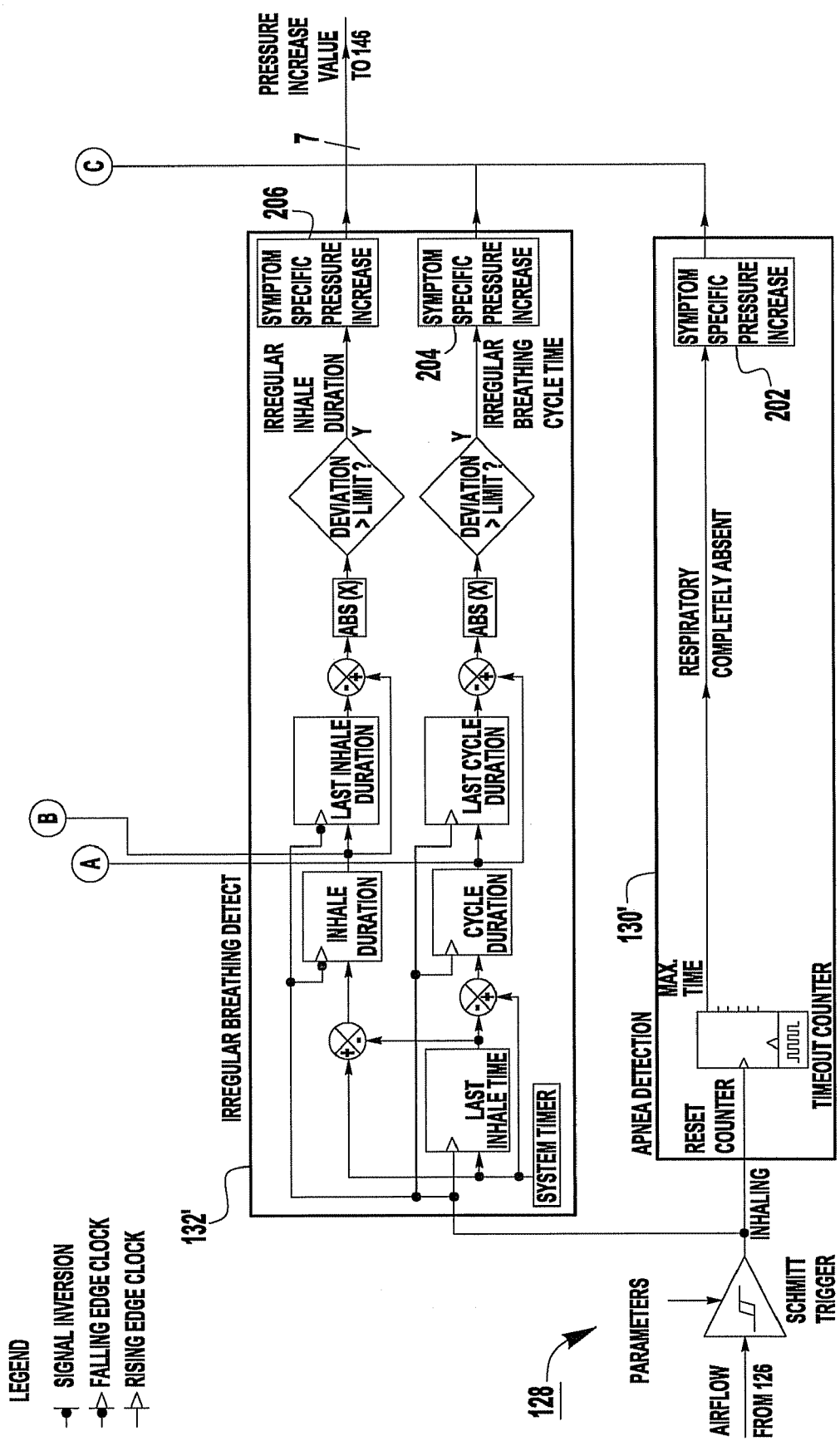

FIGS. 6A and 6B are a block diagram of another embodiment of an exemplary first portion of a respiratory checks logic for an exemplary PAP device.

Figure 7:
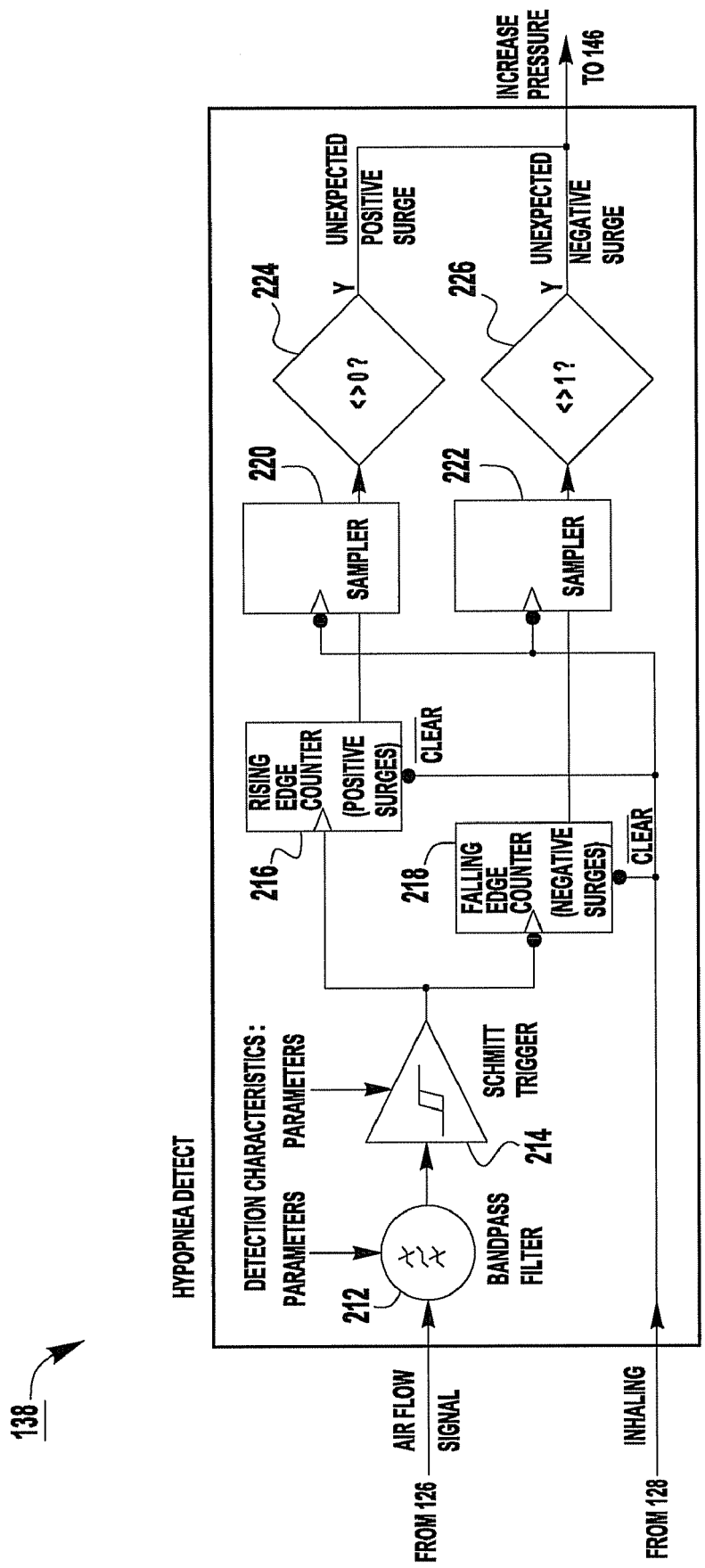

FIG. 7 is a block diagram of an embodiment of an exemplary second portion of a respiratory checks logic for an exemplary PAP device.

Figure 8:
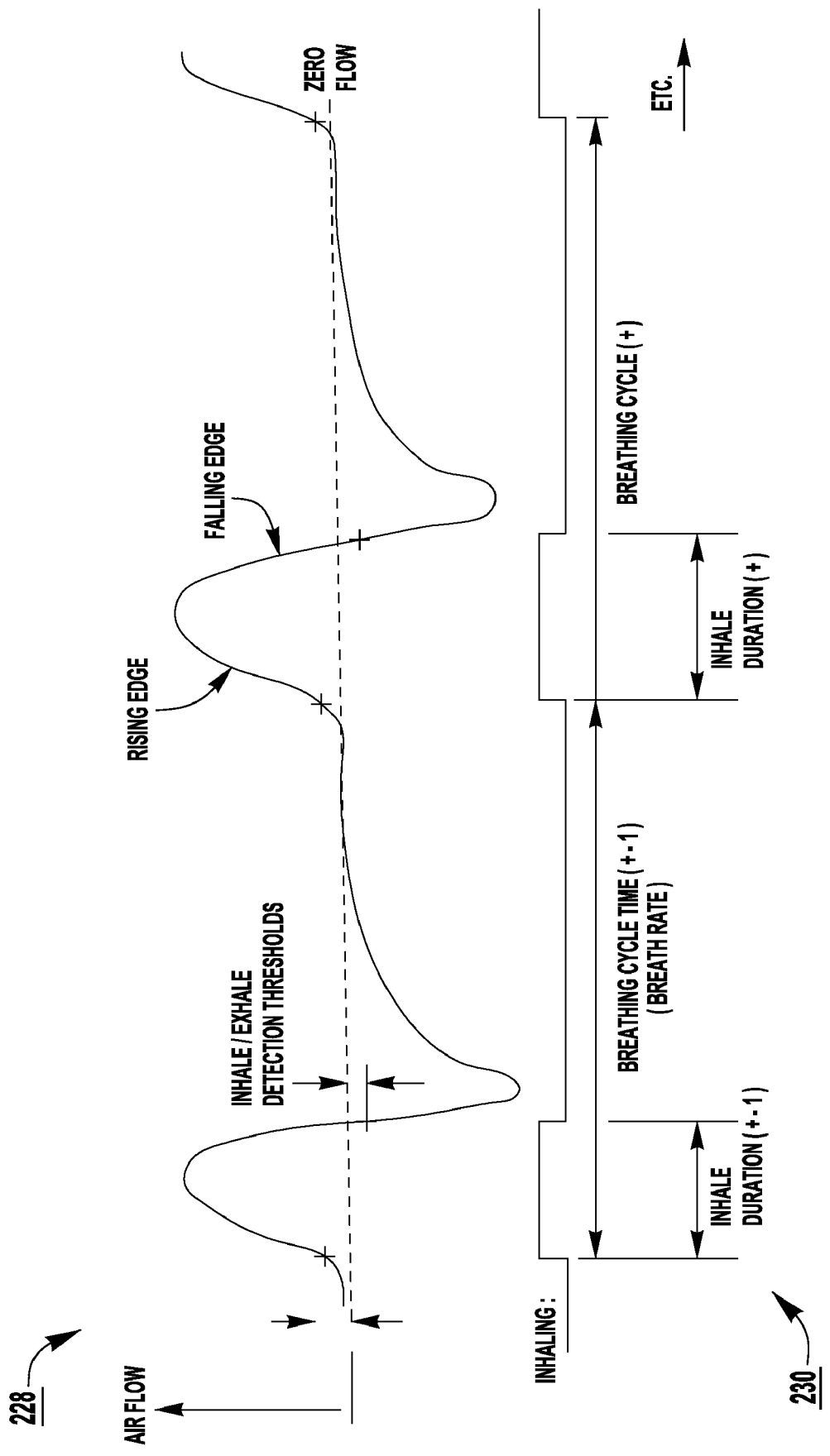

FIG. 8 shows exemplary signal waveforms associated with a monitored respiratory characteristic and a breathing cycle signal.

Figure 9:
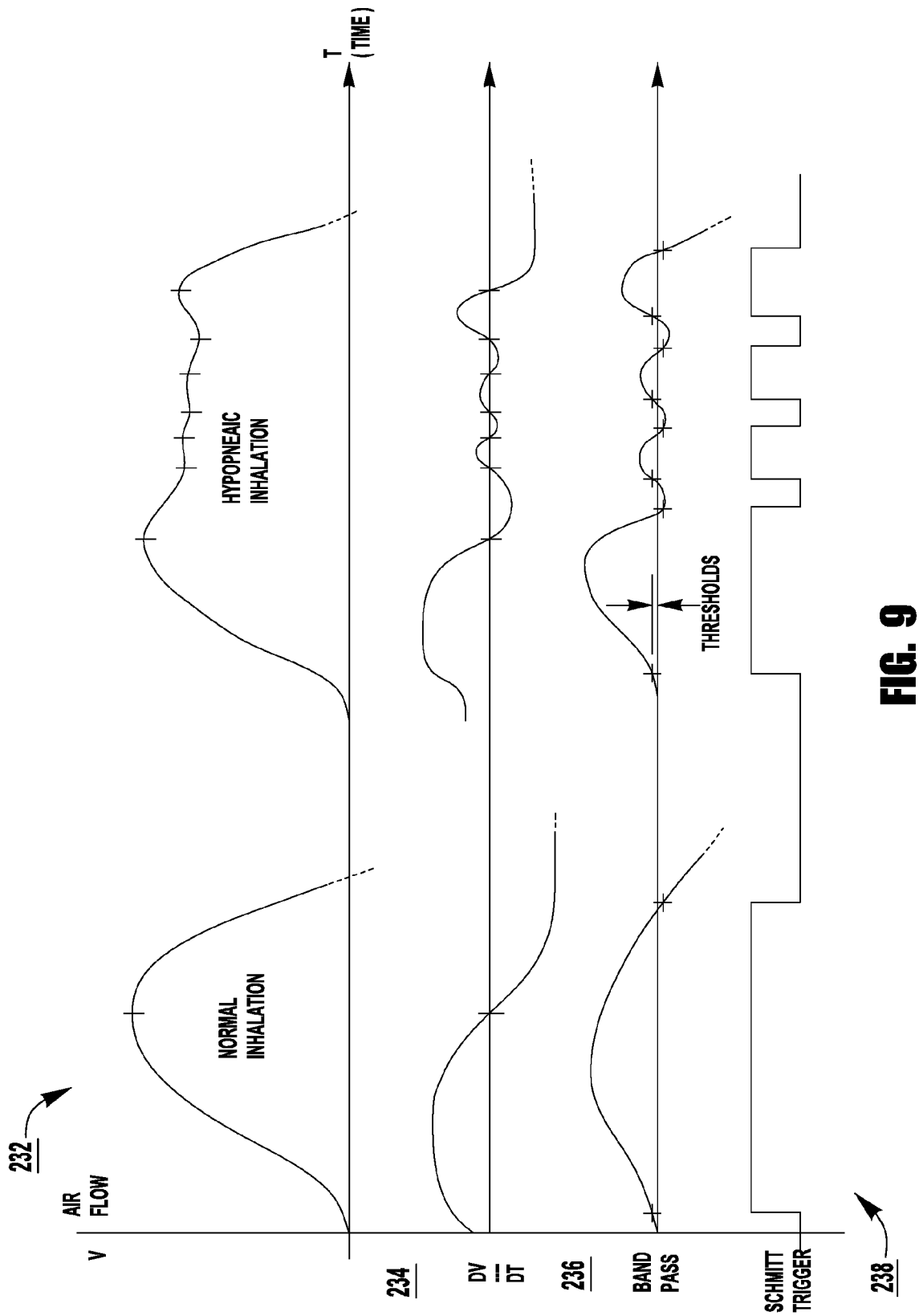

FIG. 9 shows exemplary signal waveforms associated with a monitored respiratory characteristic, a filtered respiration signal, and a triggered respiration signal.

Figure 10:
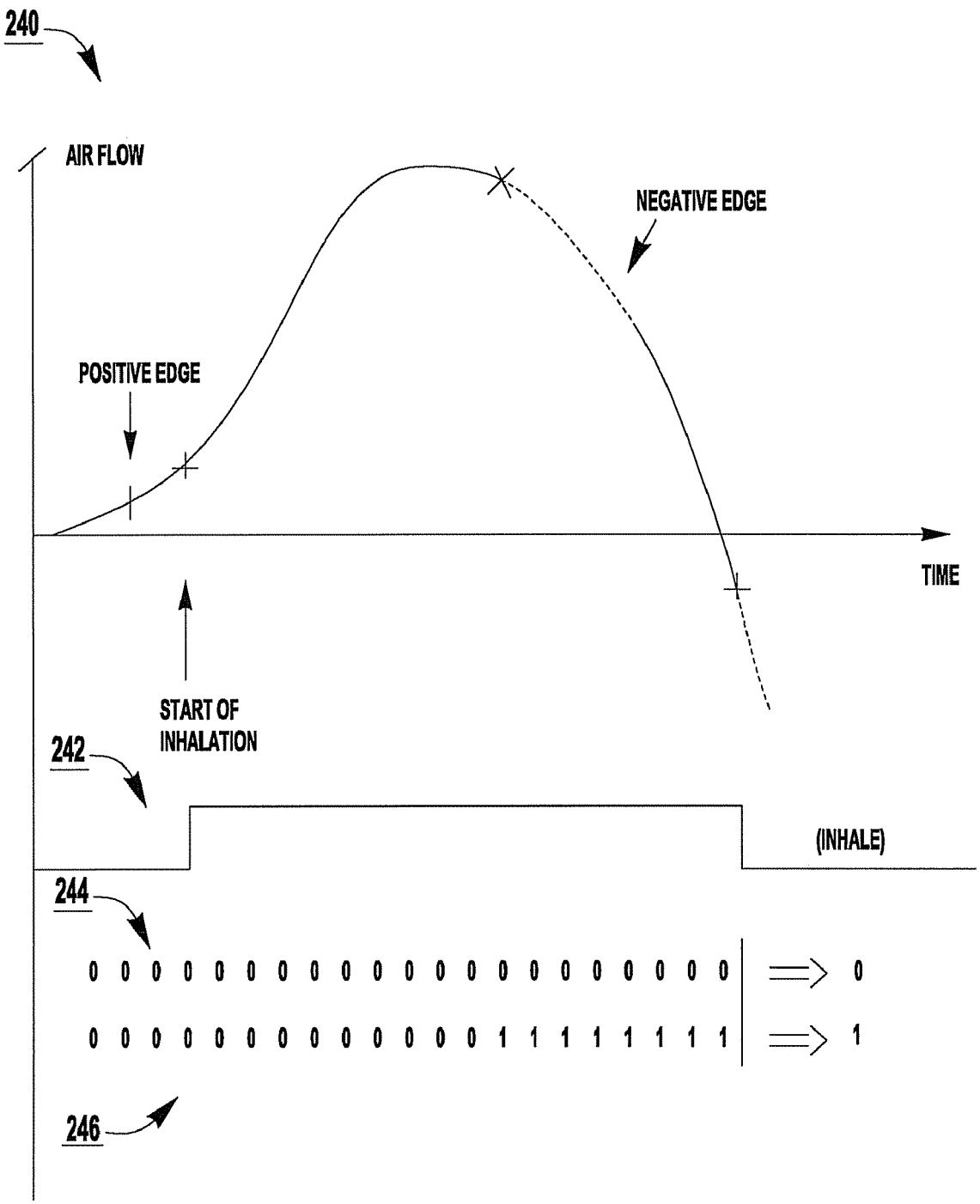

FIG. 10 shows exemplary signal waveforms associated with a monitored respiratory characteristic and a breathing cycle signal and exemplary count sequences associated with positive and negative surge counters.

FIG. 11 shows exemplary signal waveforms associated with a monitored respiratory characteristic and a breathing cycle signal and exemplary count sequences associated with positive and negative surge counters.

Figure 12A:
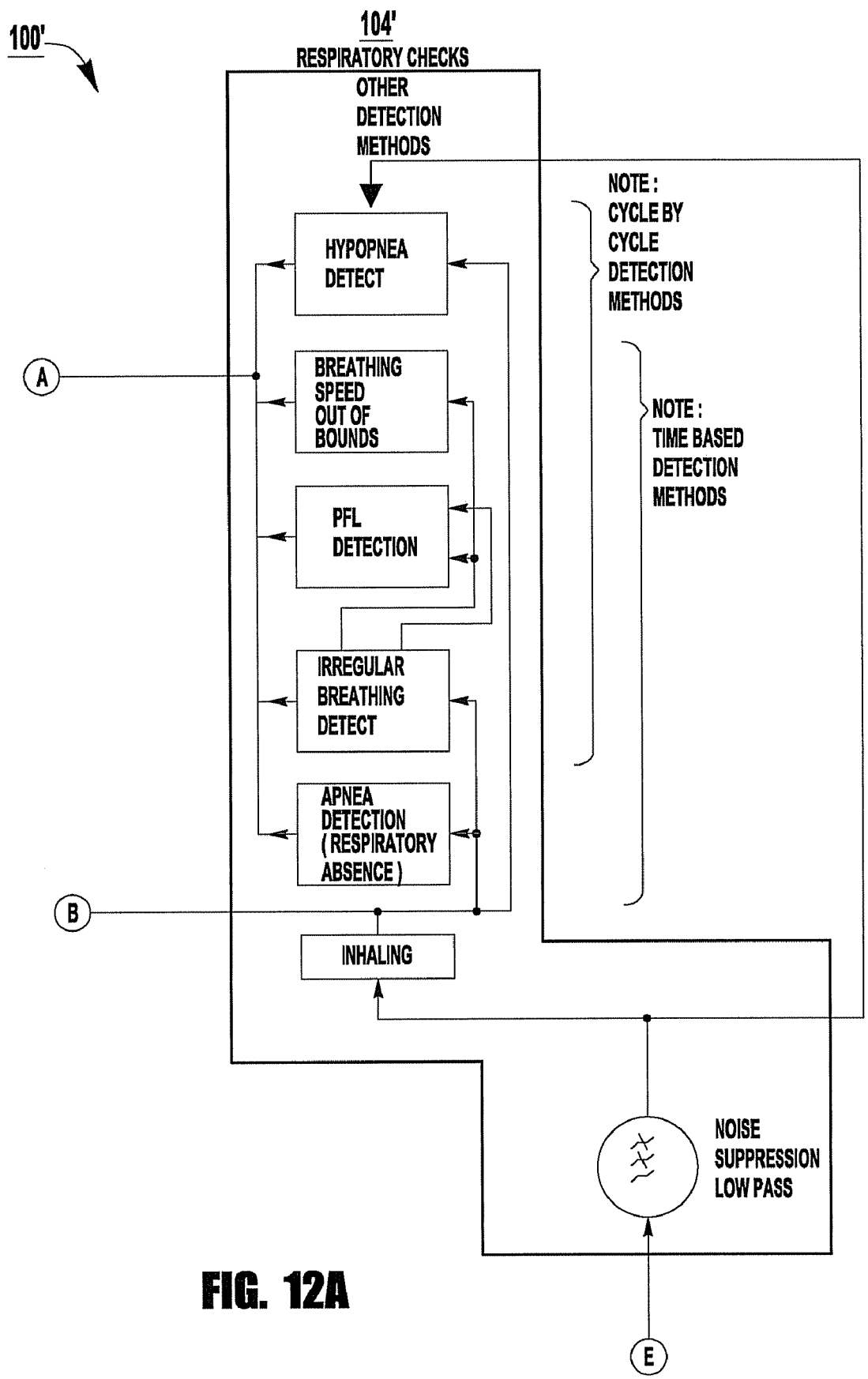
Figure 12B:
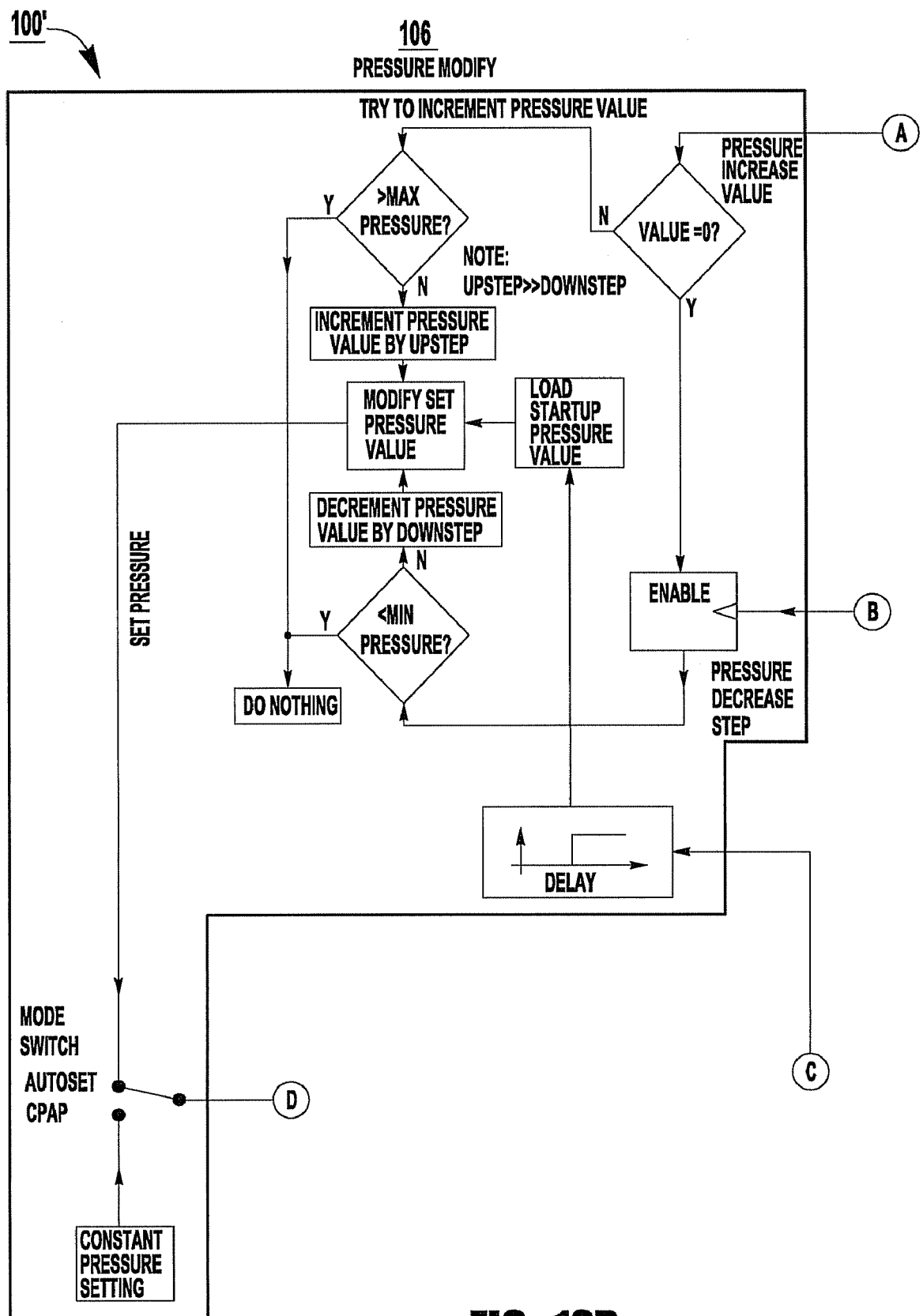
Figure 12C:
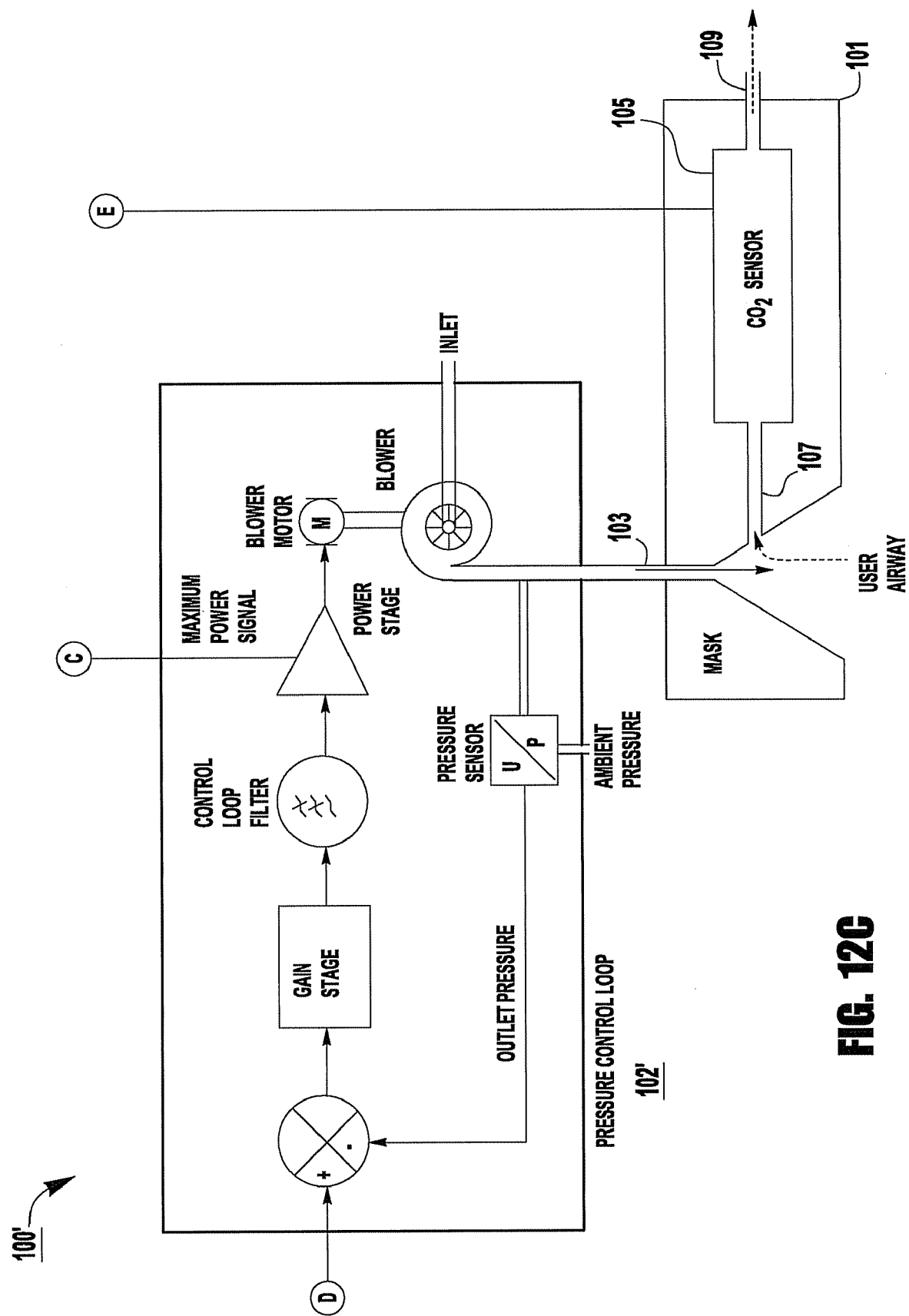

FIGS. 12A, 12B and 12C are a block diagram of another embodiment of an exemplary PAP device.

Figure 13A:
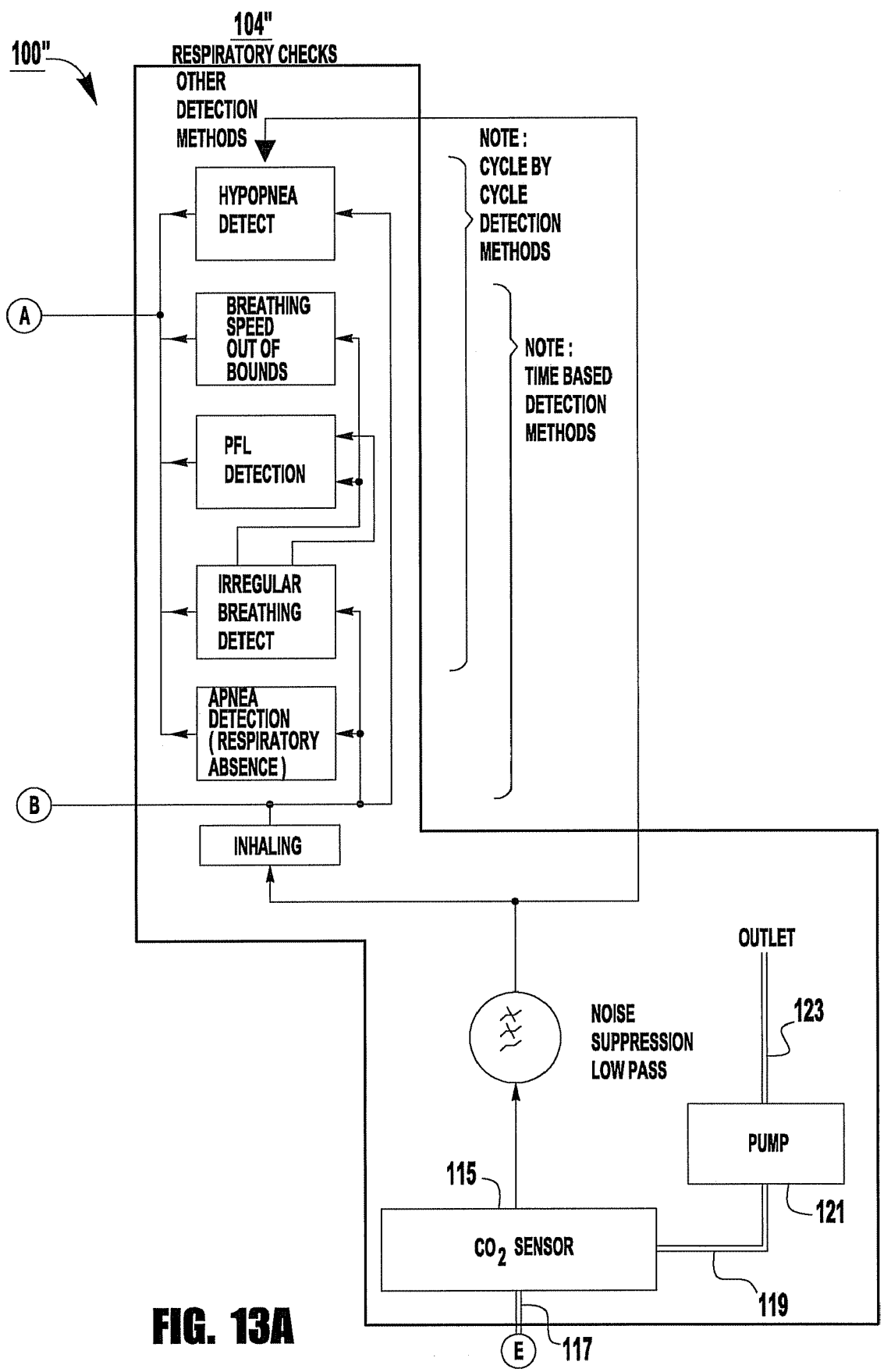
Figure 13B:
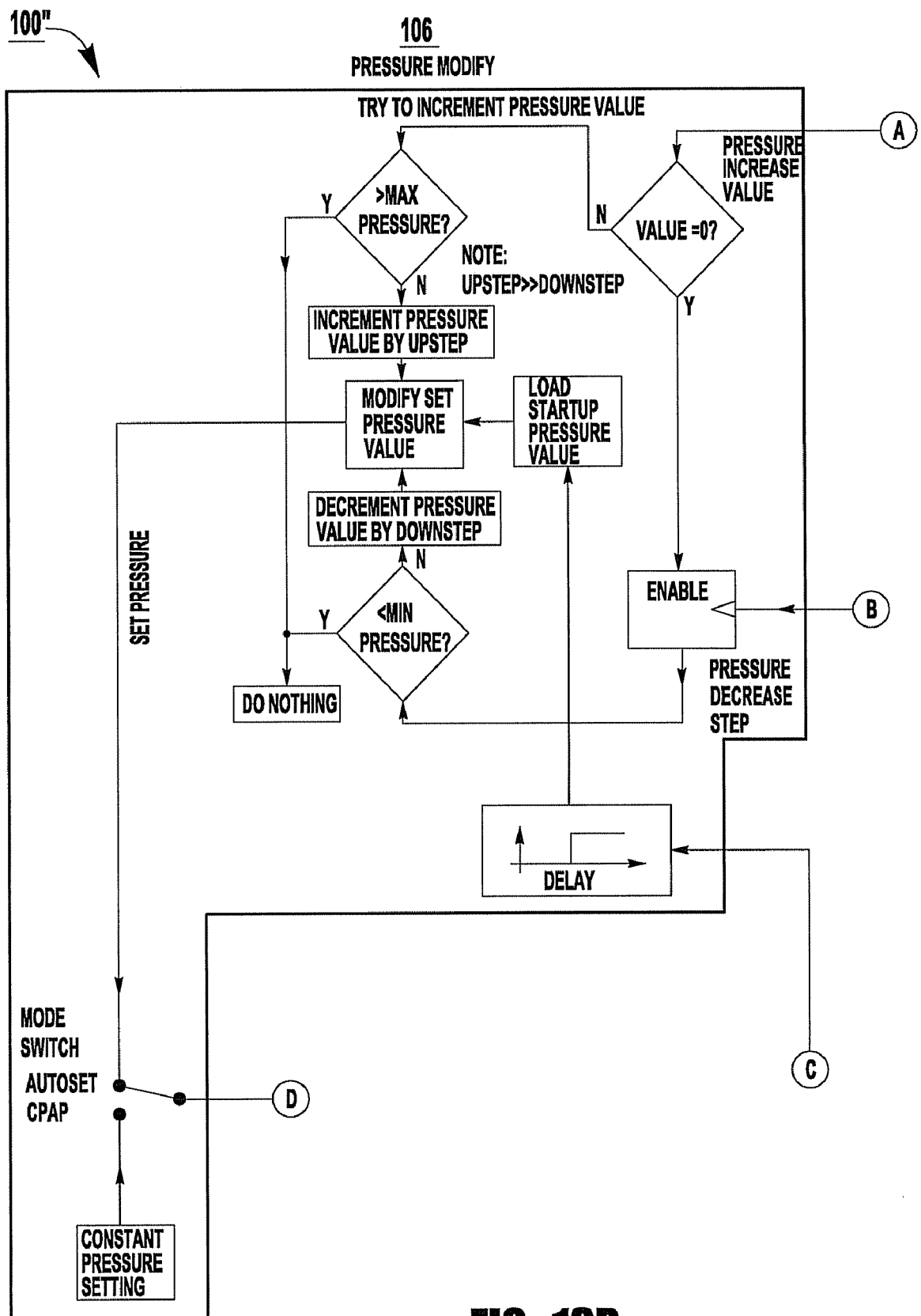
Figure 13C:
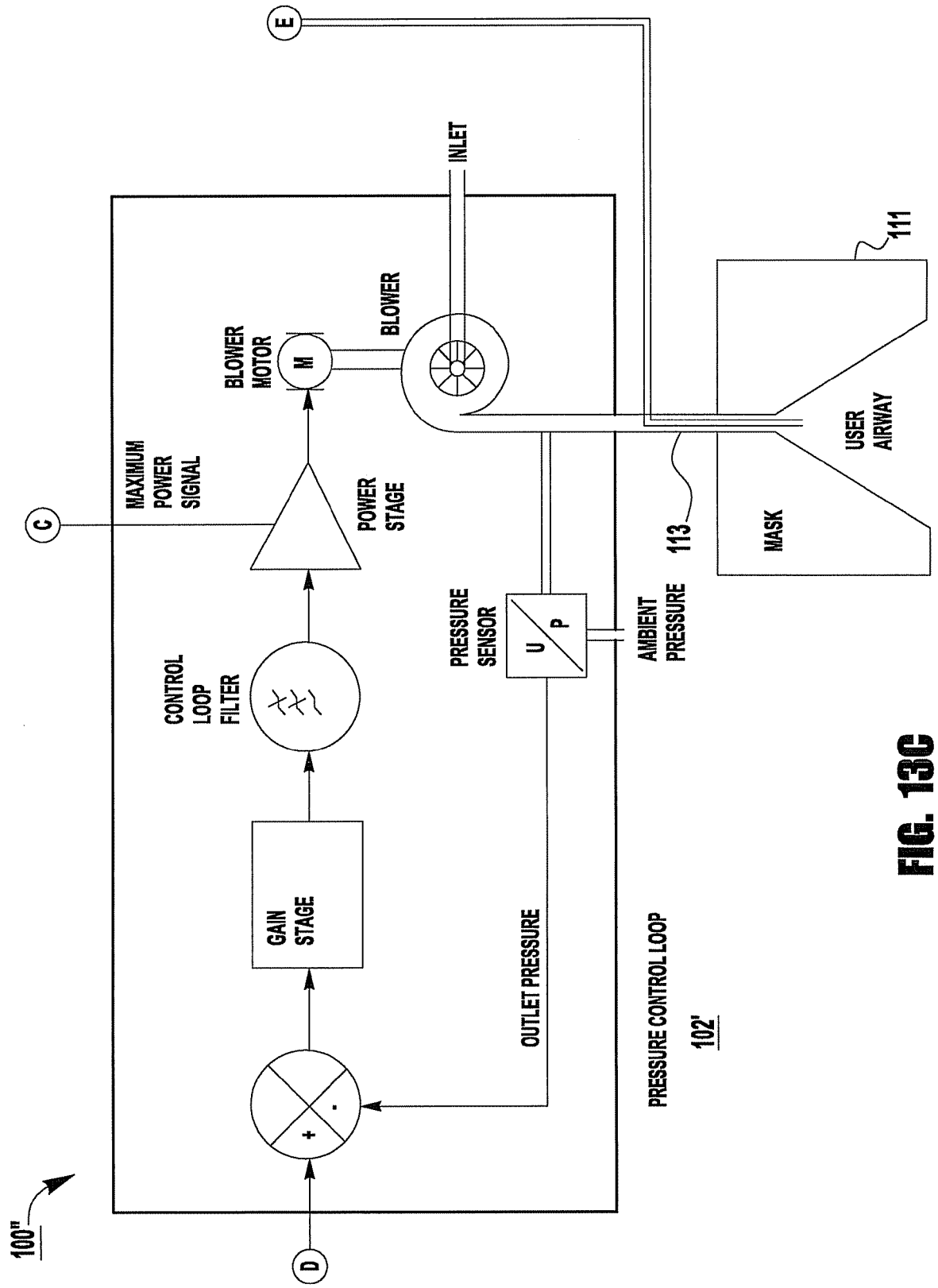

FIGS. 13A, 13B and 13C are a block diagram of yet another embodiment of an exemplary PAP device.

Figure 14A:
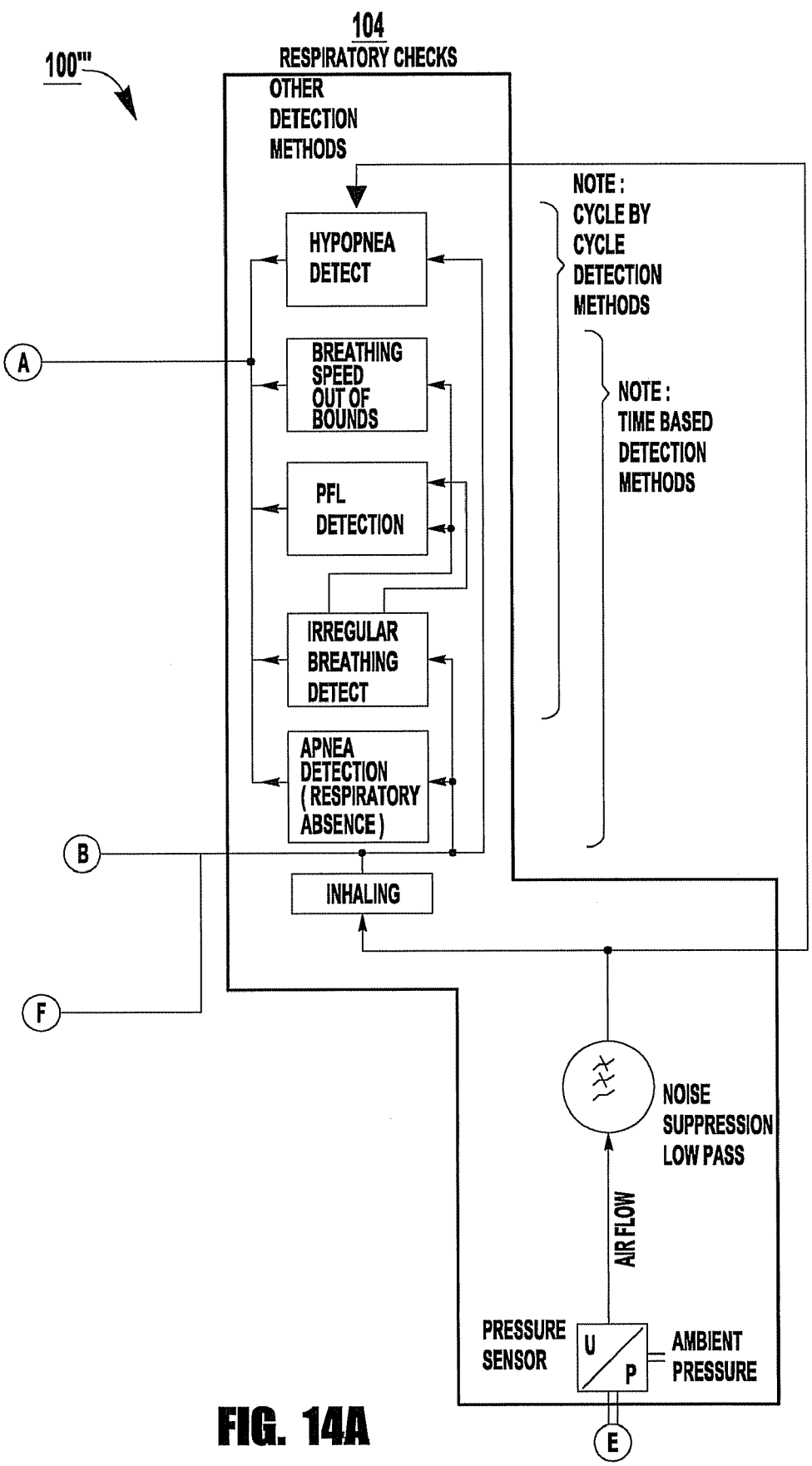
Figure 14B:
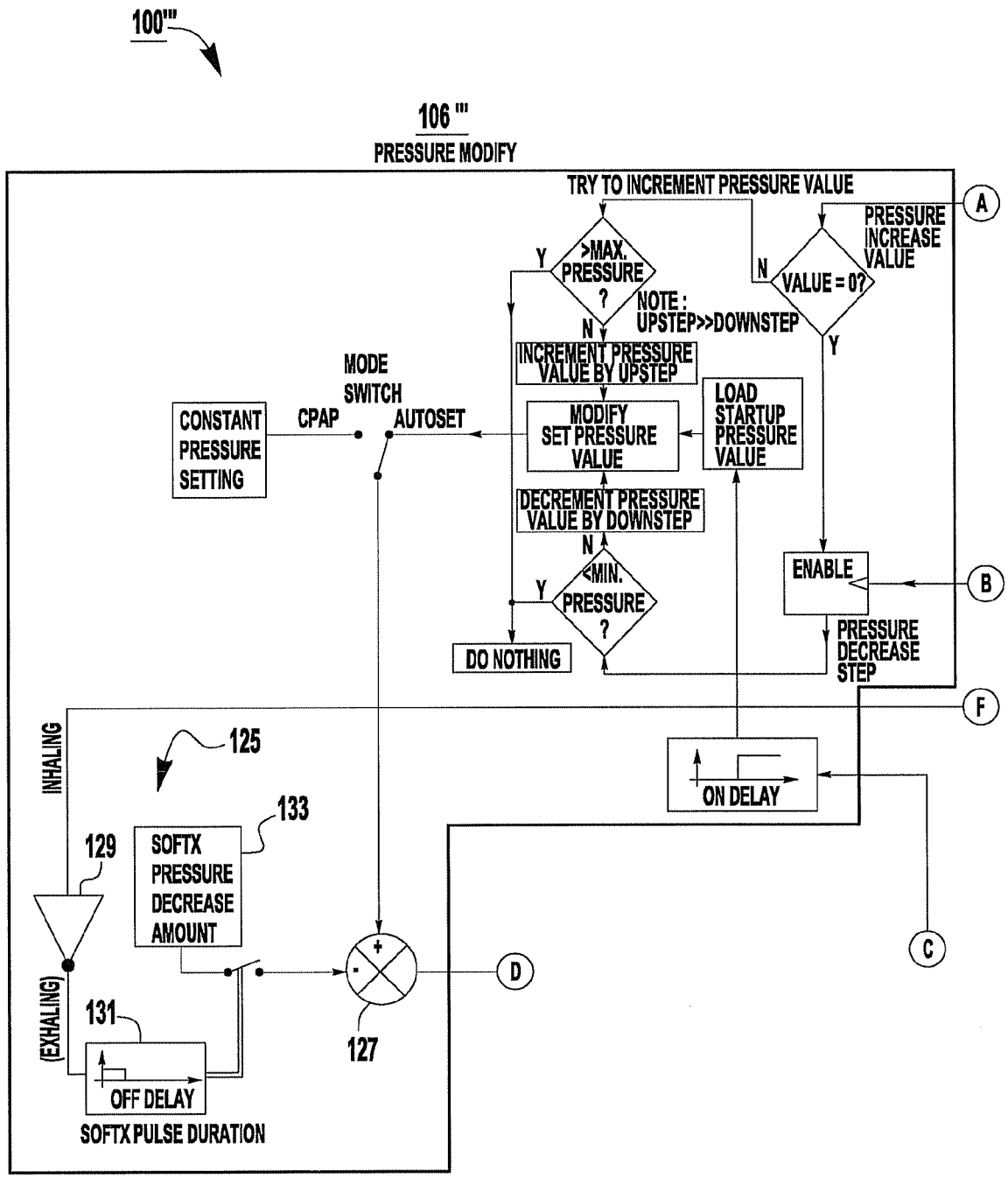
Figure 14C:
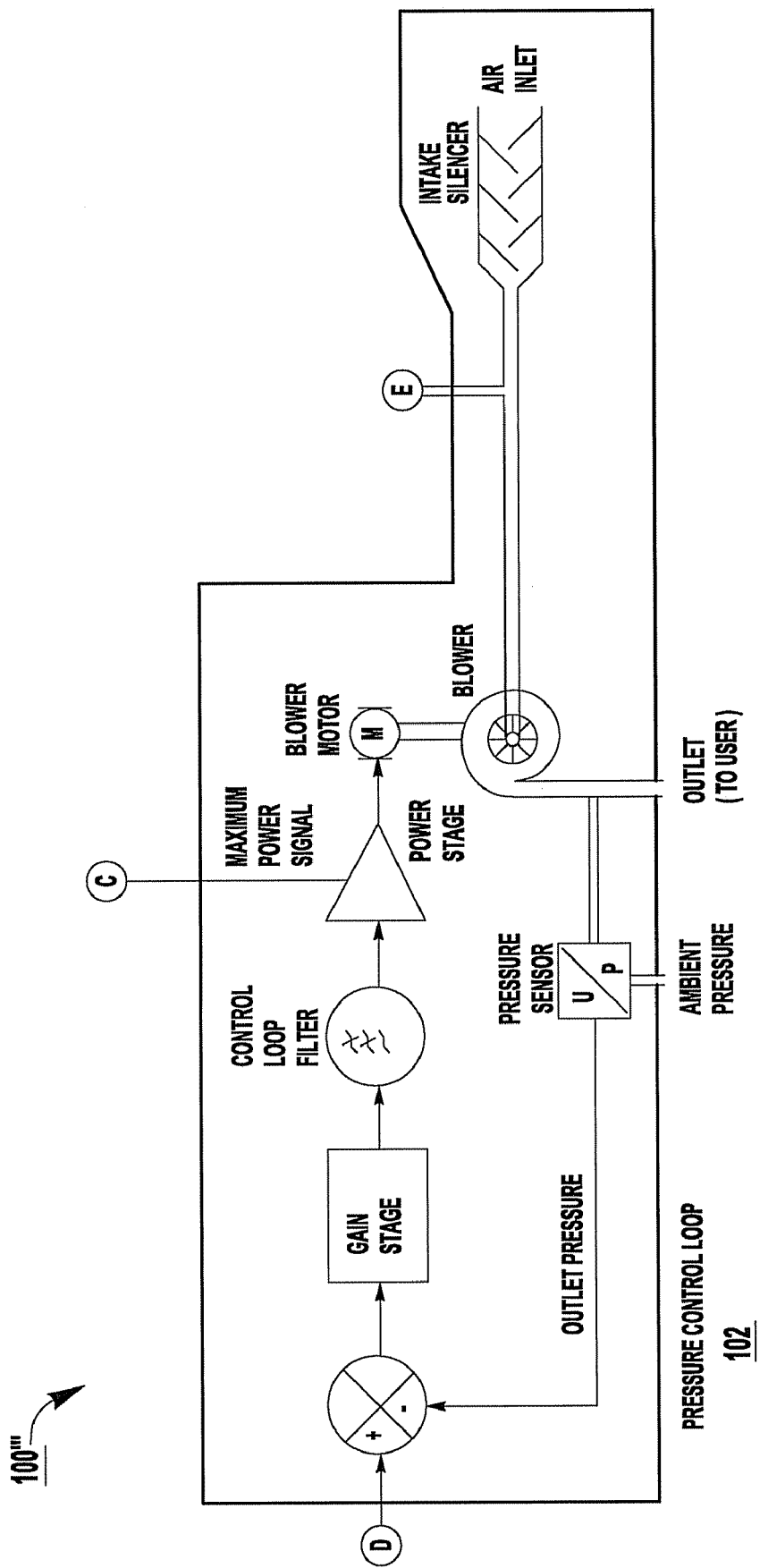

FIGS. 14A, 14B and 14C are a block diagram of still another embodiment of an exemplary PAP device.

Figure 15A:
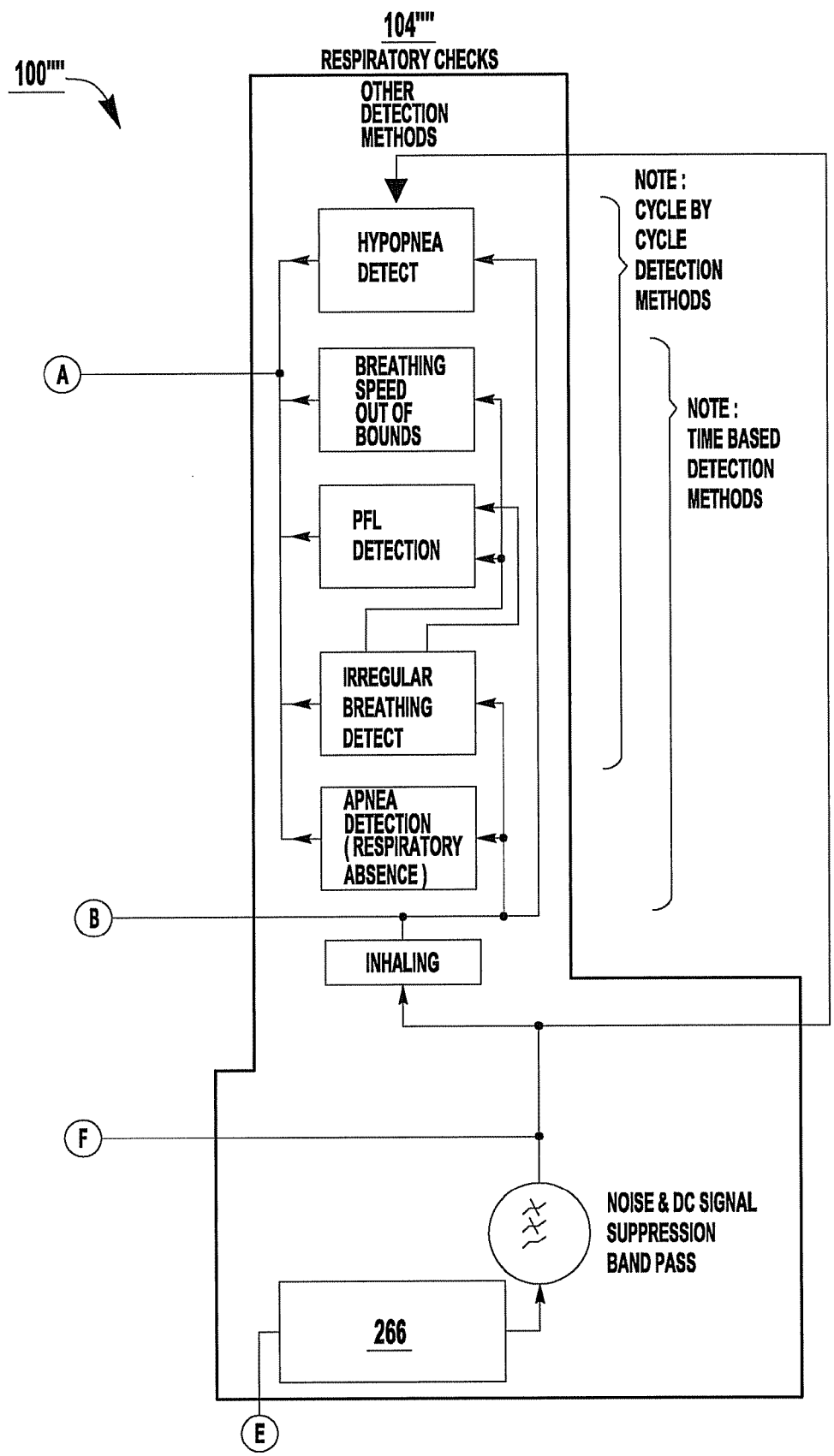
Figure 15B:
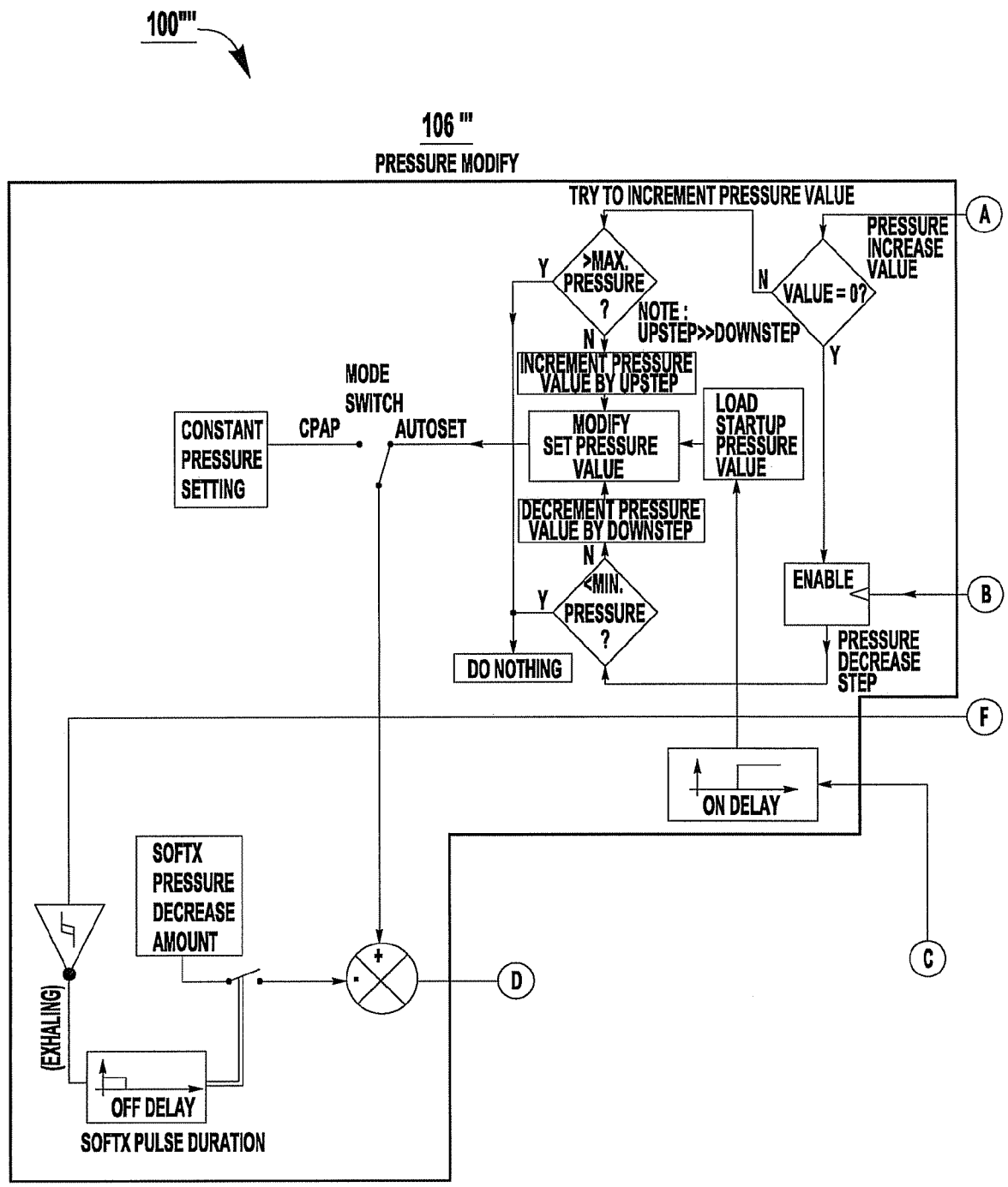
Figure 15C:
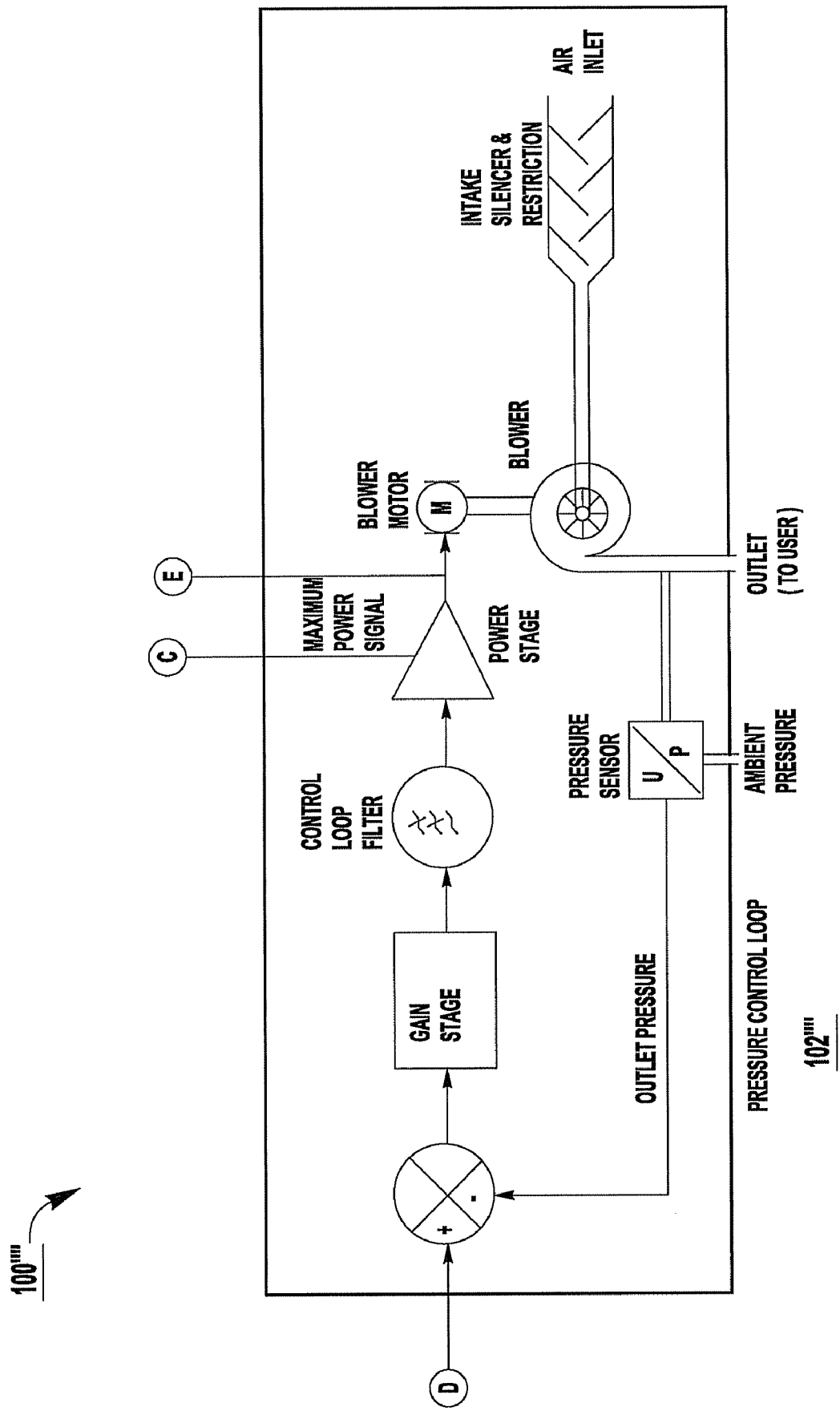

FIGS. 15A, 15B and 15C are a block diagram of still yet another embodiment of an exemplary PAP device.

Figure 16:
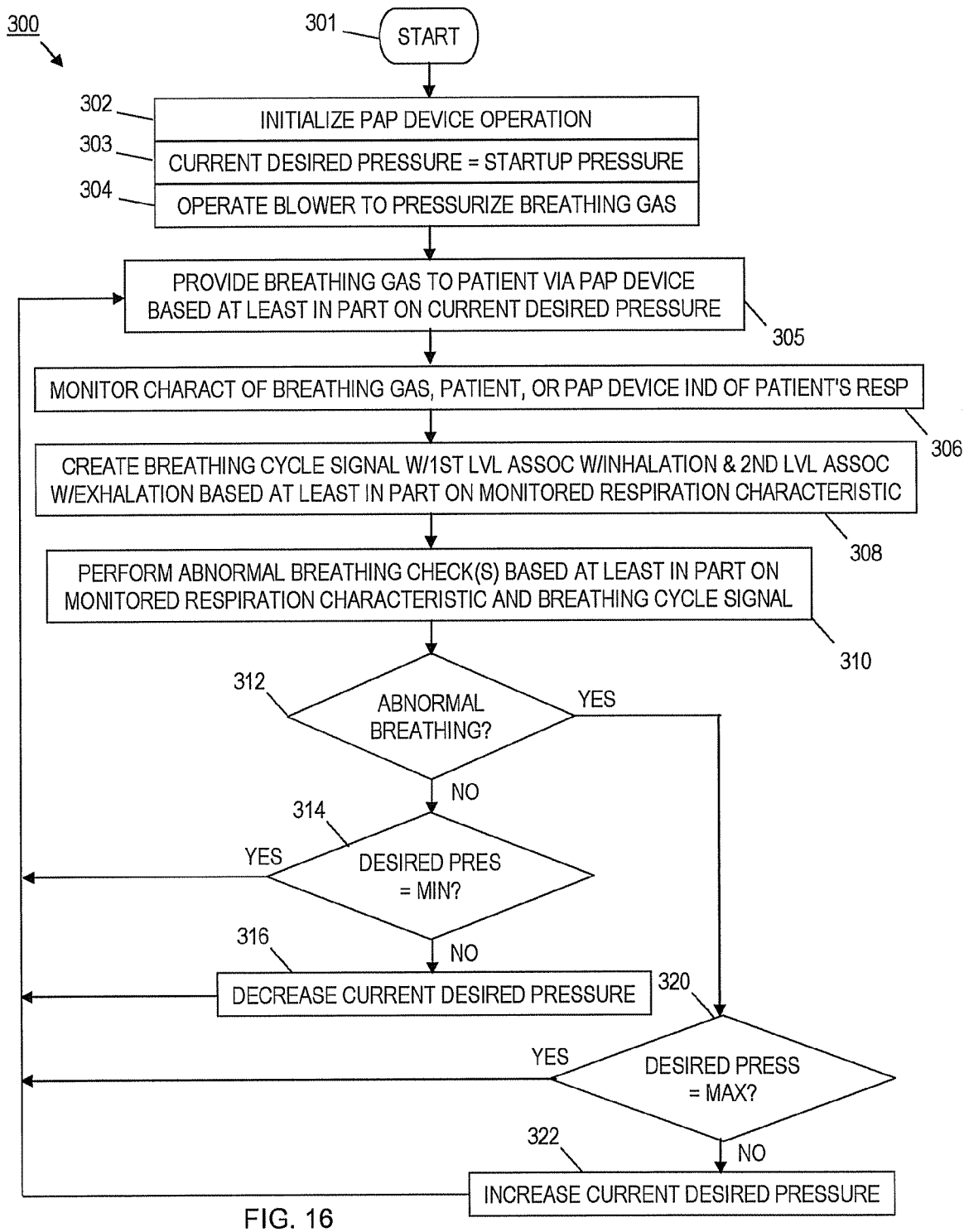

FIG. 16 is a flow chart of an embodiment of an exemplary process for adjusting a desired pressure in a PAP device.

Figure 17:
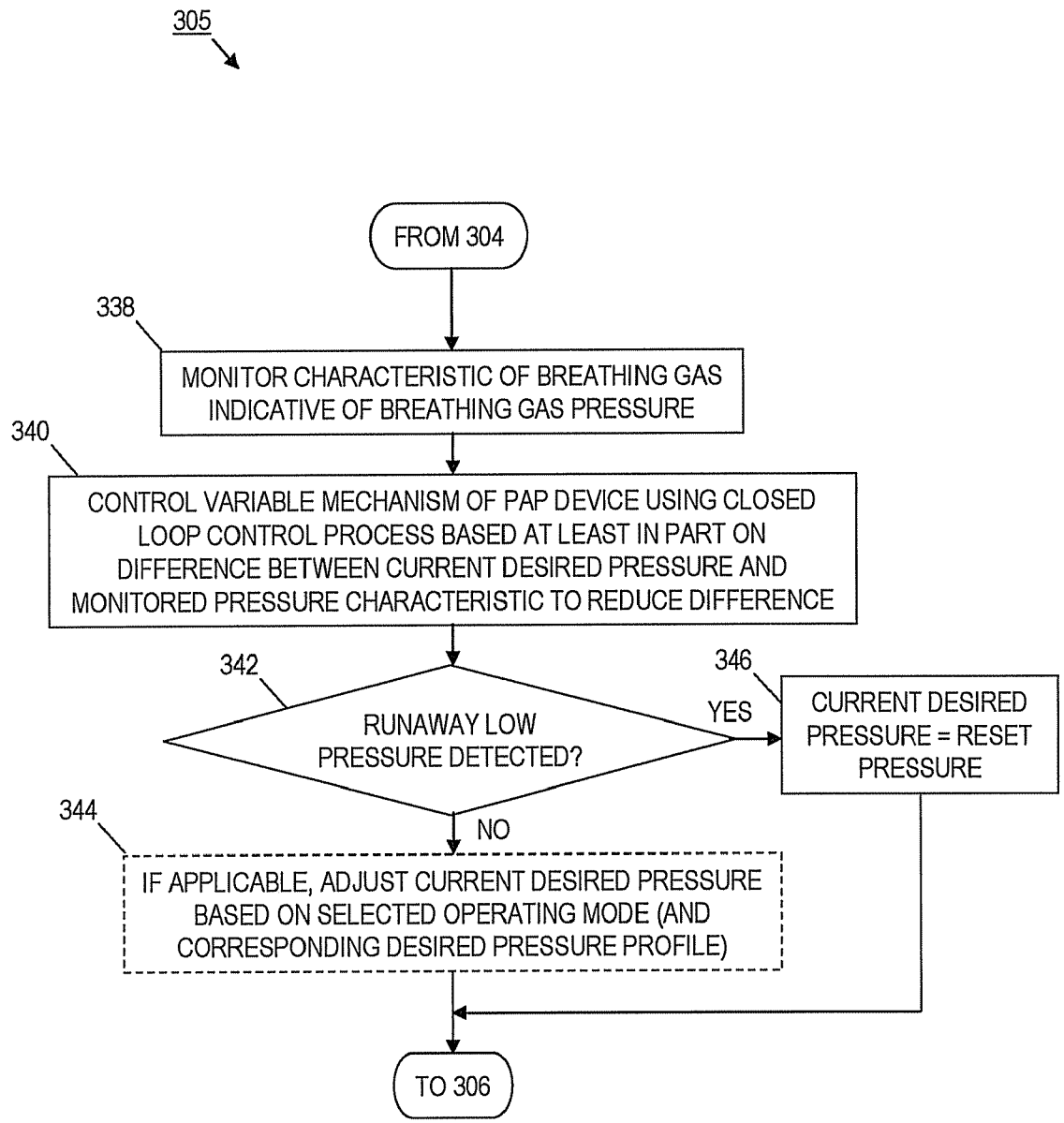

FIG. 17 is a flow chart of an embodiment of an exemplary process for providing a breathing gas to a patient based on a desired pressure.

Figure 18:
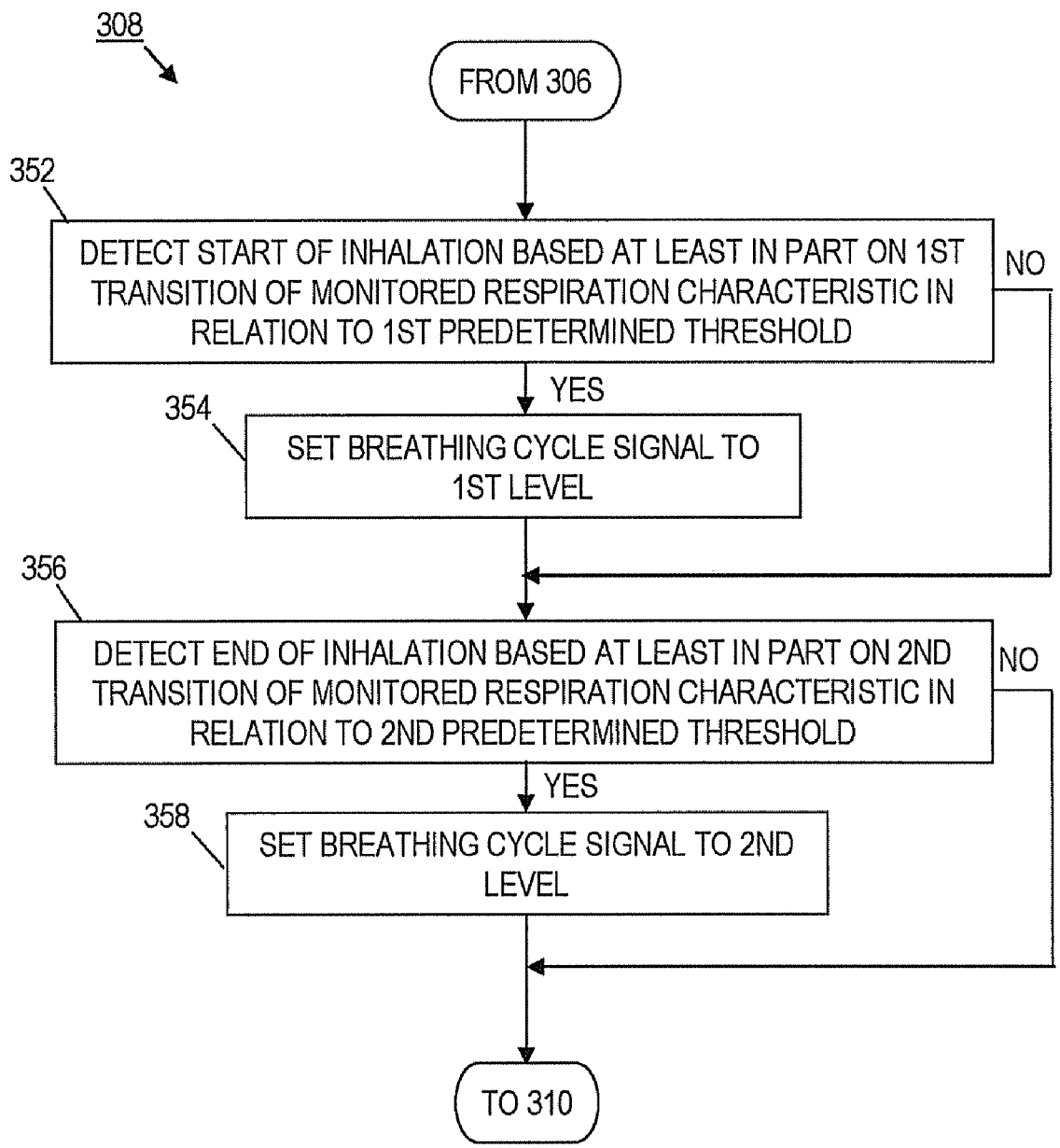

FIG. 18 is a flow chart of an embodiment of an exemplary process for generating a breathing cycle signal.

Figure 19:
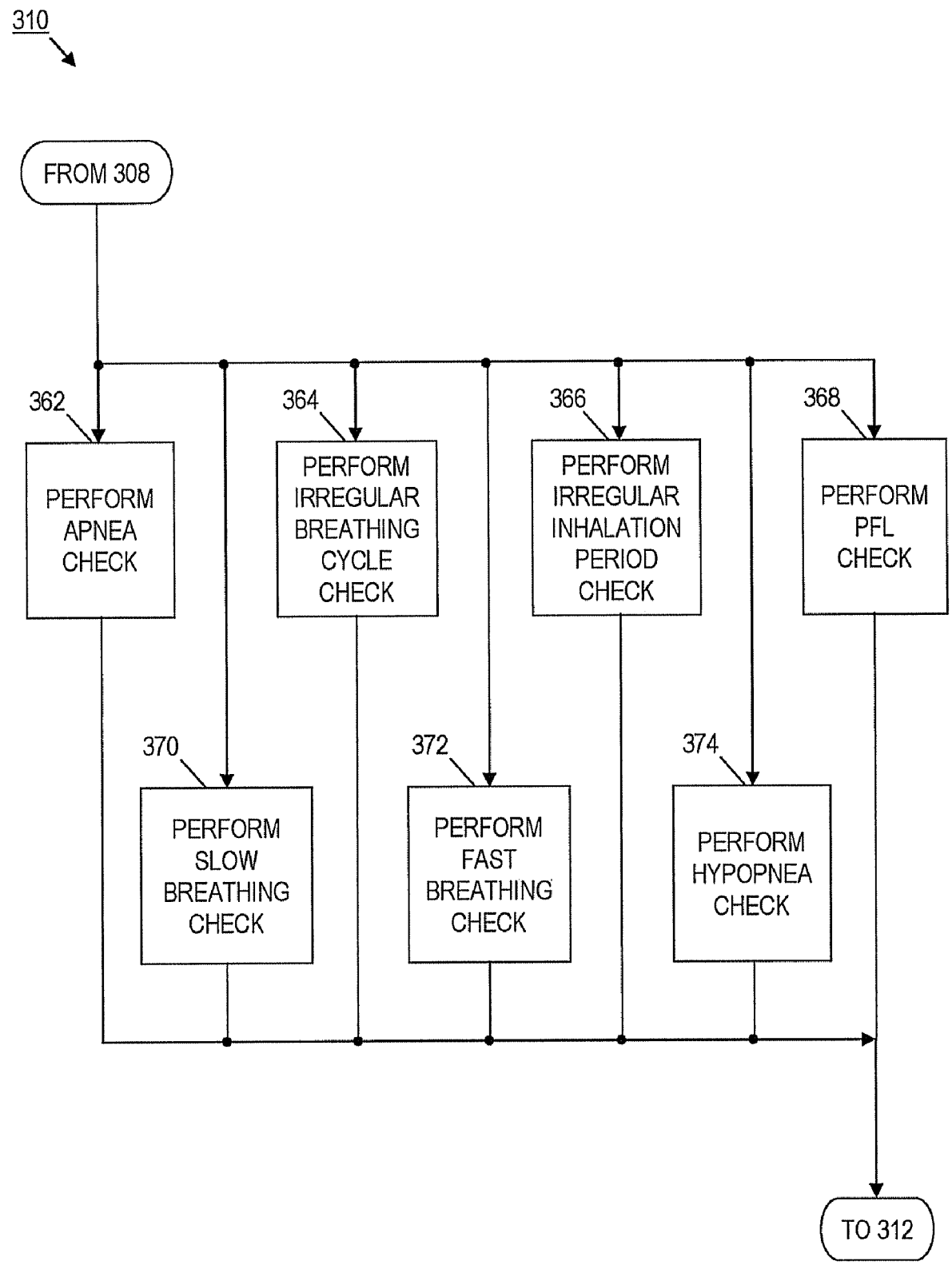

FIG. 19 is a flow chart of an embodiment of an exemplary process for performing one or more abnormal breathing checks.

Figure 20:
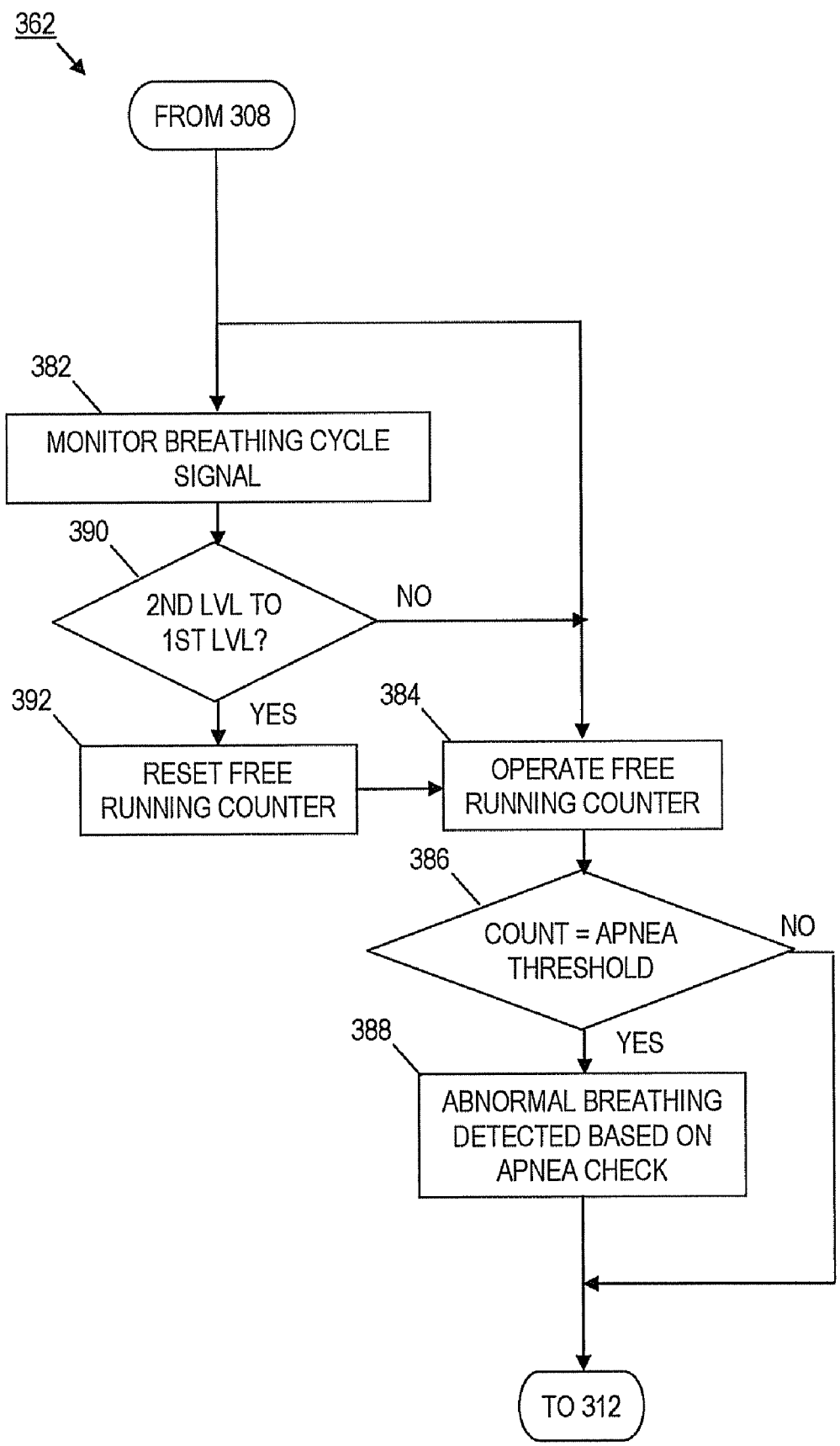

FIG. 20 is a flow chart of an embodiment of an exemplary process for performing an apnea check.

Figure 21:
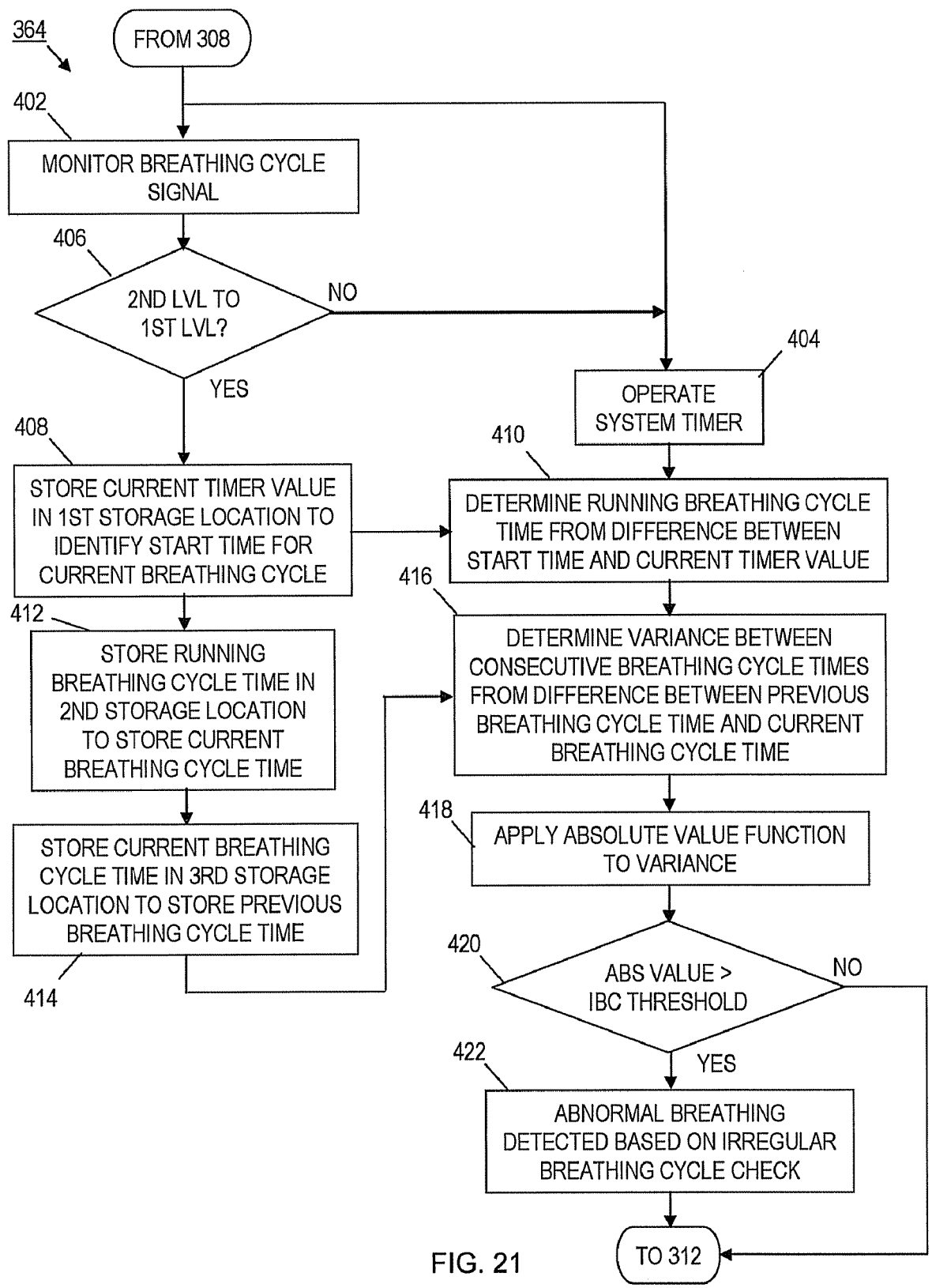

FIG. 21 is a flow chart of an embodiment of an exemplary process for performing an irregular breathing cycle check.

Figure 22:
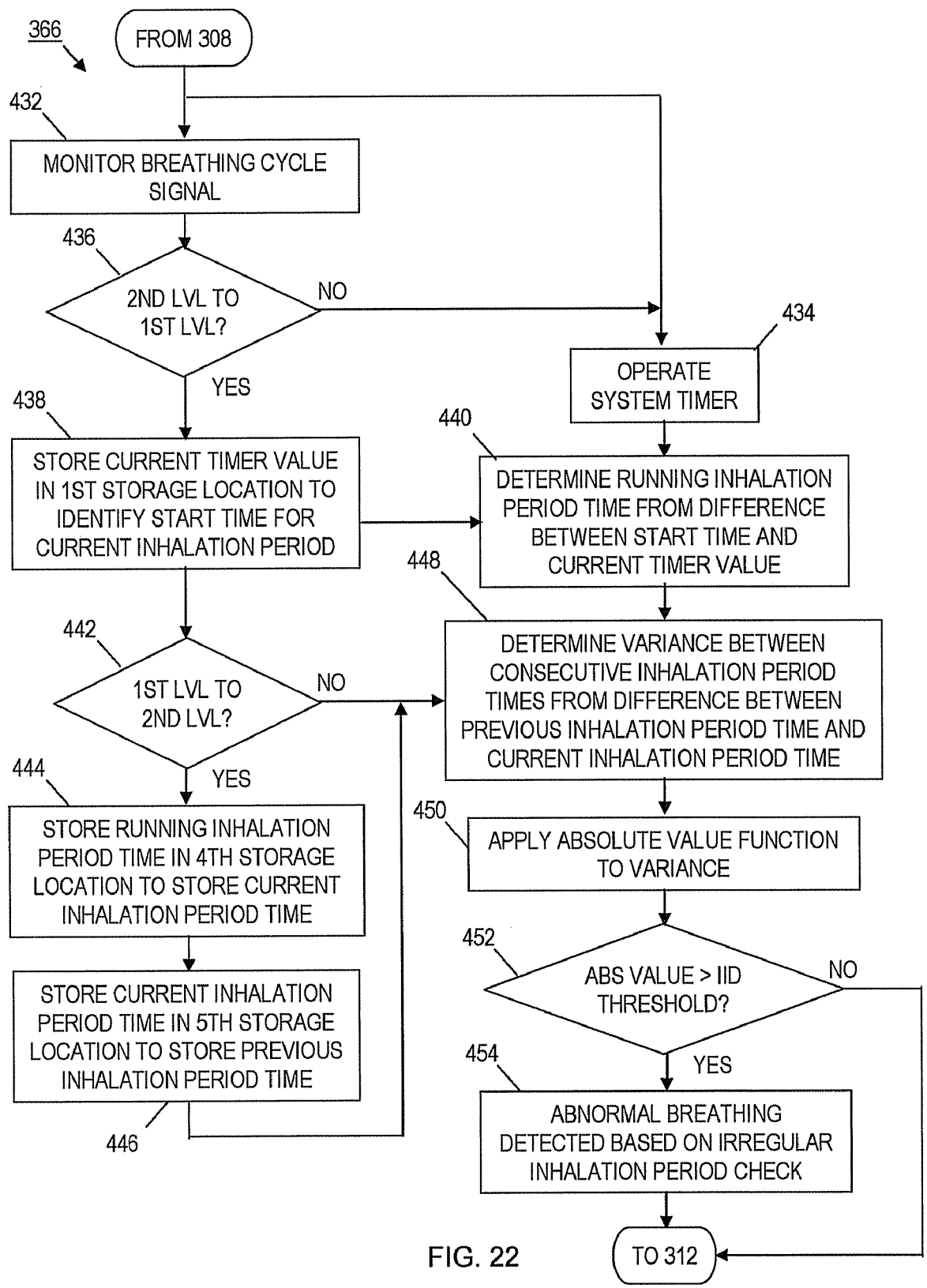

FIG. 22 is a flow chart of an embodiment of an exemplary process for performing an irregular inhalation period check.

Figure 23:
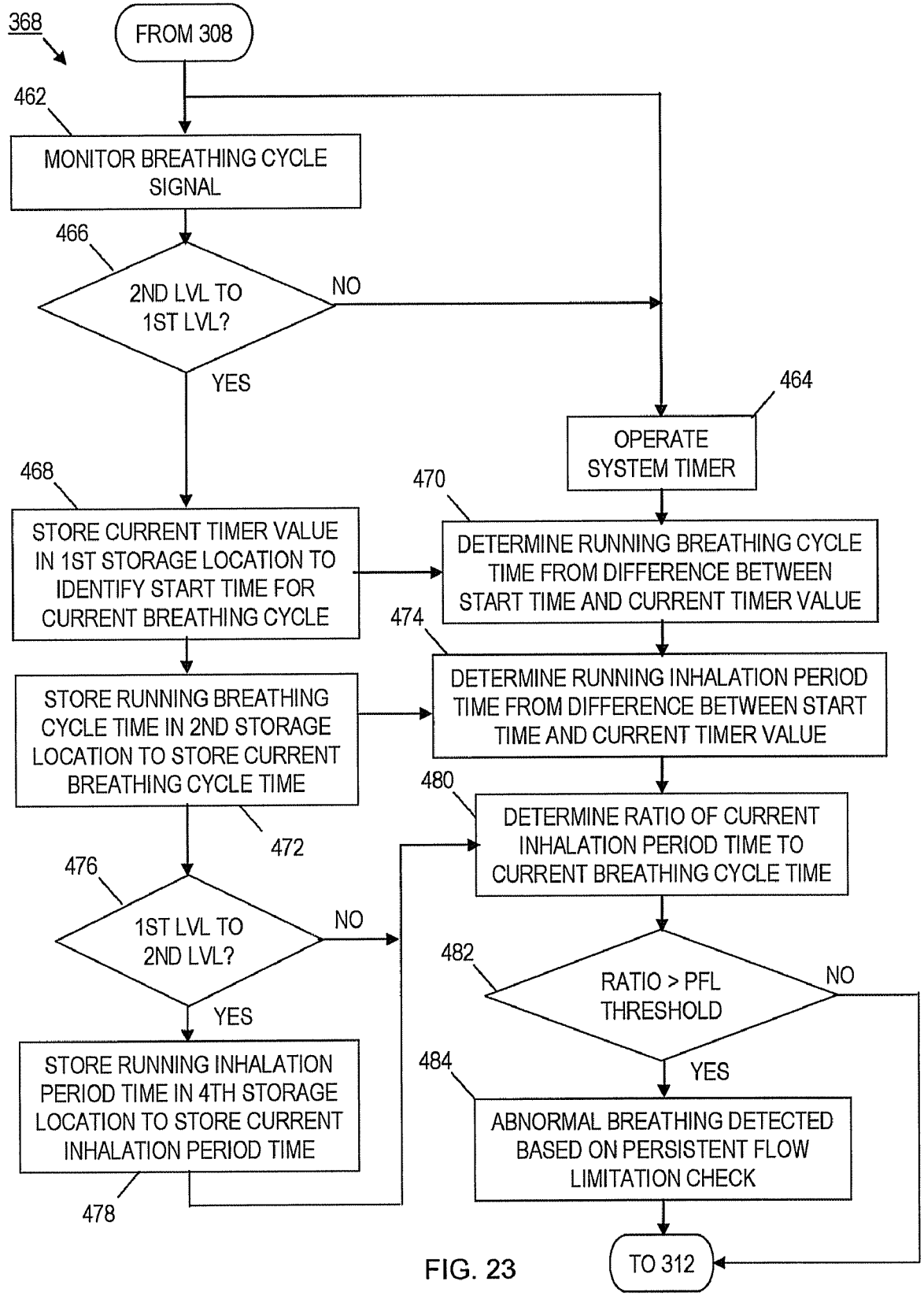

FIG. 23 is a flow chart of an embodiment of an exemplary process for performing a persistent flow limitation (PFL) check.

Figure 24:
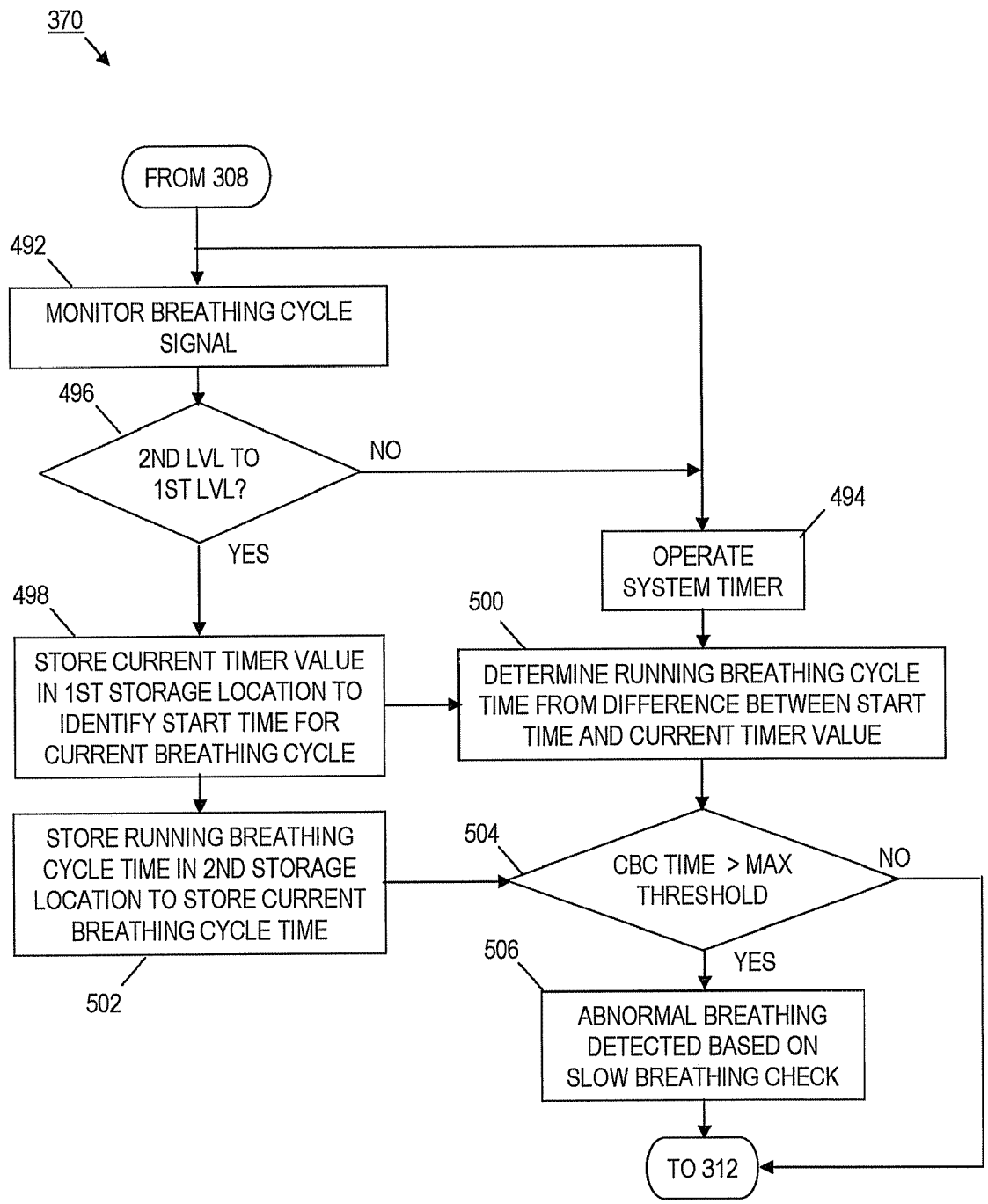

FIG. 24 is a flow chart of an embodiment of an exemplary process for performing a slow breathing check.

Figure 25:
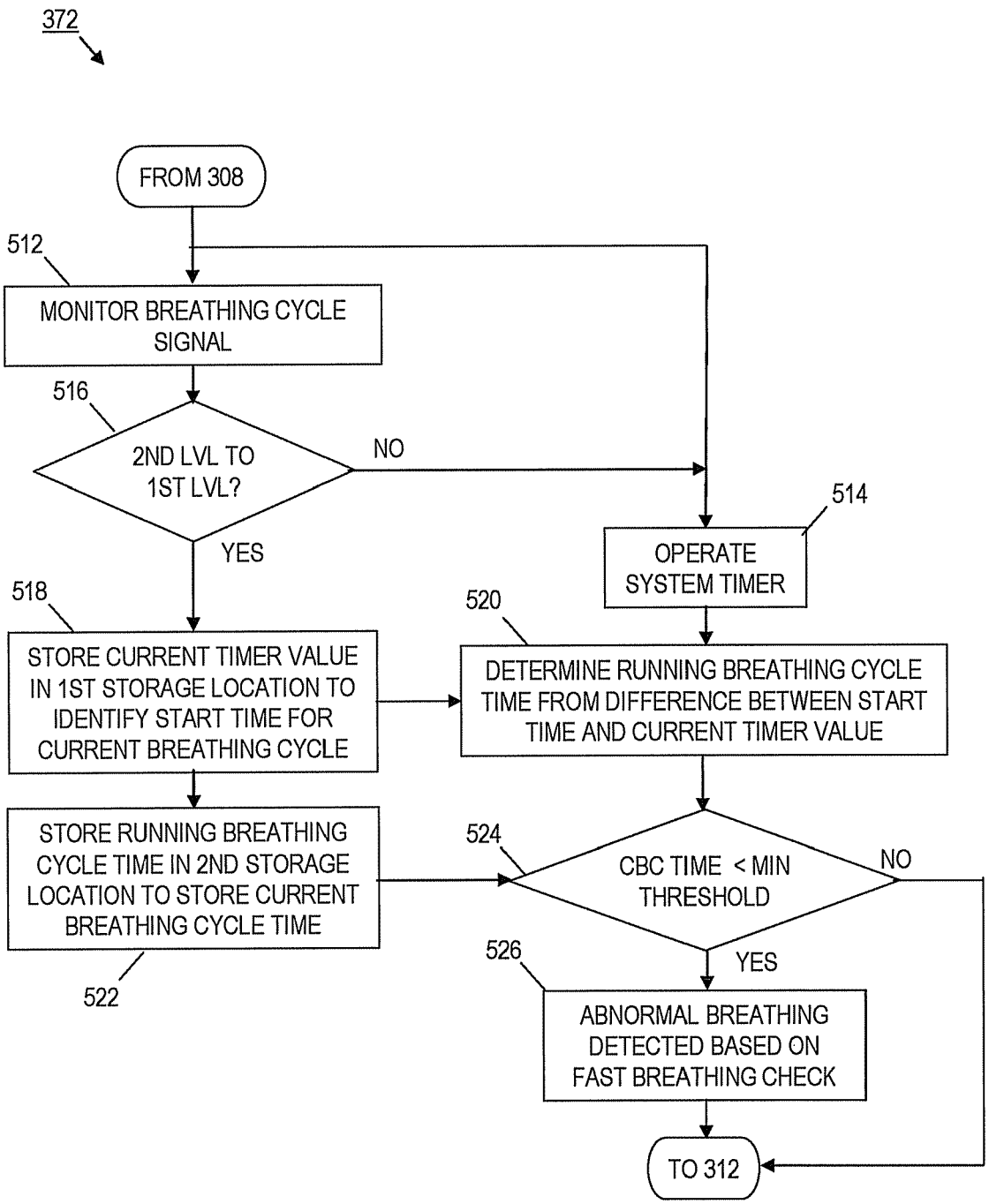

FIG. 25 is a flow chart of an embodiment of an exemplary process for performing a fast breathing check.

Figure 26:
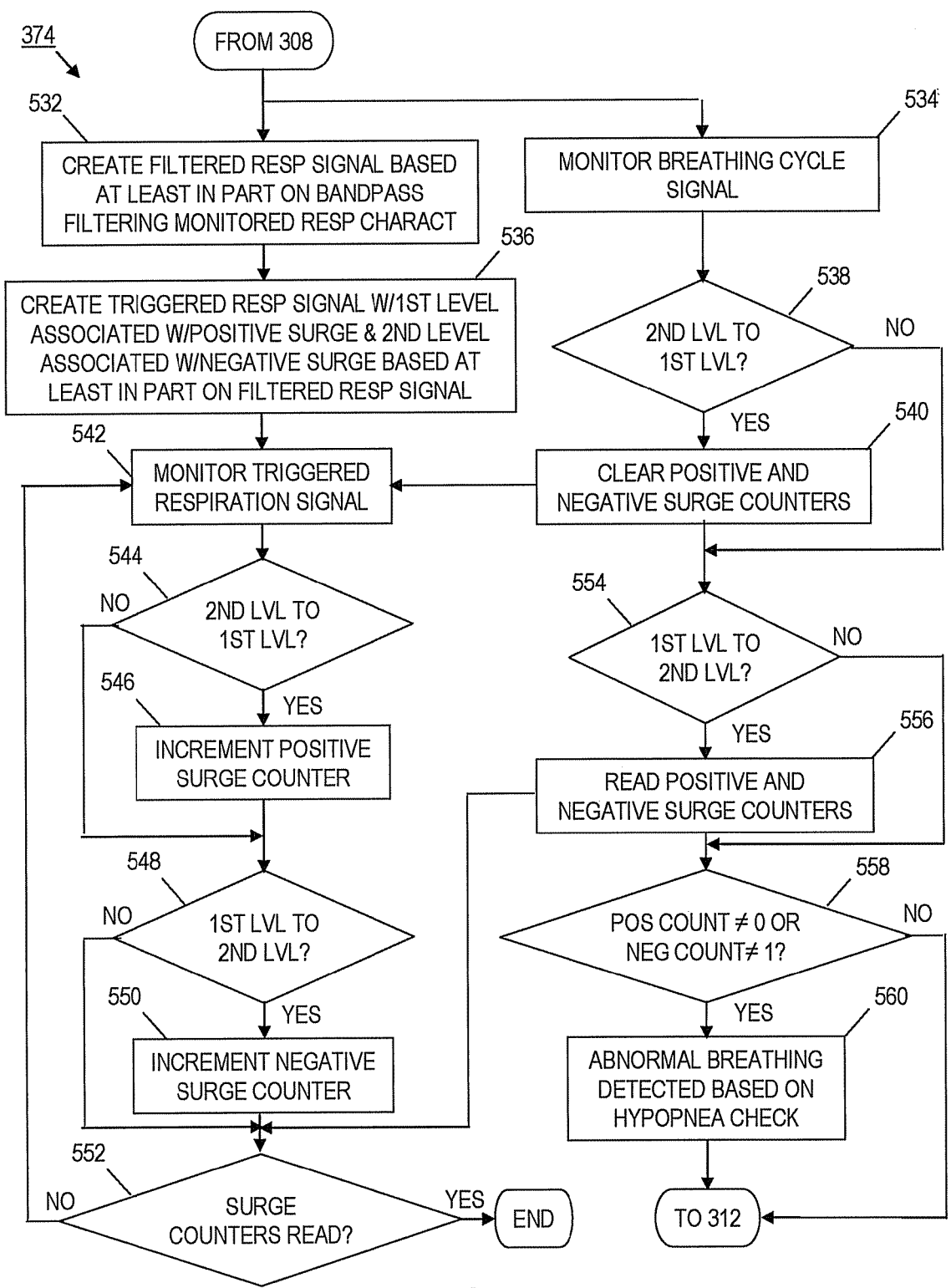

FIG. 26 is a flow chart of an embodiment of an exemplary process for performing a hypopnea check.

Figure 27:
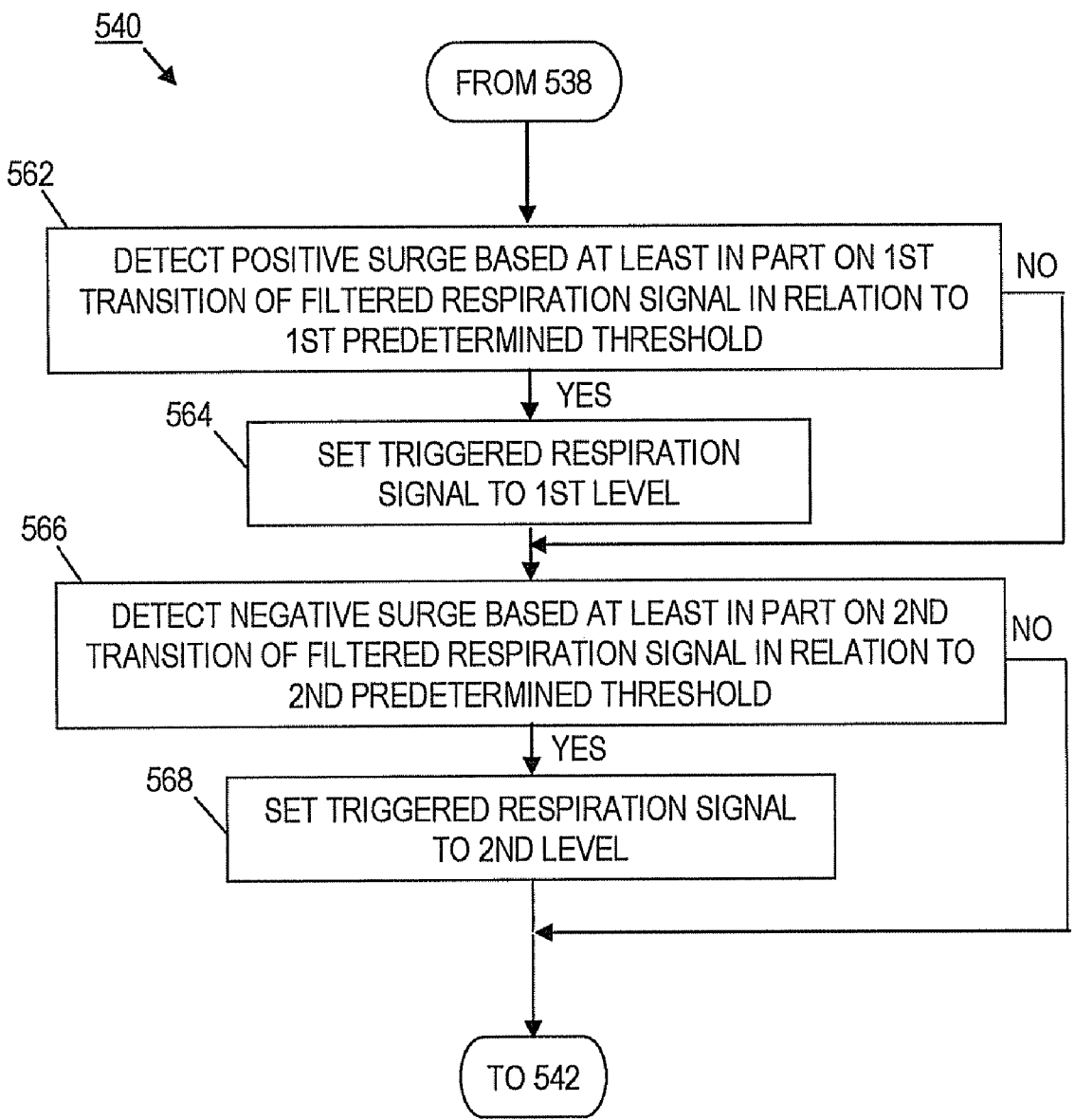

FIG. 27 is a flow chart of an embodiment of an exemplary process for generating a triggered respiration signal.

Figure 28:
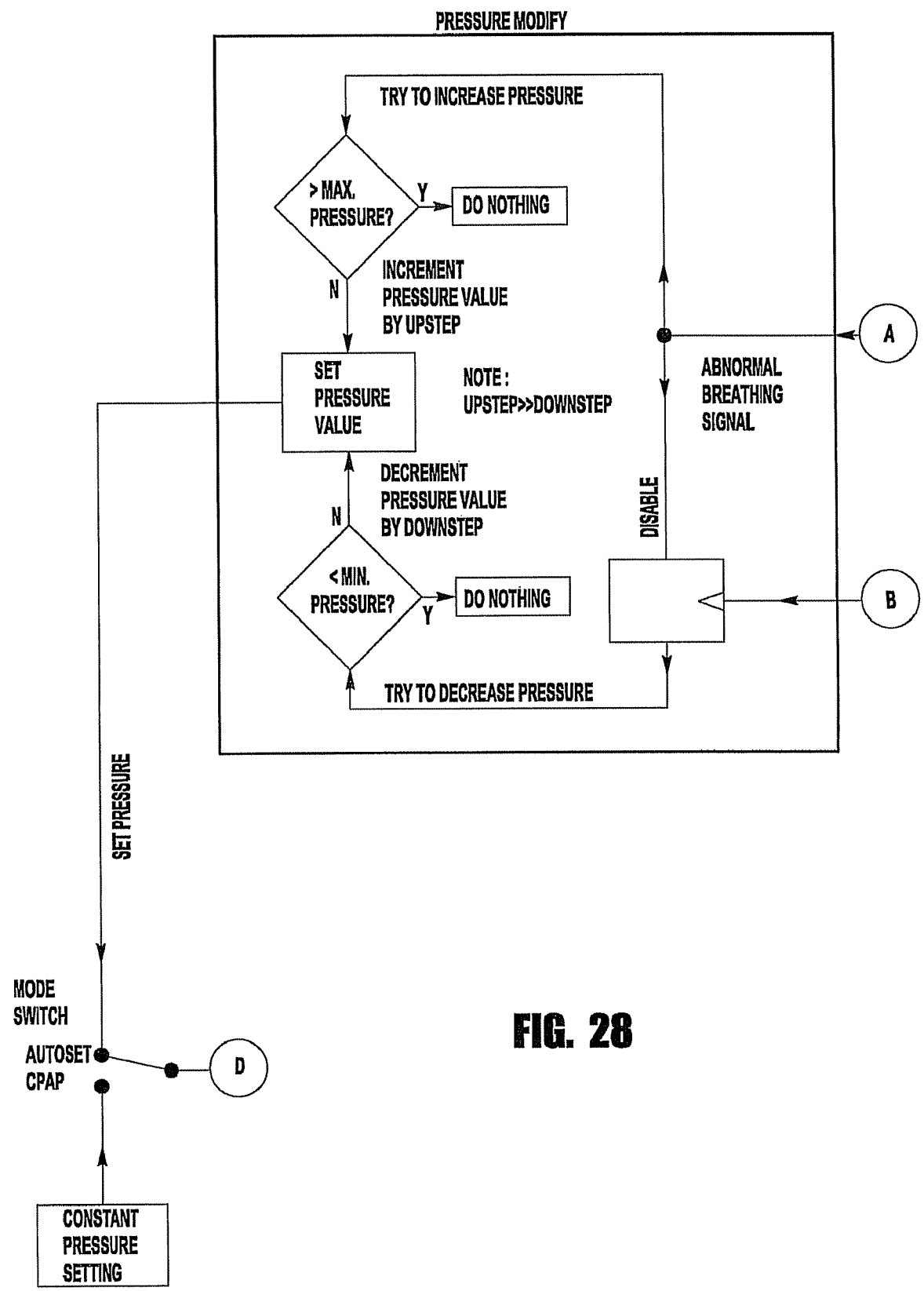

FIG. 28 is a block diagram of another embodiment of an exemplary PAP device.

Figure 29:
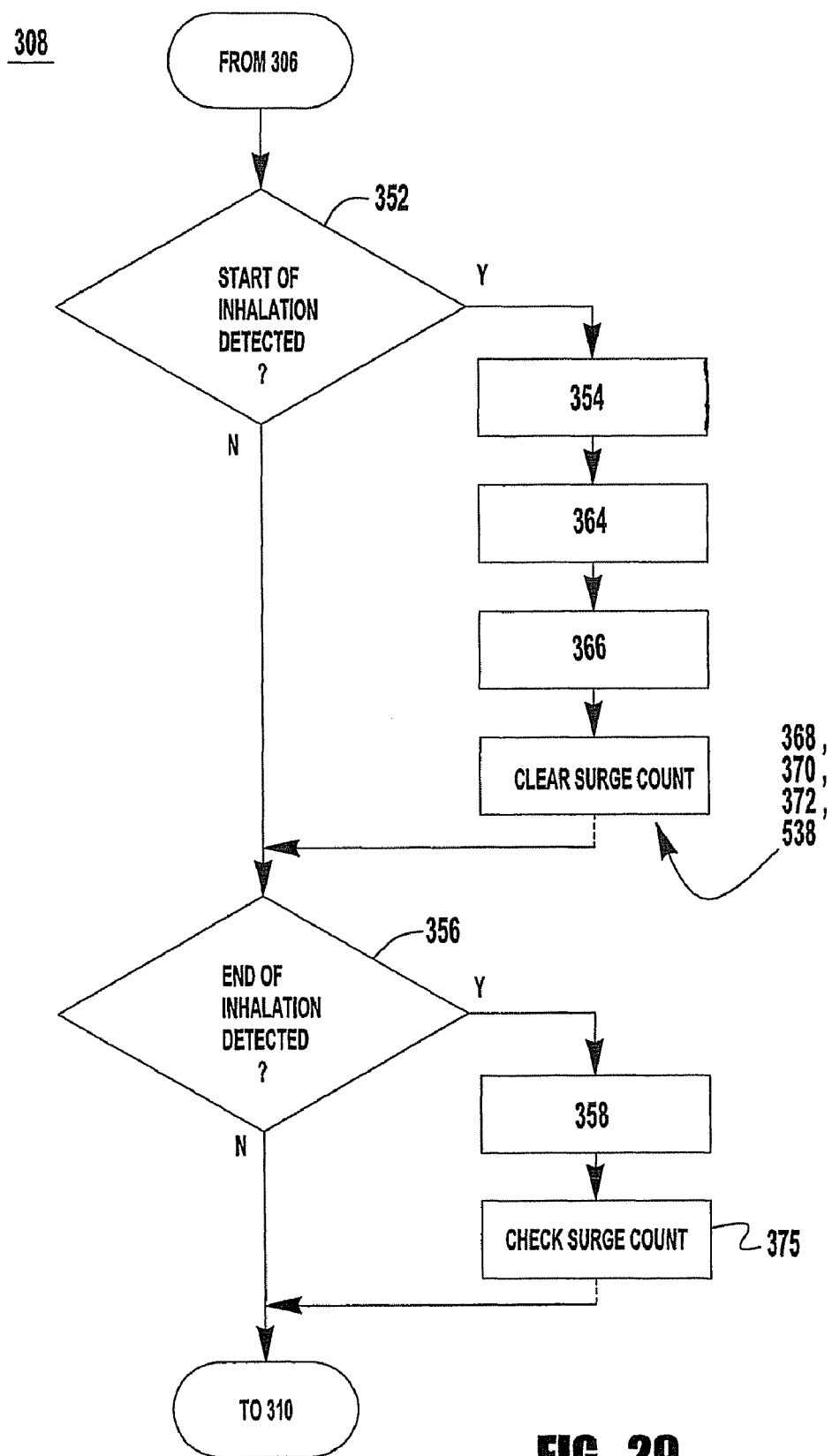

FIG. 29 is a flow chart of another embodiment of an exemplary process for generating a breathing cycle signal.

Figure 30:
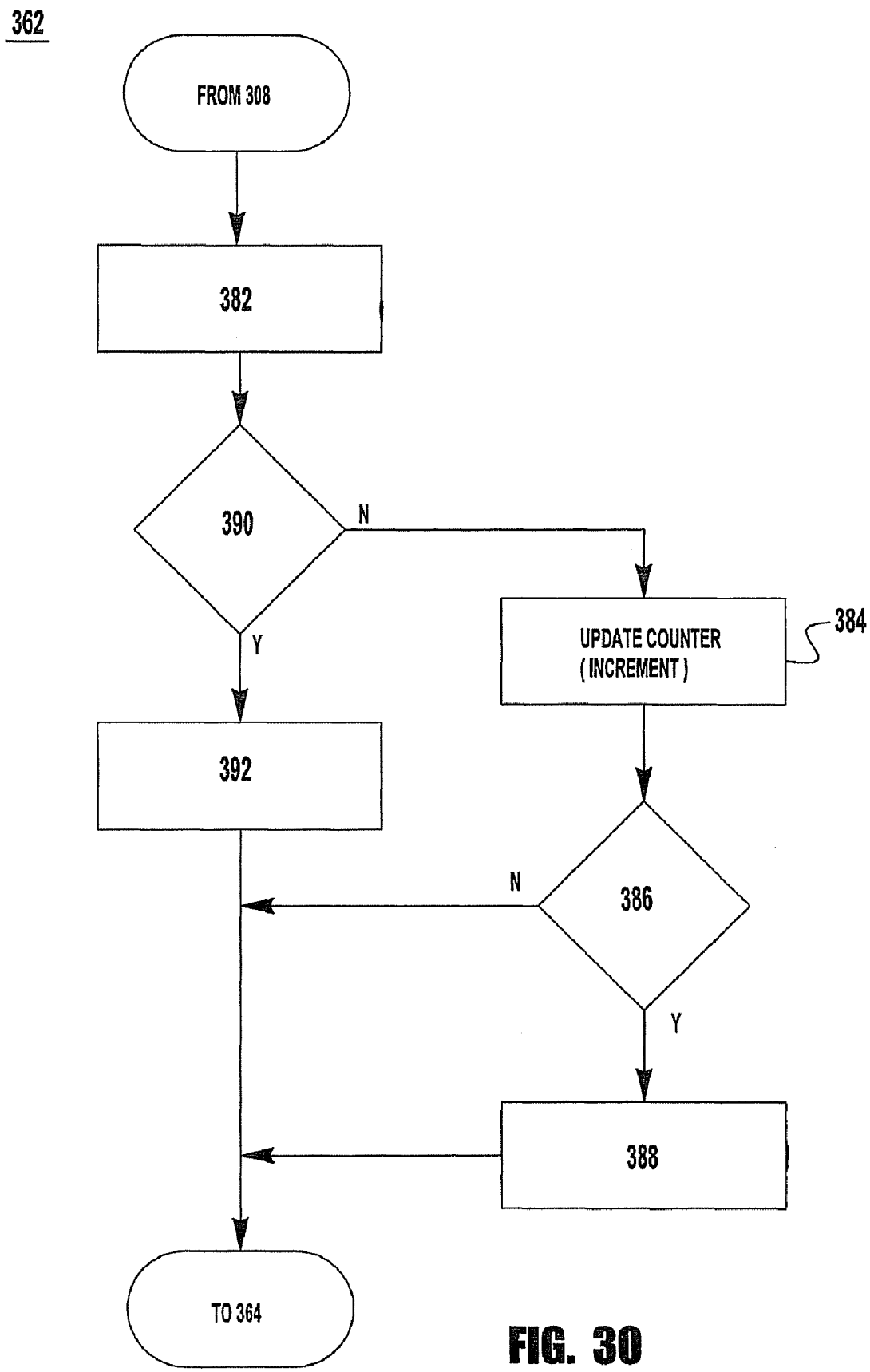

FIG. 30 is a flow chart of another embodiment of an exemplary process for performing an apnea check.

Figure 31:
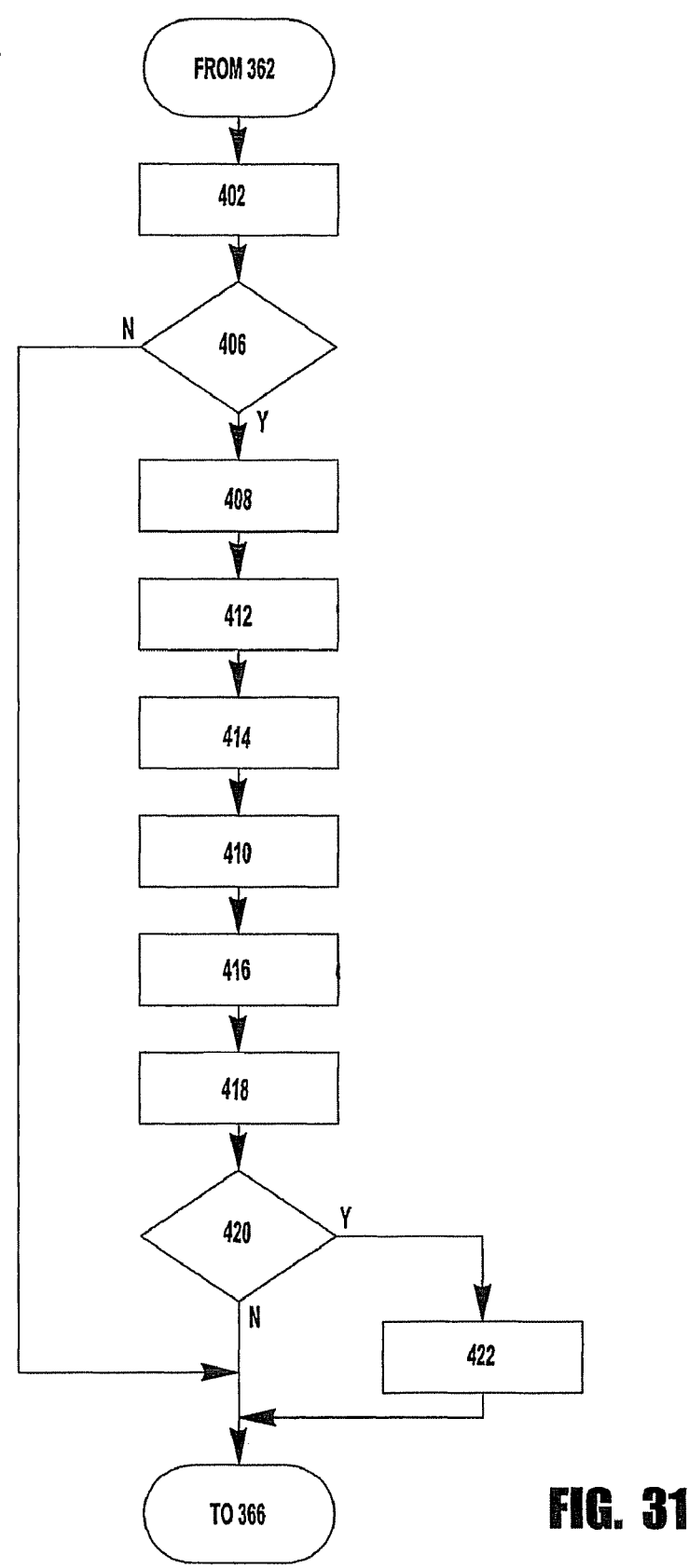

FIG. 31 is a flow chart of another embodiment of an exemplary process for performing an irregular breathing cycle check.

Figure 32:
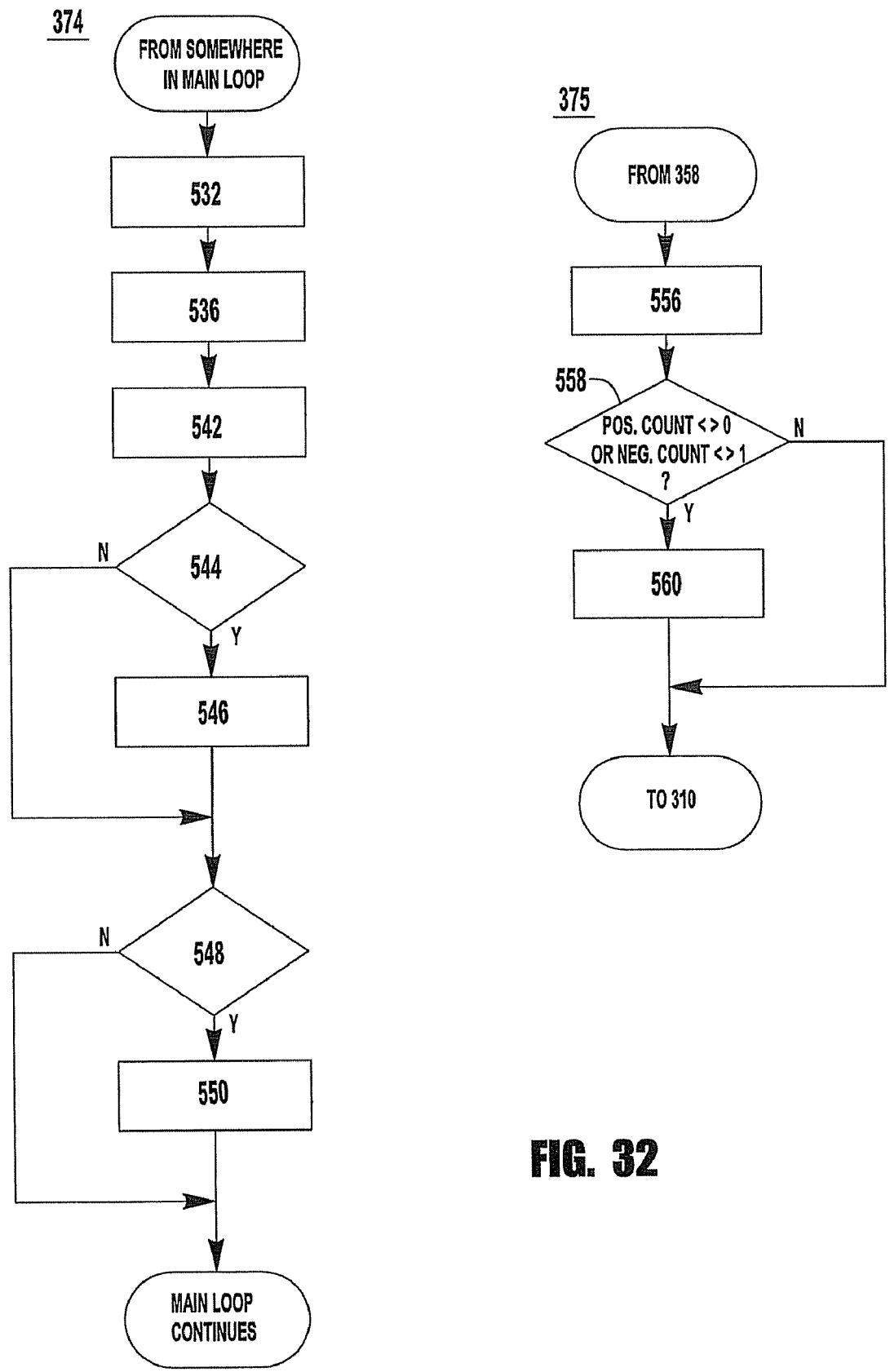

FIG. 32 is a flow chart of another embodiment of an exemplary process for performing a hypopnea check.

Figure 33:
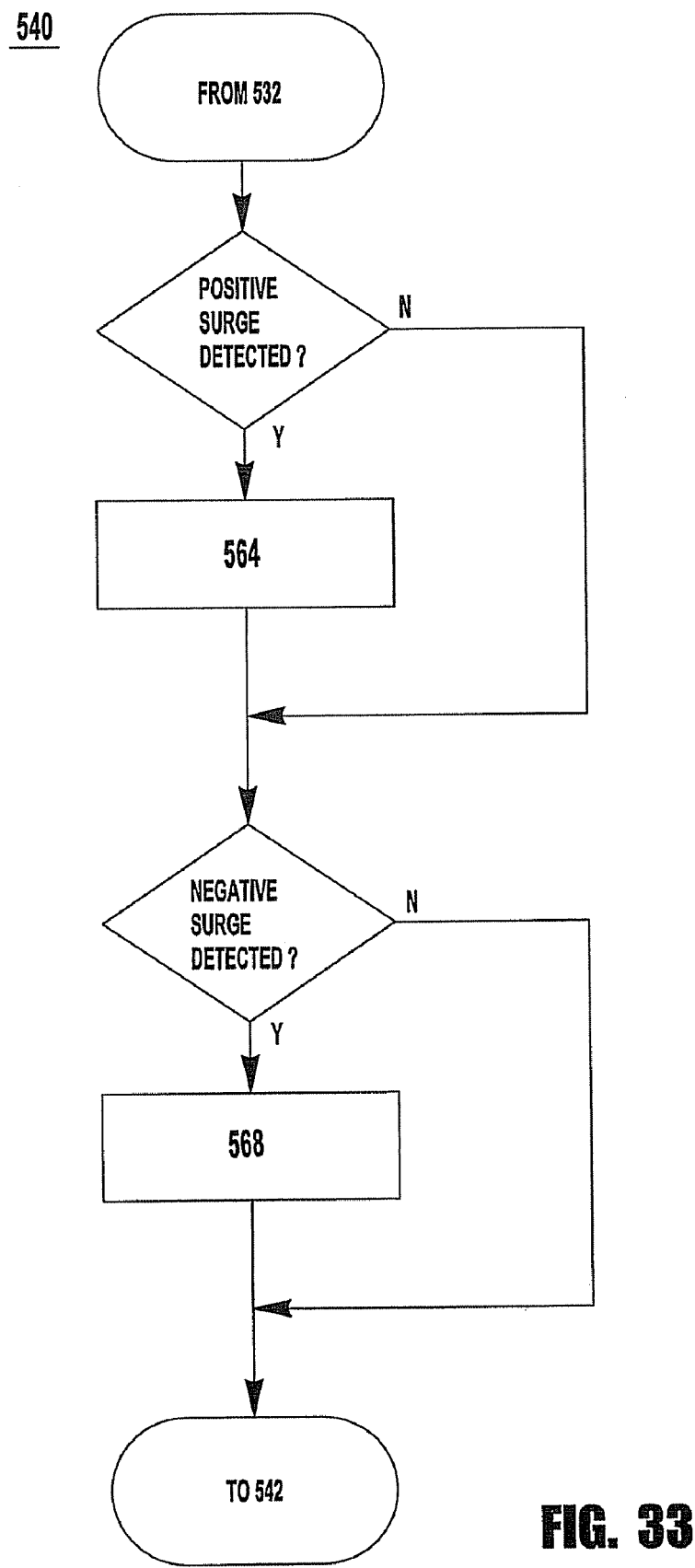

FIG. 33 is a flow chart of another embodiment of an exemplary process for generating a triggered respiration signal.

Figure 34:
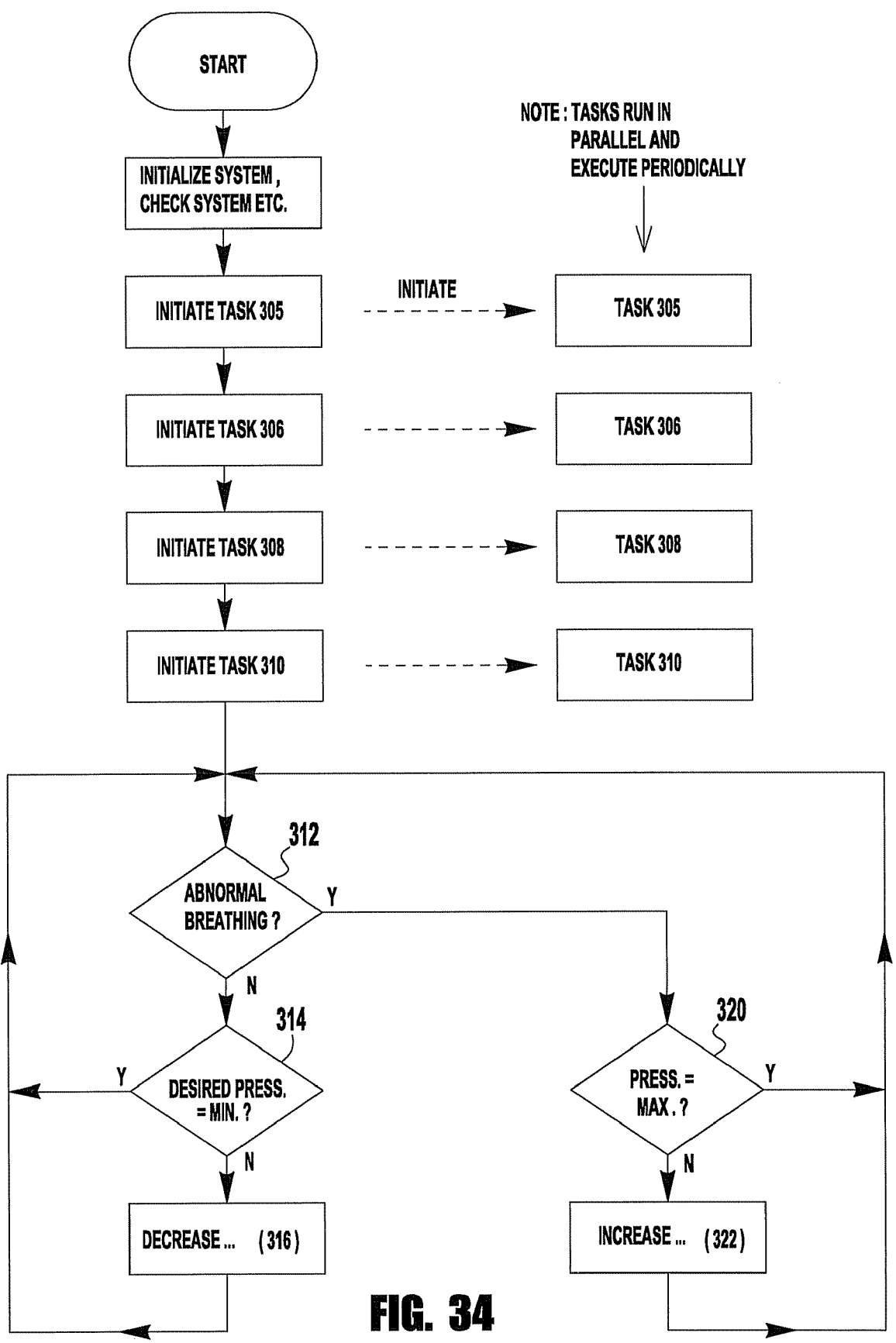

FIG. 34 is a flow chart of another embodiment of an exemplary process for adjusting a desired pressure in a PAP device.

Figure 35:
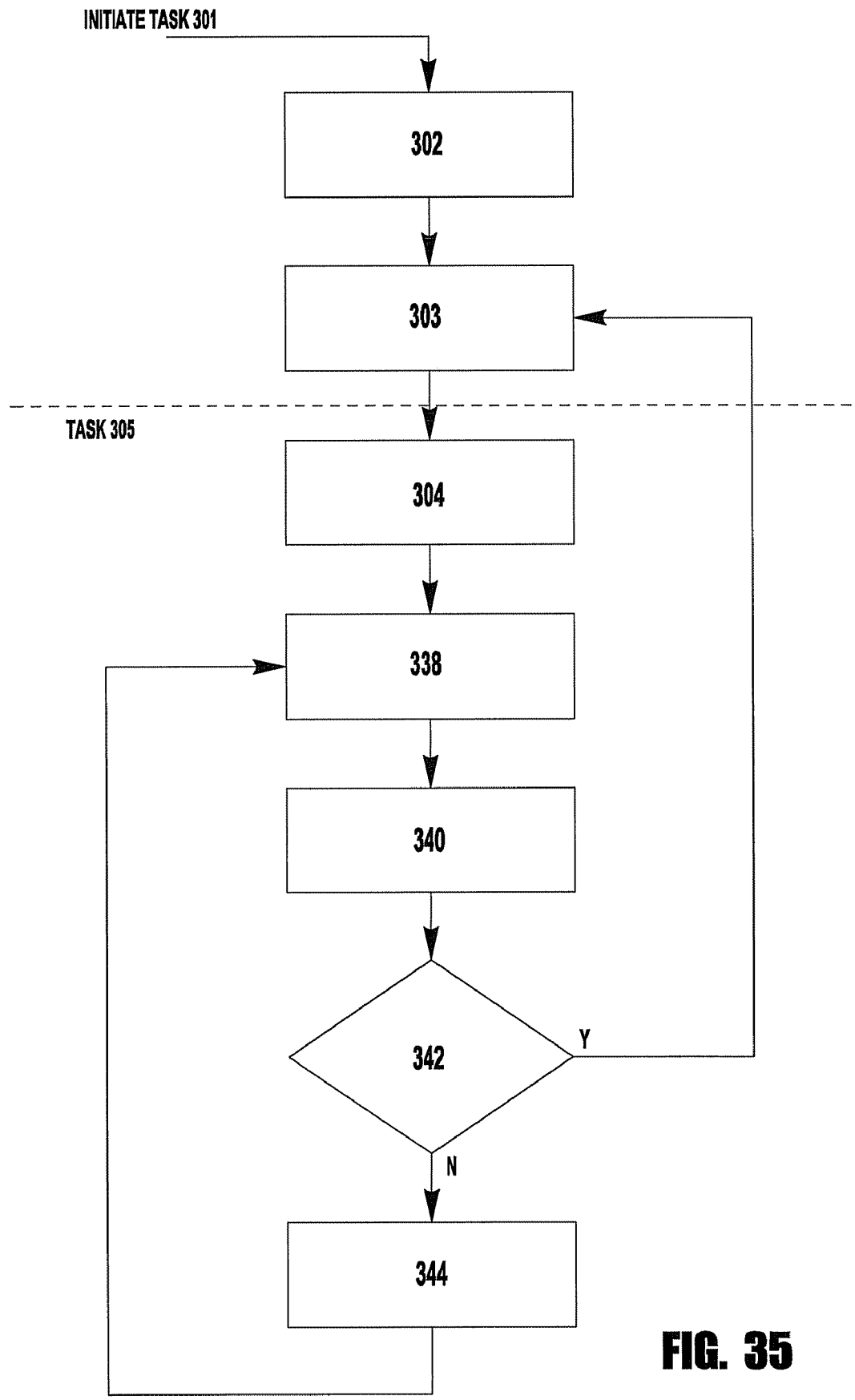

FIG. 35 is a flow chart of another embodiment of an exemplary process for providing a breathing gas to a patient based on a desired pressure.

Figure 36:
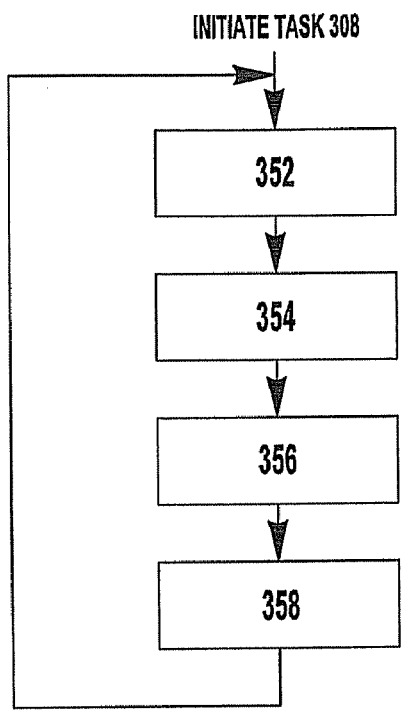

FIG. 36 is a flow chart of another embodiment of an exemplary process for generating a breathing cycle signal.

Figure 37:
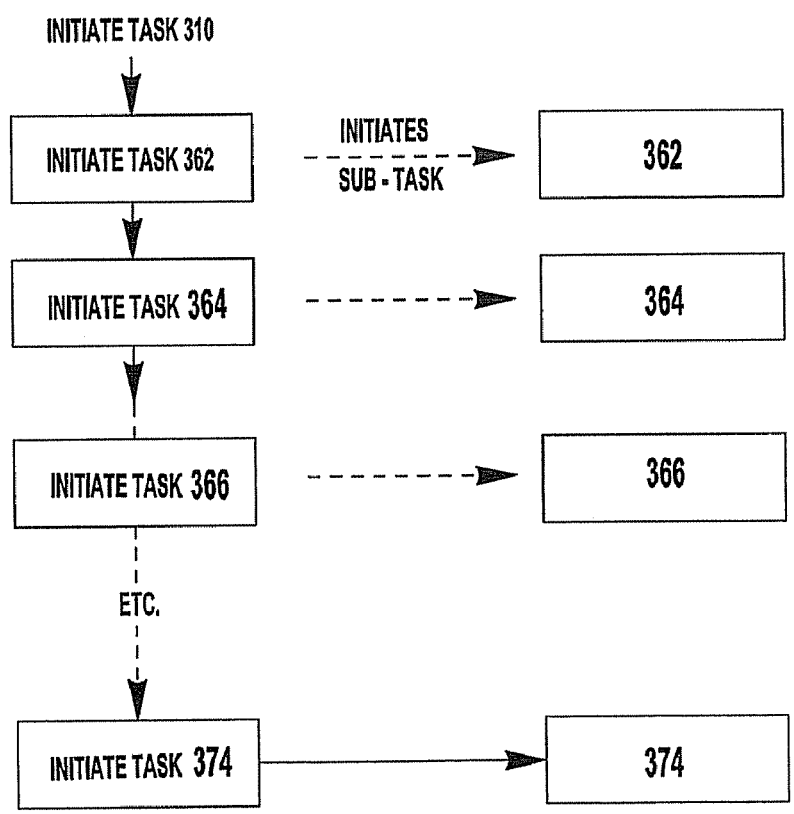

FIG. 37 is a flow chart of another embodiment of an exemplary process for performing one or more abnormal breathing checks.

Figure 38:
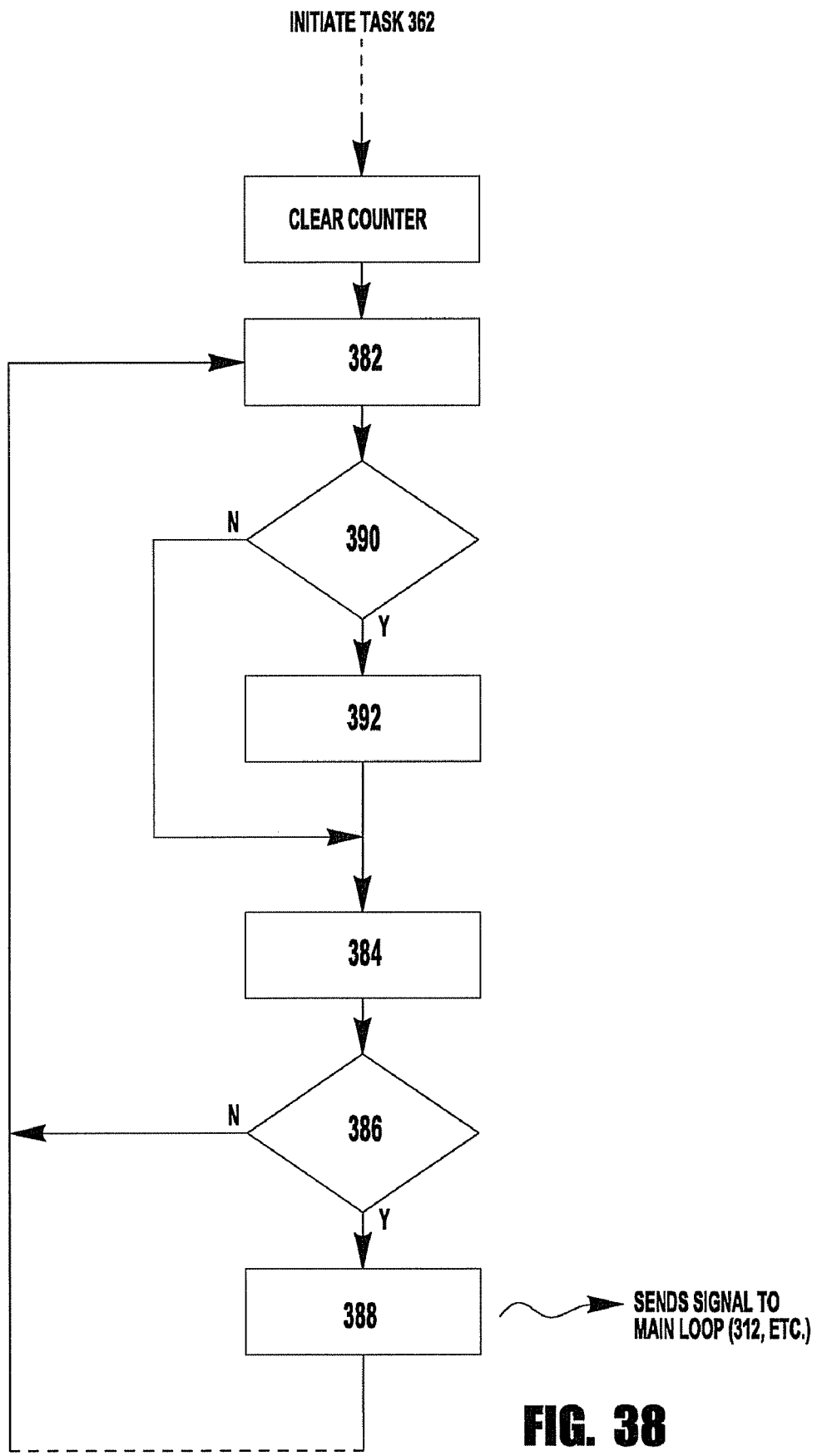

FIG. 38 is a flow chart of another embodiment of an exemplary process for performing an apnea check.

Figure 39:
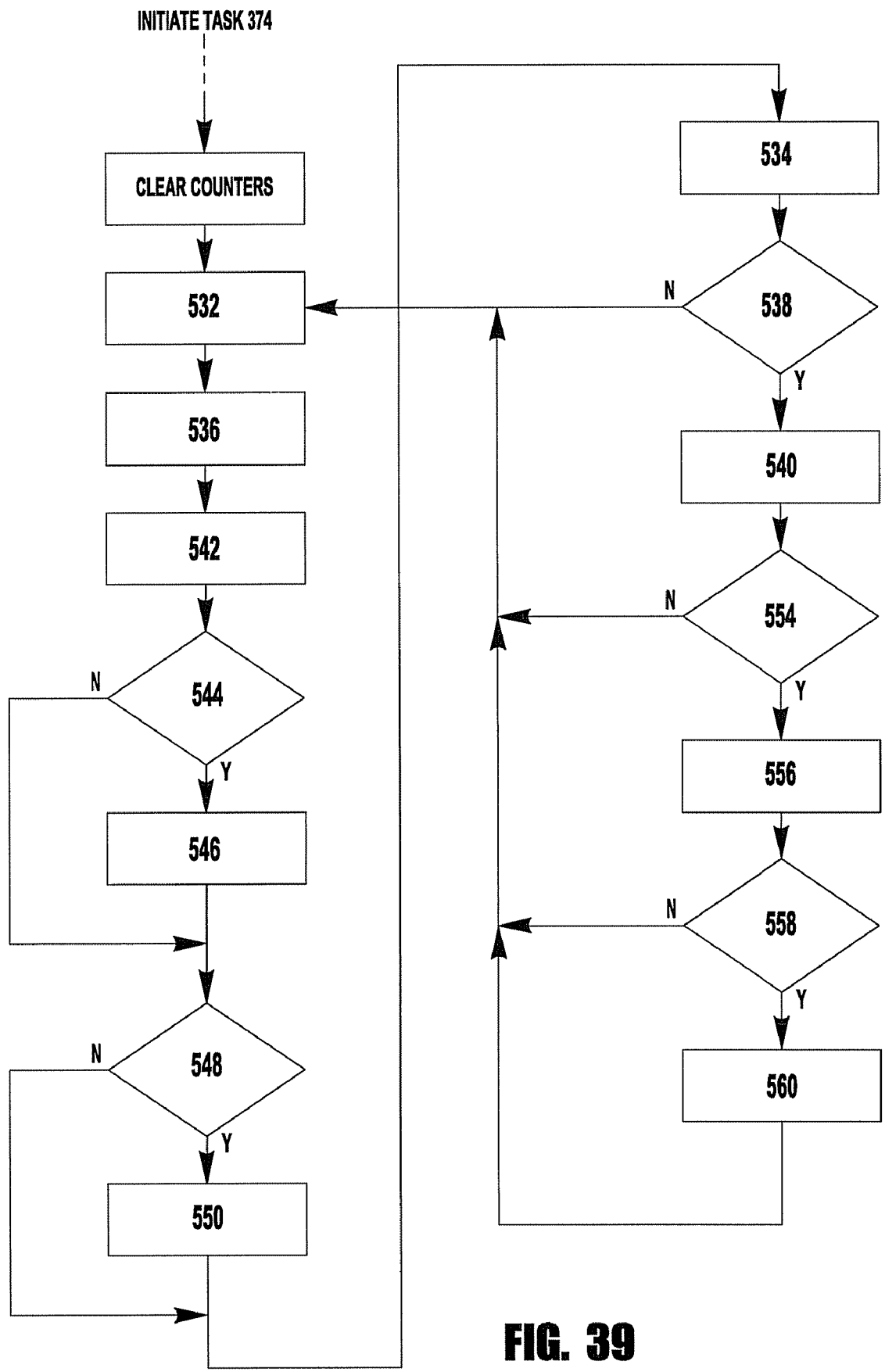

FIG. 39 is a flow chart of another embodiment of an exemplary process for performing a hypopnea check.

DESCRIPTION

The following paragraphs include definitions of exemplary terms used within this disclosure. Except where noted otherwise, variants of all terms, including singular forms, plural forms, and other affixed forms, fall within each exemplary term meaning. Except where noted otherwise, capitalized and non-capitalized forms of all terms fall within each meaning.

"Circuit," as used herein includes, but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or another programmed logic device. A circuit may also be fully embodied as software. Additionally, a circuit may include a sensor, detector, or emitter/detector combination. As used herein, "circuit" is considered synonymous with "logic."

"Comprising," "containing," "having," and "including," as used herein, except where noted otherwise, are synonymous and open-ended. In other words, usage of any of these terms (or variants thereof) does not exclude one or more additional elements or method steps from being added in combination with one or more delineated elements or method steps.

"Computer component," as used herein includes, but is not limited to, a computer-related entity, either hardware, firmware, software, a combination thereof, or software in execution. For example, a computer component can be, but is not limited to being, a processor, an object, an executable, a process running on a processor, a thread of execution, a program and a computer. By way of illustration, both an application running on a server and the server can be computer components. One or more computer components can reside within a process or thread of execution and a computer component can be localized on one computer or distributed between two or more computers.

"Computer communication," as used herein includes, but is not limited to, a communication between two or more computer components and can be, for example, a network transfer, a file transfer, an applet transfer, an email, a hypertext transfer protocol (HTTP) message, a datagram, an object transfer, a binary large object (BLOB) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, and so on.

"Controller," as used herein includes, but is not limited to, any circuit or device that coordinates and controls the operation of one or more input or output devices. For example, a controller can include a device having one or more processors, microprocessors, or central processing units (CPUs) capable of being programmed to perform input or output functions.

"Logic," as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software. Additionally, logic may include a sensor, detector, or emitter/detector combination. As used herein, "logic" is considered synonymous with "circuit."

"Measurement," as used herein includes, but is not limited to, an extent, magnitude, size, capacity, amount, dimension, characteristic, or quantity ascertained by estimating or appraising a property, characteristic, condition, criterion, or other metric. Example measurements may be provided, but such examples are not intended to limit the scope of measurements that the systems and methods described herein can employ.

"Operable connection," (or a connection by which entities are "operably connected"), as used herein includes, but is not limited to, a connection in which signals, physical communication flow, or logical communication flow may be sent or received. Usually, an operable connection includes a physical interface, an electrical interface, or a data interface, but an operable connection may include differing combinations of these or other types of connections sufficient to allow operable control.

"Operative communication," as used herein includes, but is not limited to, a communicative relationship between devices, logic, or circuits, including mechanical and pneumatic relationships. Direct and indirect electrical, electromagnetic, and optical connections are examples of connections that facilitate operative communications. Linkages, gears, chains, belts, push rods, cams, keys, attaching hardware, and other components contributing to mechanical relations between items are examples of components facilitating operative communications. Pneumatic devices and interconnecting pneumatic tubing may also contribute to operative communications. Two devices are in operative communication if an action from one causes an effect in the other, regardless of whether the action is modified by some other device. For example, two devices separated by one or more of the following: i) amplifiers, ii) filters, iii) transformers, iv) optical isolators, v) digital or analog buffers, vi) analog integrators, vii) other electronic circuitry, viii) fiber optic transceivers, ix) Bluetooth communications links, x) 802.11 communications links, xi) satellite communication links, and xii) other wireless communication links. As another example, an electromagnetic sensor is in operative communication with a signal if it receives electromagnetic radiation from the signal. As a final example, two devices not directly connected to each other, but both capable of interfacing with a third device, e.g., a central processing unit (CPU), are in operative communication.

"Or," as used herein, except where noted otherwise, is inclusive, rather than exclusive. In other words, "or" is used to describe a list of alternative things in which one may choose one option or any combination of alternative options. For example, "A or B" means "A or B or both" and "A, B, or C" means "A, B, or C, in any combination or permutation." If "or" is used to indicate an exclusive choice of alternatives or if there is any limitation on combinations of alternatives, the list of alternatives specifically indicates that choices are exclusive or that certain combinations are not included. For example, "A or B, but not both" is used to indicate use of an exclusive "or" condition. Similarly, "A, B, or C, but no combinations" and "A, B, or C, but not the combination of A, B, and C" are examples where certain combinations of alternatives are not included in the choices associated with the list.

"Processor," as used herein includes, but is not limited to, one or more of virtually any number of processor systems or stand-alone processors, such as microprocessors, microcontrollers, central processing units (CPUs), distributed processors, paired processors, and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software," as used herein includes, but is not limited to, one or more computer readable or executable instructions that cause a computer or another electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system, or other types of executable instructions. It will be appreciated by one of ordinary skill in the art that the form of software is dependent on, for example, requirements of a desired application, the environment it runs on, or the desires of a designer/programmer or the like.

"Software component," as used herein includes, but is not limited to, a collection of one or more computer readable or executable instructions that cause a computer or other electronic device to perform functions, actions or behave in a desired manner. The instructions may be embodied in various forms like routines, algorithms, modules, methods, threads, or programs. Software components may be implemented in a variety of executable or loadable forms including, but not limited to, a stand-alone program, a servelet, an applet, instructions stored in a memory, and the like. Software components can be embodied in a single computer component or can be distributed between computer components.

The following table includes long form definitions of exemplary acronyms used within this disclosure. Except where noted otherwise, variants of all acronyms, including singular forms, plural forms, and other affixed forms, fall within each exemplary acronym meaning. Except where noted otherwise, capitalized and non-capitalized forms of all acronyms fall within each meaning.

| Acronym | Long Form |
|---|---|
| ADC | Analog-to-digital |
| ASIC | Application specific integrated circuit |
| BLOB | Binary large object |
| BiPAP | Bi-level positive airway pressure |
| $CO_2$ | Carbon dioxide |
| CPAP | Continuous positive airway pressure |
| CPU | Central processing unit |
| DAC | Digital-to-analog |
| DSP | Digital signal processor |
| EPROM | Erasable programmable read-only memory |
| HTTP | Hypertext transfer protocol |
| IR | Infrared |
| LAN | Local area network |
| LCD | Liquid crystal display |
| LED | Light-emitting diode |
| $O_2$ | Oxygen |
| PAP | Positive airway pressure |
| PFL | Persistent flow limitation |
| PPAP | Proportional positive airway pressure |
| PROM | Programmable read-only memory |
| PSG | Polysomnogram |
| RAM | Random access memory |
| ROM | Read-only memory |
| SoftX ™ | Softened exhalation pressure |
| WAN | Wide area network |

Figure 1:
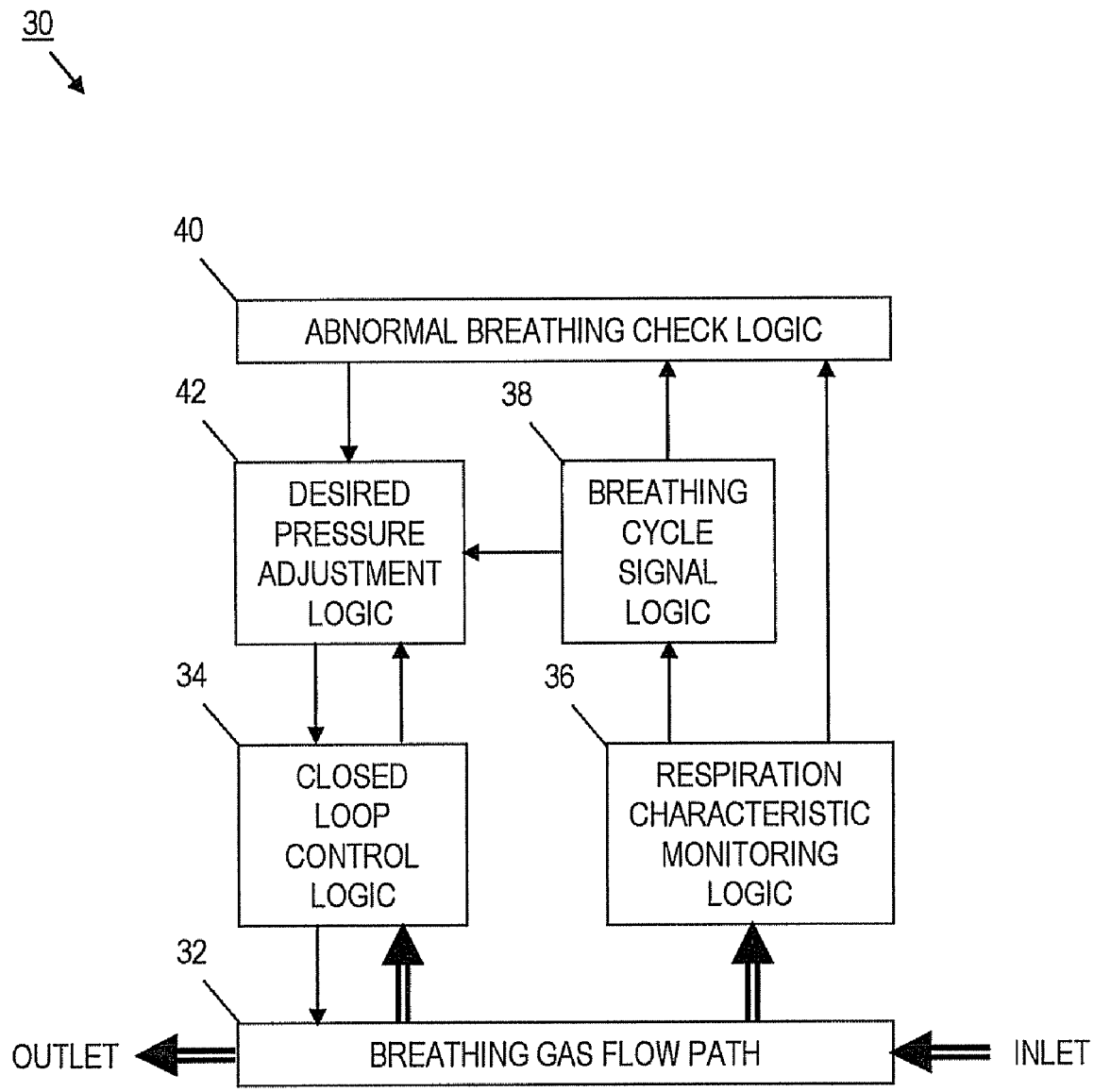
FIG. 1 is a block diagram of an embodiment of an exemplary positive airway pressure (PAP) device.

With reference to FIG. 1, an embodiment of an exemplary positive airway pressure (PAP) device 30 may include a breathing gas flow path 32, a closed loop control logic 34, a respiration characteristic monitoring logic 36, a breathing cycle signal logic 38, an abnormal breathing check logic 40, and a desired pressure adjustment logic 42. The PAP device 30, for example, may be configured as a CPAP device (i.e., standard CPAP, CPAP with SoftX™, etc.), a BiPAP device, a PPAP device, an auto-titrating PAP device, a ventilator device, a gas therapy device, an oxygen therapy device, or another type of PAP device.

The breathing gas flow path 32 may be in operative communication with the closed loop control logic 34. The combination of the breathing gas flow path 32 and closed loop control logic 34 may be adapted to provide a breathing gas under positive pressure to a patient based at least in part on a current desired pressure. The breathing gas flow path 32 may receive the breathing gas via an inlet, pressurize the breathing gas, and provide the pressurized breathing gas to a patient via the outlet. The closed loop control logic 34 may control the pressure of the breathing gas provided to the patient via the breathing gas flow path 32 based on desired pressure information, for example, from the desired pressure adjustment logic 42 and detected pressure information, for example, from the breathing gas flow path 32. In the alternative, or in addition, the closed loop control logic 34 may control a breathing gas valve or vent to adjust the breathing gas pressure provided to the patient. The detected pressure information may be based on one or more characteristics of the breathing gas that are related to pressure. For example, pressure, flow, and flow rate are examples of such breathing gas characteristics.

The respiration characteristic monitoring logic 36 may be in operative communication with the breathing gas flow path 32 to monitor one or more characteristics related to the breathing gas that may be indicative of respiration (i.e., patient breathing). For example, pressure, flow, flow rate, temperature, humidity, oxygen ($O_2$), and carbon dioxide ($CO_2$) are characteristics of the breathing gas that may be indicative of respiration. Similarly, blower motor Hall effect, blower motor voltage or current, blower motor speed, breathing gas valve position, and breathing gas vent position are examples of characteristics associated with the PAP device 30 that are related to the breathing gas and may be indicative of respiration. Alternatively, the respiration characteristic monitoring logic 36 may monitor one or more patient physiological characteristics that may be indicative of respiration. For example, any of the characteristics monitored during a polysomnogram (PSG) (e.g., brain waves, electrical activity of muscles, eye movement, breathing rate, blood pressure, blood oxygen saturation, and heart rhythm) are examples of patient physiological characteristics that may be indicative of respiration. A PSG is a test that may be used to diagnose sleep apnea. Any combination of such breathing gas characteristics, PAP device characteristics, and patient physiological characteristics may be monitored.

Monitoring one or more characteristics that are indicative of respiration provides corresponding monitored signals. The breathing cycle signal logic 38 may be in operative communication with the respiration characteristic monitoring logic 36 to create a breathing cycle signal having a first level associated with inhalation and a second level, different from the first level, associated with exhalation. The breathing cycle signal may be based at least in part on the monitored respiration characteristic(s). In one embodiment, the first and second levels of the breathing cycle signal may correspond to voltage levels associated with opposing digital signal logic levels.

The abnormal breathing check logic 40 may be in operative communication with the breathing cycle signal logic 38 to perform at least one abnormal breathing check based at least in part on the breathing cycle signal. The abnormal breathing check logic 40 may also (or alternatively) be in operative communication with the respiration characteristic monitoring logic 36 to perform at least one abnormal breathing check based at least in part on any one or more of the monitored respiration characteristics. The desired pressure adjustment logic 42 may be in operative communication with the abnormal breathing check logic 40, breathing cycle signal logic 38, and closed loop control logic 34. The desired pressure adjustment logic 42 alters the PAP device desired pressure in response to one or more parameters. For example, the desired pressure adjustment logic 42 may increase the current desired pressure by a first increment (e.g., a pressure increment of +0.36 cm $H_2O$ per breath or some other value) until a maximum desired pressure is reached if abnormal breathing is detected. Conversely, for example, the desired pressure adjustment logic may decrease the current desired pressure by a second increment (e.g., a pressure decrement of −0.06 cm $H_2O$ per breath or some other value) until a minimum desired pressure is reached if abnormal breathing is not detected.

As an example, the first increment, which is related to increasing desired pressure, may be higher than the second increment, which is related to decreasing desired pressure.

However, other relationships between the first and second increments are possible. Additionally, in other embodiments, the first or second increments may be variable. For example, the first or second increments may be determined based on i) the type of abnormal breathing detected, ii) the difference between the current desired pressure and the maximum desired, iii) factors associated with the patient's normal breathing pattern, iv) factors associated with the patient's history for abnormal breathing, v) factors associated with the patient's prescription or treatment plan, or vi) any combination thereof.

Similarly, the minimum and maximum desired pressures may adjustable and may be determined based on i) the type of abnormal breathing detected, ii) the difference between the current desired pressure and the maximum desired, iii) factors associated with the patient's normal breathing pattern, iv) factors associated with the patient's history for abnormal breathing, v) factors associated with the patient's prescription or treatment plan, or vi) any combination thereof. In particular, the minimum desired pressure may be adjusted based on a recent abnormal breathing detection for the patient. For example, after abnormal breathing is detected, the minimum desired pressure may be determined based on the pressure at which the abnormal breathing was detected plus an offset to predict a new minimum desired pressure value that may avoid a recurrence of the recent abnormal breathing condition. After breathing is normal for a sufficient period of time, the minimum desired pressure may be gradually or incrementally reduced to a lower predetermined level based on i) factors associated with the patient's normal breathing pattern, ii) factors associated with the patient's history for abnormal breathing, iii) factors associated with the patient's prescription or treatment plan, or iv) any combination thereof. The maximum desired pressure may be adjusted in similar fashion. However, an absolute maximum desired pressure based on known health and safety standards would establish an upper limit for the desired pressure that could not be exceeded.

In another embodiment, each incremental increasing or decreasing of the current desired pressure may be associated with transition of the breathing cycle signal from the second level to the first level or vice versa. Any of the aspects of FIG. 1 described above may be automated, semi-automated, or manual and may be implemented through hardware, software, firmware, or combinations thereof. Analog-to-digital conversions (ADCs) or digital-to-analog conversions (DACs) may be accomplished within components, such as sensors, input/output devices, or input/output ports of a controller or processor, particularly where software or firmware are used to implement certain aspects of FIG. 1.

Figure 2:
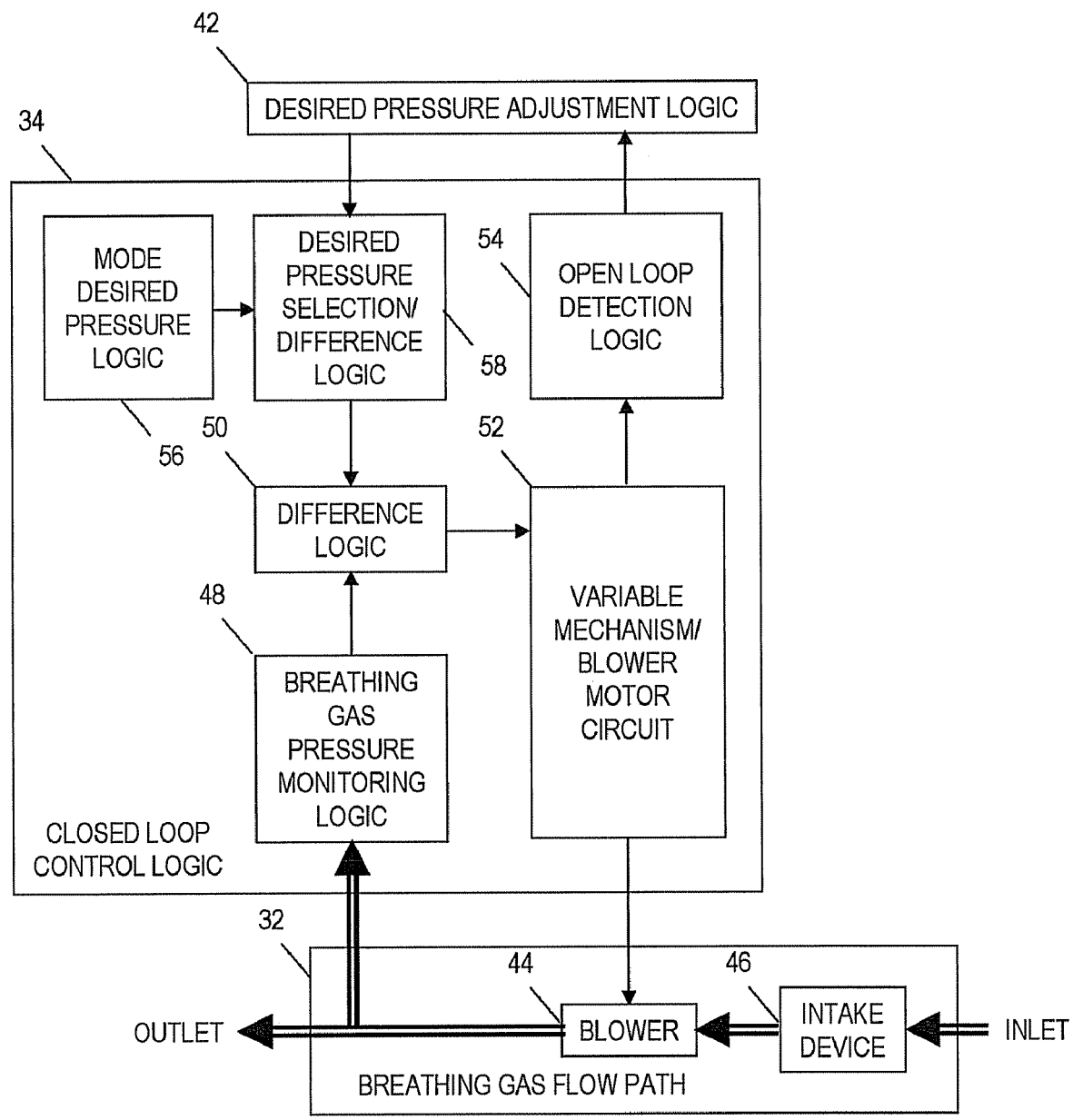
FIG. 2 is a block diagram of an exemplary PAP device with exemplary embodiments of a breathing gas flow path and a closed loop control logic.

With reference to FIG. 2, an embodiment of an exemplary breathing gas flow path 32 and an embodiment of an exemplary closed loop control logic 34 from the PAP device 30 (FIG. 1) are shown with the desired pressure adjustment logic 42. The breathing gas flow path 32 may include a blower 44 and an intake device 46. The blower 44 may be adapted to pressurize the breathing gas provided to the patient. The intake device 46 may provide filtering, silencing, or flow restriction, in any combination, at the inlet to the breathing gas flow path 32.

The closed loop control logic 34 may include a breathing gas pressure monitoring logic 48, a first difference logic 50, a variable mechanism/blower motor circuit 52, an optional open loop detection logic 54, an optional mode desired pressure logic 56, and a desired pressure selection/second difference logic 58. The breathing gas pressure monitoring logic 48 may be in operative communication with the breathing gas flow path 32 to monitor one or more characteristics of the breathing gas that are related to pressure. For example, pressure, flow, and flow rate are examples of such breathing gas characteristics. Monitoring one or more characteristics related to breathing gas pressure provides corresponding monitored signals. The first difference logic 50 may be in operative communication with the desired pressure adjustment logic 42 and the breathing gas pressure monitoring logic 48 to determine a difference between the current desired pressure and the monitored characteristic. The variable mechanism/blower motor circuit 52 may be in operative communication with the first difference logic 50 and the blower 44. A variable mechanism (e.g., variable speed blower motor, variable position breathing gas valve, variable position breathing gas vent, etc.) within the variable mechanism/blower motor circuit 52 may be adapted to change based at least in part on the difference between the current desired pressure and the monitored pressure characteristic to reduce the difference. Various types of control schemes may be implemented within the variable mechanism/blower motor circuit 52, such as PID control, PI control, PD control, etc.

Optional open loop detection logic 54 may be in operative communication with the variable mechanism/blower motor circuit 52 and the desired pressure adjustment logic 42 to determine if a runaway low pressure condition exists. If a runaway low pressure condition is detected, the current desired pressure may be set to a desired startup pressure. Alternatively, or additionally, a warning or alarm condition may be triggered by the runaway low pressure condition. In various embodiment, the alarm condition may initiate audible, visual, or tactile stimuli to the patient, initiate audible alarms, visual alarms, or messaging to a caretaker or healthcare provider, or any combination thereof.

Optional mode desired pressure logic 56 may be adapted to selectively identify a default desired pressure based at least in part on a currently-selected operating mode. For example, an operating mode may be selected with a specific pressure level prescribed for the patient. Moreover, certain devices may provide CPAP, CPAP with SoftX™, BiPAP, PPAP, or other types of operating modes in any combination and may allow selection of a specific operating mode prescribed for the patient. The desired pressure selection/second difference logic 58 may be in operative communication with the mode desired pressure selection logic 56, desired pressure adjustment logic 42, and first difference logic 50 to adjust the current desired pressure based at least in part on the currently-selected operating mode.

Optional mode desired pressure logic 56 may also be adapted to selectively identify a desired pressure profile based at least in part on the currently-selected operating mode. If so, the desired pressure selection/second difference logic 58 may also adjust the current desired pressure based at least in part on the desired pressure profile. In one embodiment, the desired pressure profile may correspond to a breathing cycle and may include a first desired pressure associated with at least a portion of inhalation and a second desired pressure associated with at least a portion of exhalation. In this embodiment, the second desired pressure is typically less than the first desired pressure. However, other relationships between the first and second desired pressures are also possible. Desired pressure profiles of this nature, for example, may be provided for operation of CPAP with SoftX™, BiPAP, and other PAP devices.

In another embodiment, the desired pressure profile may correspond to a ramp period and may include a first pressure associated with a time when the patient is presumed awake, a second pressure associated with a time when the patient is presumed to be asleep, and a ramp function to gradually adjust the desired pressure from the first pressure to the second pressure during the ramp period. In this embodiment, the first pressure is typically less than the second pressure. However, other relationships between the first and second pressures are also possible. Desired pressure profiles of this nature, for example, may be provided for operation of CPAP devices, as well as CPAP with SoftX™ and BiPAP devices. Additional types of desired pressure profiles and combinations of various types of desired pressure profiles are also envisioned. Any of the aspects of FIG. 2 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 2.

Figure 3:
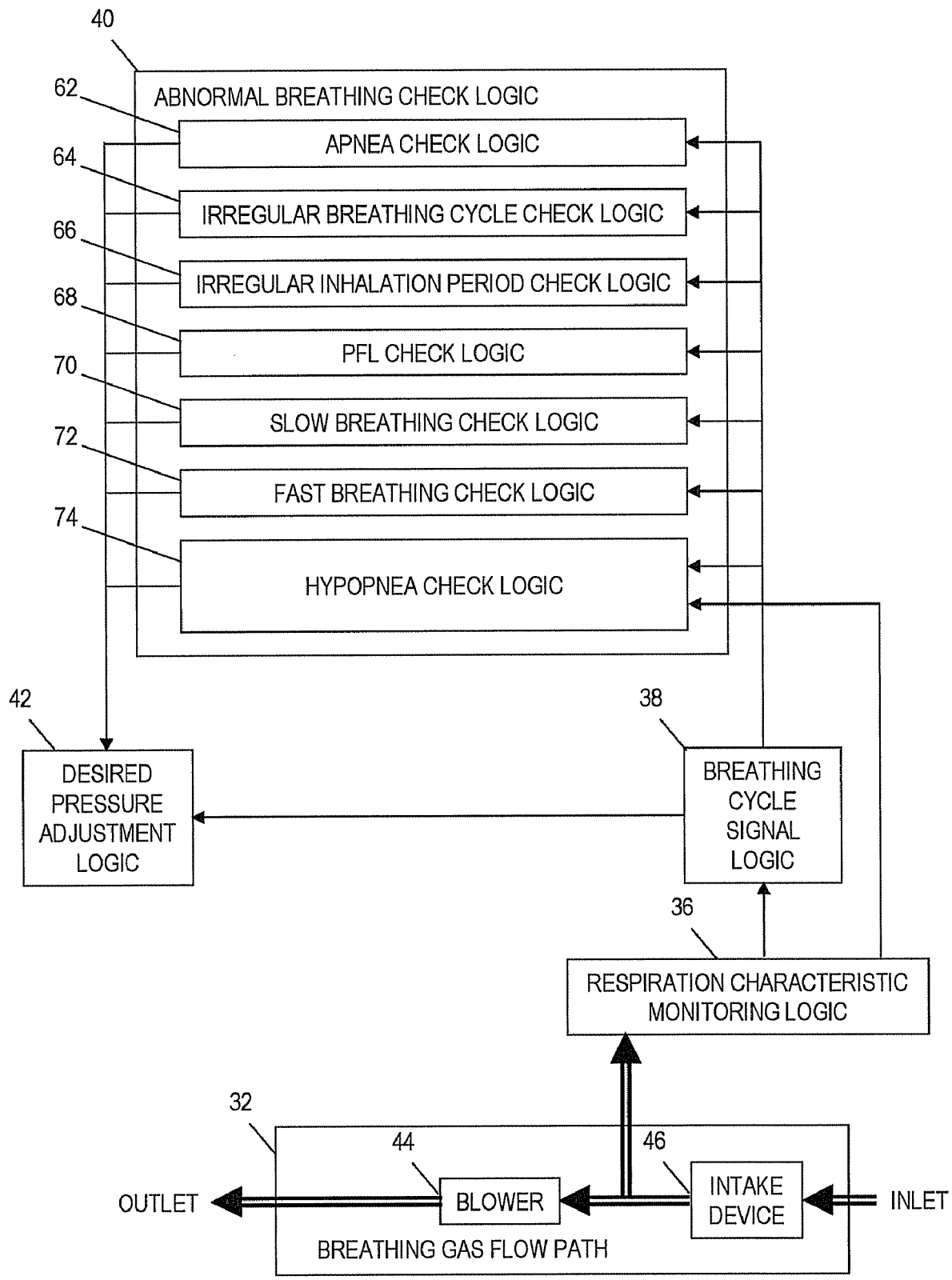
FIG. 3 is a block diagram of an exemplary PAP device with exemplary embodiments of a breathing gas flow path and an abnormal breathing check logic.

With reference to FIG. 3, an embodiment of an exemplary abnormal breathing check logic 40 from the PAP device 30 (FIG. 1) is shown with the exemplary respiration characteristic monitoring logic 36, breathing cycle signal logic 38, and desired pressure adjustment logic 42. The abnormal breathing check logic 40 may include at least one of the following checks: an apnea check logic 62, an irregular breathing cycle check logic 64, an irregular inhalation period check logic 66, a persistent flow limitation (PFL) check logic 68, a slow breathing check logic 70, a fast breathing check logic 72, or a hypopnea check logic 74.

As shown in FIG. 3, the respiration characteristic monitoring logic 36 may be in operative communication with the breathing gas flow path 32 to monitor one or more characteristics related to the breathing gas that may be indicative of respiration. For example, pressure, flow, flow rate, temperature, humidity, $O_2$, and $CO_2$ are characteristics of the breathing gas that may be indicative of respiration. Similarly, blower motor Hall effect, blower motor voltage or current, blower motor speed, breathing gas valve position, and breathing gas vent position are examples of characteristics associated with the PAP device 30 that are related to the breathing gas and may be indicative of respiration. Alternatively, the respiration characteristic monitoring logic 36 may monitor one or more patient physiological characteristics that may be indicative of respiration. For example, any of the characteristics monitored during a PSG are examples of patient physiological characteristics that may be indicative of respiration. Of course, any combination of such breathing gas characteristics, PAP device characteristics, and patient physiological characteristics may be monitored.

In any regard, the respiration characteristic monitoring logic 36 may provide a signal indicative of respiration to the breathing cycle signal logic 38 and the hypopnea check logic 74. The signal indicative of respiration may also be provided to any of the other abnormal breathing check logic components shown in FIG. 3, provided to any other types of breathing check circuits that may be included in the corresponding PAP device (not shown), distributed to other control circuits that may be included in the corresponding PAP device, or any combination thereof. The breathing cycle signal logic 38 may condition the respiration signal to form the breathing cycle signal which, for example, may be distributed to the desired pressure adjustment logic 42, apnea check logic 62, irregular breathing cycle check logic 64, irregular inhalation period check logic 66, PFL check logic 68, slow breathing check logic 70, fast breathing check logic 72, and hypopnea check logic 74.

The apnea check logic 62 may detect an apnea condition (e.g., cessation of breathing) in the patient and indicate the condition on an abnormal breathing signal to the desired pressure adjustment logic 42. The irregular breathing cycle check logic 64 may detect an irregular breathing cycle condition in the patient, for example, with respect to consecutive breathing cycles and indicate the condition on the abnormal breathing signal. Similarly, the irregular inhalation period check logic 66 may detect an irregular inhalation period condition in the patient, for example, with respect to consecutive breathing cycles and indicate the condition on the abnormal breathing signal. The PFL check logic 68 may detect a PFL condition in the patient, for example, with respect to a single breathing cycle and indicate the condition on the abnormal breathing signal. A flow limitation may be caused by the partial closure of the upper airway impeding the flow of air into the lungs. A PFL condition, for example, may exist when the ratio of the inhalation period to the corresponding breathing cycle is greater than a predetermined threshold (e.g., 40%). The slow breathing check logic 70 may detect a slow breathing condition in the patient, for example, with respect to a single breathing cycle and indicate the condition on the abnormal breathing signal. Similarly, the fast breathing check logic 72 may detect a fast breathing condition in the patient, for example, with respect to a single breathing cycle and indicate the condition on the abnormal breathing signal. The hypopnea check logic 74 may detect a hypopnea condition (e.g., shallow breathing) in the patient, for example, with respect to a single breathing cycle and indicate the condition on the abnormal breathing signal.

As shown in the exemplary system of FIG. 3, the abnormal breathing signal from each check may be common via a wired-OR connection. In other embodiments, each abnormal breathing signal may be used independently or in any combination to control desired (target) pressure. For example, the abnormal breathing signal from the irregular breathing cycle check logic 64 and irregular inhalation period check logic 66 may be connected together in a first combination, the abnormal breathing signal from the slow breathing check logic 70 and fast breathing check logic 72 may be connected together in a second combination, and the abnormal breathing signals from the other checks may be independent. If the abnormal breathing signals are independent or grouped, for example, the amount of adjustment to the desired pressure may be different for each independent and grouped signal. This permits different adjustments to the desired pressure to be made by the system in response to different abnormal breathing conditions. For example, the amount of adjustment for one or more independent or grouped signals may be proportional to the difference between normal breathing and the detected abnormal breathing condition. Some conditions, e.g., apnea, may warrant a larger increase in target pressure than other conditions. Any of the aspects of FIG. 3 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 3.

With reference to FIG. 4, another embodiment of an exemplary PAP device 100 may include a pressure control loop circuit 102, a respiratory checks logic 104, and a pressure modify logic 106. The PAP device 100, for example, may be configured as a CPAP device (i.e., standard CPAP, CPAP with SoftX™, etc.), a BiPAP device, a PPAP device, an auto-titrating PAP device, a ventilator device, a gas therapy device, an oxygen therapy device, or another type of PAP device. Generally, the PAP device 100 operates in the same manner as described above for the PAP device 30 of FIGS. 1-3. The pressure control loop circuit 102 may function in essentially the same manner as described above for the breathing gas flow path 32 and closed loop control logic 34 of FIGS. 1-3. The respiratory checks logic 104 may function in essentially the same manner as described above for the respiration characteristic monitoring logic 36, breathing cycle signal logic 38, and abnormal breathing check logic 40 of FIGS. 1-3. The pressure modify logic 106 may function in essentially the same manner as described above for the desired pressure adjustment logic 42 of FIGS. 1-3.

The respiratory checks logic 104 is in operative communication with the pressure control loop circuit 102 to monitor at least one characteristic of the breathing gas that may be indicative of respiration. The respiratory checks logic 104 may detect breathing cycles, including inhalation and exhalation periods, based at least in part on one or more monitored respiration characteristics. Additionally, the respiratory checks logic 104 may detect one or more types of abnormal breathing conditions based at least in part on the detected inhalation period, detected exhalation period, detected breathing cycle, or one or more monitored respiration characteristics. In conjunction with these operations, the respiratory checks logic 104 may produce abnormal breathing information and a synchronization signal. The abnormal breathing information may include one or more signals which may designate detection of a general abnormal breathing condition or detection of a specific type of abnormal breathing condition. The synchronization signal may be based at least in part on the detected breathing cycle, detected inhalation period, or detected exhalation period.

The pressure modify logic 106 is in operative communication with the respiratory checks logic 104 to receive the abnormal breathing information and synchronization signal. Additionally, the pressure modify logic 106 may permit selection of various operating modes (e.g., standard CPAP, CPAP with initial ramping period, CPAP with SoftX™, auto-titrating CPAP, BiPAP, etc.). The pressure modify logic 106 may optionally be in operative communication with the pressure control loop circuit 102 to receive a signal indicating that a closed loop control circuit is operating at or about its maximum power. The pressure modify logic 106 may use the closed loop maximum power signal to determine if a runaway low pressure condition exists. For example, a runaway low pressure condition may exist if the breathing gas flow path has a large leak, if the mask is either not being worn, or if the mask is poorly seated in relation to the patient's facial area. Based at least in part on the abnormal breathing information, operating mode selection, or runaway low pressure condition, the pressure modify logic 106 determines a desired pressure for the breathing gas in relation to time. The pressure modify logic 106 may use the synchronization signal to periodically adjust a desired pressure signal based on the current desired pressure.

The pressure control loop circuit 102 may include a breathing gas flow path with an inlet to receive breathing gas and an outlet to provide pressurized breathing gas to a patient mask. Additionally, the pressure control loop circuit 102 is in operative communication with the pressure modify logic 106 to receive the desired (target) pressure signal. The pressure control loop circuit 102 may monitor a characteristic of the breathing gas related to pressure to produce a detected pressure signal. The desired pressure and detected pressure signals may be compared by the pressure control loop circuit 102. A variable component associated with the breathing gas flow path may be adjusted in closed loop control fashion to minimize the difference (i.e., error signal) between the compared signals. The error signal may be conditioned using various control techniques (e.g., proportional (P), integral (I), derivative (D), or any combination thereof) to adjust a drive signal to the variable component. The variable component, for example, may include a variable speed blower motor, a variable position breathing gas valve, or a variable position breathing gas vent.

With continuing reference to FIG. 4, the pressure control loop circuit 102 may include an intake silencer 108, a blower 110, a sensor 112 (e.g., a pressure sensor), a subtractor 114, a gain stage 116, a control loop filter 118, a power stage 120, and a blower motor 122. The intake silencer 108 and blower 110 may form a breathing gas flow path from the breathing gas inlet to a pressurized breathing gas outlet. The outlet may be connected to a patient mask. The intake silencer 108, for example, may provide flow restriction. The pressure sensor 112 is in operative communication with the breathing gas flow path to monitor a characteristic of the breathing gas related to pressure. Additionally, the pressure sensor 112 may produce a detected pressure signal based at least in part on the monitored pressure characteristic. The subtractor 114 is in operative communication with the pressure modify logic 106 and the pressure sensor 112 to receive the desired pressure and detected pressure signals. The subtractor 114, gain stage 116, control loop filter 118, and power stage 120 may form a closed loop control circuit to control the speed of the blower motor 122. The blower motor 122 is operationally coupled to the blower 110 such that speed of the blower motor 122 relates to pressure of the breathing gas in the breathing gas flow path between the output of the blower 110 and the patient airway to which the patient mask provides pressurized breathing gas. The subtractor 114 may compare the desired pressure signal to the detected pressure signal to develop an error signal. The gain stage 116, control loop filter 118, and power stage 120 may adjust a drive signal controlling the speed of the blower motor 122 to minimize the error signal. The gain stage 116, control loop filter 118, and power stage 120 may condition the error signal using various control techniques (e.g., proportional (P), integral (I), derivative (D), or any combination thereof) to adjust the drive signal to the blower motor 122.

The respiratory checks logic 104 may include a pressure sensor 124, a noise suppression filter 126, an inhaling signal logic 128, an apnea detection logic 130, an irregular breathing detect logic 132, a PFL detection logic 134, a breathing speed out of bounds logic 136, and a hypopnea detect logic 138. The pressure sensor 124 is in operative communication with the breathing gas flow path between the intake silencer 108 and the blower 110 to monitor a characteristic of the breathing gas that may be indicative of respiration. Additionally, the pressure sensor 124 may produce a detected respiration signal based at least in part on the monitored respiration characteristic. The noise suppression filter 126 is in operative communication with the pressure sensor 124 to receive the detected respiration signal and produce a filtered respiration signal. The inhaling signal logic 128, apnea detection logic 130, irregular breathing detect logic 132, PFL detection logic 134, breathing speed out of bounds logic 136, and hypopnea detect logic 138 may form a group of abnormal breathing checks that are described in more detail below with reference to FIGS. 5-7. Generally, this group is in operative communication with the pressure sensor 124 and noise suppression filter 126 to receive the detected and filtered respiration signals. Overall, the abnormal breathing check group may perform certain abnormal breathing checks by processing the detected and filtered respiration signals and may produce corresponding abnormal breathing information based at least in part on the results of the checks. The group may also produce a synchronization signal based at least in part on the detected and filtered respiration signals. The abnormal breathing information and synchronization signals may be communicated to the pressure modify logic 106.

The pressure modify logic 106 may include an optional open loop detection logic 140, a constant pressure setting logic 142, a mode switch 144, a pressure increase decision logic 146, a pressure decrease storage logic 148, a minimum pressure decision logic 150, a decrement pressure value logic 152, a modify set pressure logic 154, a hold set pressure logic 156, a maximum pressure decision logic 158, an increment pressure value logic 160, and a load startup pressure logic 162. The optional open loop detection logic 140 is in operative communication with the pressure control loop circuit 102 to receive the closed loop maximum power signal. The open loop detection logic 140 may determine that a runaway low pressure condition exists if the closed loop maximum power signal indicates that the closed loop control circuit within the pressure control loop circuit 102 is operating at or about its maximum power for a predetermined period of time. Additionally, the open loop detection circuit 140 may produce a runaway low pressure signal to indicate that the runaway low pressure condition exists. The runaway low pressure signal may be communicated to the load startup pressure logic 162. Alternatively, or additionally, a warning or alarm condition may be triggered when a runaway low pressure condition is detected. In various embodiment, the alarm condition may initiate audible, visual, or tactile stimuli to the patient, initiate audible alarms, visual alarms, or messaging to a caretaker or healthcare provider, or any combination thereof.

The pressure increase decision logic 146 is in operative communication with the respiratory checks logic 104 to receive the abnormal breathing information. If the abnormal breathing information indicates "no abnormal breathing detected," the pressure increase decision logic 146 may enable the pressure decrease storage logic 148. The pressure decrease storage logic 148 is also in operative communication with the respiratory checks logic 104 to receive the synchronization signal. When enabled due to an abnormal breathing condition, a level transition (e.g., positive or negative transition) on the synchronization signal may clock or store detection of any abnormal breathing condition during the current synchronization interval (e.g., breathing cycle, inhalation period, exhalation period) in the pressure decrease storage logic 148. The stored abnormal breathing condition may be communicated to the minimum pressure decision logic 150 which may check to see if the current desired pressure is at a minimum desired pressure. If the current desired pressure is not at the minimum, the minimum pressure decision logic 150 may activate the decrement pressure value logic 152.

When the abnormal breathing information indicates "abnormal breathing detected," the pressure increase decision logic 146 may pass the abnormal breathing information to the maximum pressure decision logic 158. The maximum pressure decision logic 158 may check to see if the current desired pressure is at a maximum desired pressure. If the current desired pressure is not at the maximum, the maximum pressure decision logic 158 may activate the increment pressure value logic 160.

The modify set pressure logic 154 is in operative communication with the load startup pressure logic 162, decrement pressure value logic 152, and increment pressure value logic 160 to receive abnormal breathing information and runaway low pressure information. The modify set pressure logic 154 evaluates the information and determines whether or not to make an adjustment to the current desired pressure. For example, if a runaway lower pressure condition exists, the modify set pressure logic 154 may reset the current desired pressure to a startup or default value. Otherwise, if an abnormal breathing condition is detected and the current desired pressure is not set to a maximum pressure, the modify set pressure logic 154 may increment the current desired pressure by a first increment. Conversely, if an abnormal breathing condition is not detected and the current desired pressure is not set to a minimum pressure, the modify set pressure logic 154 may decrement the current desired pressure by a second increment. Normally, the first increment is larger than the second increment. If the above conditions are not found, the modify set pressure logic 154 may not adjust the current desired pressure and the hold set pressure logic 156 may be activated.

The modify set pressure logic 154 may communicate the desired set pressure to the mode switch 144. If the mode switch is set, for example, to an auto-titrating CPAP position, the desired set pressure may be communicated to the pressure control loop circuit 102 as a desired pressure signal. Otherwise, for example, if the mode switch is set to a standard CPAP position, a desired constant pressure may be communicated to the pressure control loop circuit 102 as the desired pressure signal. Any of the aspects of FIG. 4 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 4.

With reference to FIG. 5, an embodiment of an exemplary first portion of the respiratory checks logic 104 from the PAP device 100 of FIG. 4 may include the inhaling signal logic 128, apnea detection logic 130, irregular breathing detect logic 132, PFL detection logic 134, and breathing speed out of bounds logic 136. The apnea detection logic 130 may detect cessation or absence of breathing for a predetermined time (e.g., 10 seconds). The irregular breathing detect logic 132 may detect a time difference between consecutive breathing cycles that exceeds a predetermined threshold. Similarly, the irregular breathing detect logic 132 may also detect a time difference between consecutive inhalation periods that exceeds a predetermined threshold. The PFL detection logic 134 may detect flow limitation conditions in which the ratio of the inhalation period to the breathing cycle exceeds a predetermined threshold (e.g., 40%). The breathing speed out of bounds logic 136 may detect when a breathing cycle either exceeds a first predetermined threshold associated with breathing too slow or is less than a second predetermined threshold associated with breathing too fast.

The inhaling signal logic 128 may include a Schmitt trigger 163. The Schmitt trigger 163 is in operative communication with the noise suppression filter 126 (FIG. 4) to receive the filtered respiration signal. Additionally, the Schmitt trigger 163 may produce a breathing cycle signal that alternates between a first (e.g., high) logic level and a second (e.g., low) logic level based at least in part on an amplitude for the filtered respiration signal over time. Each cycle of the first and second logic levels is a general representation of a breathing cycle. For example, the first logic level periods may be indicative of inhalation periods and the second logic level periods indicative of exhalation periods.

The apnea detection logic 130 may include a timeout counter 164. The timeout counter 164 is in operative communication with the Schmitt trigger 163 to receive the breathing cycle signal. Each new breathing cycle may reset the timeout counter 164. Upon reset, the timeout counter 164 may be set to a value that results in an overflow or maximum time signal if the next breathing cycle has not occurred before a time (e.g., ten seconds) that is indicative of an abnormal breathing condition known as apnea. The overflow or maximum time signal caused by the apnea condition may by included in the abnormal breathing information either independently or in combination with one or more additional types of abnormal breathing conditions. The Schmitt trigger 163 and timeout counter 164 may be combined to form an embodiment of an apnea check logic independent of other abnormal breathing checks.

In another embodiment, the apnea detection logic 130 may include any known circuit, logic component, or combination thereof currently used to detect apnea conditions, including obstructive apnea or central apnea, caused by the cessation or absence of breathing or markedly reduced breathing. For example, the apnea detection logic 130 may monitor the flow of breathing gas to identify the cessation or absence of breathing for a predetermined time (e.g., 10 seconds). In another example, the apnea detection logic 130 may monitor airflow to identify cessation of breathing or markedly reduced breathing in the range of about 90% to about 100%.

The irregular breathing detect logic 132 may include a system timer 166, an inhale start storage logic 168, a first breathing cycle subtractor 170, a first breathing cycle storage logic 172, a second breathing cycle storage logic 174, a second breathing cycle subtractor 176, a breathing cycle absolute value logic 178, an irregular breathing cycle decision logic 180, a first inhale subtractor 182, a first inhale storage logic 184, a second inhale storage logic 186, a second inhale subtractor 188, an inhale absolute value logic 190, and an irregular inhale decision logic 192. The inhale start storage logic 168, first breathing cycle storage logic 172, second breathing cycle storage logic 174, first inhale storage logic 184, and second inhale storage logic 186 are in operative communication with the Schmitt trigger 163 to receive the breathing cycle signal. The system timer 166 may produce count information that is continuously changing during operation of the PAP device 100 (FIG. 4). The inhale start storage logic 168, first breathing cycle subtractor 170, and first inhale subtractor are in operative communication with the system timer 166 to receive the count information.

The combination of the system timer 166, inhale start storage logic 168, first breathing cycle subtractor 170, first breathing cycle storage logic 172, second breathing cycle storage logic 174, second breathing cycle subtractor 176, breathing cycle absolute value logic 178, and irregular breathing cycle decision logic 180 may form an irregular breathing cycle check within the irregular breathing detect logic 132. The inhale start storage logic 168 may store the current count information from the system timer 166, for example, on each rising edge transition of the breathing cycle signal. In this example, each rising edge transition is related to a start of each breathing cycle (start of inhalation). Thus, the stored count information is generally representative of start information for the current breathing cycle. The first breathing cycle subtractor 170 is in operative communication with inhale start storage logic 168 to receive the stored start information. Additionally, the first breathing cycle subtractor 168 may compare the current count information to the start information to produce duration information for the current breathing cycle.

The first breathing cycle storage logic 172 may store the duration information from the first breathing cycle subtractor 170, for example, on each rising edge transition of the breathing cycle signal. The second breathing cycle storage logic 174 and the second breathing cycle subtractor 176 are in operative communication with first breathing cycle storage logic 172 to receive the duration information for the current breathing cycle. The second breathing cycle storage logic 174 may store the duration information from the first breathing cycle storage logic 172, for example, on each rising edge transition of the breathing cycle signal. In this example, the duration information stored in the second breathing cycle storage logic 174 is generally representative of duration information for the previous breathing cycle. The second breathing cycle subtractor 176 is in operative communication with second breathing cycle storage logic 174 to receive the stored duration information for the previous breathing cycle. Additionally, the second breathing cycle subtractor 176 may compare the duration information for the current and previous breathing cycles to produce difference information.

The breathing cycle absolute value logic 178 may receive the breathing cycle difference information and produce a corresponding absolute value. The irregular breathing cycle decision logic 180 is in operative communication with the breathing cycle absolute value logic 178 to receive the breathing cycle difference information in absolute value form. Additionally, the irregular breathing cycle decision logic 180 may determine if the breathing cycle difference information exceeds a corresponding predetermined maximum value. If the maximum value is exceeded, an irregular breathing cycle condition may be present and the irregular breathing cycle decision logic 180 may produce an irregular breathing cycle signal. The irregular breathing cycle signal may by included in the abnormal breathing information either independently or in combination with one or more additional types of abnormal breathing conditions. The Schmitt trigger 163, system timer 166, inhale start storage logic 168, first breathing cycle subtractor 170, first breathing cycle storage logic 172, second breathing cycle storage logic 174, second breathing cycle subtractor 176, breathing cycle absolute value logic 178, and irregular breathing cycle decision logic 180 may be combined to form an embodiment of an irregular breathing cycle check logic independent of other abnormal breathing checks.

The combination of the system timer 166, inhale start storage logic 168, first inhale subtractor 182, first inhale storage logic 184, second inhale storage logic 186, second inhale subtractor 188, inhale absolute value logic 190, and irregular inhale decision logic 192 may form an irregular inhalation period check within the irregular breathing detect logic 132. The first inhale subtractor 182 is in operative communication with the inhale start storage logic 168 to receive the stored start information. Additionally, the first inhale subtractor 182 may compare the current count information to the start information to produce duration information for the current breathing cycle.

The first inhale storage logic 184 may store the duration information from the first inhale subtractor 182, for example, on each trailing edge transition of the breathing cycle signal. In this example, each trailing edge transition is related to an end of each inhalation period. Thus, the stored duration information is generally representative of duration information for the current inhalation period. The second inhale storage logic 186 and the second inhale subtractor 188 are in operative communication with first inhale storage logic 184 to receive the duration information for the current inhalation period. The second inhale storage logic 186 may store the duration information from the first inhale storage logic 184, for example, on each trailing edge transition of the breathing cycle signal. In this example, the duration information stored in the second inhale storage logic 186 is generally representative of duration information for the previous inhalation period. The second inhale subtractor 188 is in operative communication with second inhale storage logic 186 to receive the stored duration information for the previous breathing cycle. Additionally, the second inhale subtractor 188 may compare the duration information for the current and previous inhalation periods to produce difference information.

The inhale absolute value logic 190 may receive the inhalation period difference information and produce a corresponding absolute value. The irregular inhale decision logic 192 is in operative communication with the inhale absolute value logic 190 to receive the inhalation period difference information in absolute value form. Additionally, the irregular inhale decision logic 192 may determine if the inhalation difference information exceeds a corresponding predetermined maximum value. If the maximum value is exceeded, an irregular inhalation period condition may be present and the irregular inhale decision logic 180 may produce an irregular inhalation period signal. The irregular inhalation period signal may by included in the abnormal breathing information either independently or in combination with one or more additional types of abnormal breathing conditions. The Schmitt trigger 163, system timer 166, inhale start storage logic 168, first inhale subtractor 182, first inhale storage logic 184, second inhale storage logic 186, second inhale subtractor 188, inhale absolute value logic 190, and irregular inhale decision logic 192 may be combined to form an embodiment of an irregular inhalation period check logic independent of other abnormal breathing checks.

The PFL detection logic 134 may include an inhale/breathing cycle ratio logic 194 and an inhale/breathing cycle ratio decision logic 196. The inhale/breathing cycle ratio logic 194 is in operative communication with the first breathing cycle storage logic 172 and first inhale storage logic 184 to receive duration information for the current breathing cycle and current inhalation period. The inhale/breathing cycle ratio logic 194 determines the ratio of, for example, the current inhalation period to the current breathing cycle to produce a corresponding ratio information. The inhale/breathing cycle ratio decision logic 196 is in operative communication with the inhale/breathing cycle ratio logic 194 to receive the ratio information. Additionally, the inhale/breathing cycle ratio decision logic 196 may determine if the ratio information exceeds a corresponding predetermined maximum value (e.g., 40%).

If the maximum value is exceeded, a PFL condition may be present and the inhale/breathing cycle ratio decision logic 196 may produce a PFL signal. The PFL signal may by included in the abnormal breathing information either independently or in combination with one or more additional types of abnormal breathing conditions. The Schmitt trigger 163, system timer 166, inhale start storage logic 168, first breathing cycle subtractor 170, first breathing cycle storage logic 172, first inhale subtractor 182, first inhale storage logic 184, inhale/breathing cycle ratio logic 194, and inhale/breathing cycle ratio decision logic 196 may be combined to form an embodiment of a PFL check logic independent of other abnormal breathing checks.

In another embodiment, the PFL detection logic 134 may include any known circuit, logic component, or combination thereof currently used to detect PFL conditions caused by airflow limitations during breathing. For example, the PFL detection logic 134 may monitor the flow of breathing gas to identify reduced airflow which may be caused by a partial closure in the upper airway.

The breathing speed out of bounds logic 136 may include a slow breathing decision logic 198 and a fast breathing decision logic 200. The slow breathing decision logic 198 and fast breathing decision logic 200 are in operative communication with the first breathing cycle storage logic 172 to receive duration information for the current breathing cycle.

The slow breathing decision logic 198 may determine if the current breathing cycle duration information exceeds a corresponding predetermined maximum value. If the maximum value is exceeded, a slow breathing condition may be present and the slow breathing decision logic 198 may produce a slow breathing signal. The slow breathing signal may by included in the abnormal breathing information either independently or in combination with one or more additional types of abnormal breathing conditions. The Schmitt trigger 163, system timer 166, inhale start storage logic 168, first breathing cycle subtractor 170, first breathing cycle storage logic 172, and slow breathing decision logic 198 may be combined to form an embodiment of a slow breathing check logic independent of other abnormal breathing checks.

The fast breathing decision logic 200 may determine if the current breathing cycle duration information is less than a corresponding predetermined minimum value. If the duration information for the current breathing cycle is less than the minimum value, a fast breathing condition may be present and the fast breathing decision logic 200 may produce a fast breathing signal. The fast breathing signal may by included in the abnormal breathing information either independently or in combination with one or more additional types of abnormal breathing conditions. The Schmitt trigger 163, system timer 166, inhale start storage logic 168, first breathing cycle subtractor 170, first breathing cycle storage logic 172, and fast breathing decision logic 200 may be combined to form an embodiment of a fast breathing check logic independent of other abnormal breathing checks. Any of the aspects of FIG. 5 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 5.

With reference to FIG. 6, another embodiment of an exemplary first portion of a respiratory checks logic 104 from the PAP device 100 of FIG. 4 may include an inhaling signal logic 128, an apnea detection logic 130', an irregular breathing detect logic 132', a PFL detection logic 134', and a breathing speed out of bounds logic 136'. The inhaling signal logic 128 may include the same components and may function in the same manner as described above for the inhaling signal logic 128 of FIG. 5.

The apnea detection logic 130' may include the same components and may function in the same manner as described above for the apnea detection logic 130 of FIG. 5. Additionally, the apnea detection logic 130' may include an apnea pressure increase logic 202. The apnea pressure increase logic 202 may independently condition, scale, or otherwise process the overflow or maximum time signal from the timeout counter 164 to produce independent apnea information. The independent apnea information, for example, may include pressure increase information that is specifically tailored to the current apnea condition.

The irregular breathing detect logic 132' may include the same components and may function in the same manner as described above for the irregular breathing detect logic 132 of FIG. 5. Additionally, the irregular breathing detect logic 132' may include an irregular breathing cycle pressure increase logic 204 and an irregular inhale pressure increase logic 206. The irregular breathing cycle pressure increase logic 204 may independently condition, scale, or otherwise process the irregular breathing cycle signal from the irregular breathing cycle decision logic 180 to produce independent irregular breathing cycle information. The independent irregular breathing cycle information, for example, may include pressure increase information that is specifically tailored to the current irregular breathing cycle condition. The irregular inhale pressure increase logic 206 may independently condition, scale, or otherwise process the irregular inhalation period signal from the irregular inhale decision logic 192 to produce independent irregular inhalation period information. The independent irregular inhalation period information, for example, may include pressure increase information that is specifically tailored to the current irregular inhalation period condition.

The PFL detection logic 134' may include the same components and may function in the same manner as described above for the PFL detection logic 134 of FIG. 5. Additionally, the PFL detection logic 134' may include a PFL pressure increase logic 208. The PFL pressure increase logic 208 may independently condition, scale, or otherwise process the PFL signal from the inhale/breathing cycle ratio decision logic 196 to produce independent PFL information. The independent PFL information, for example, may include pressure increase information that is specifically tailored to the current PFL condition.

The breathing speed out of bounds logic 136' may include the same components and may function in the same manner as described above for the breathing speed out of bounds logic 136 of FIG. 5. Additionally, the breathing speed out of bounds logic 136' may include a slow breathing speed pressure increase logic 210 and a fast breathing speed pressure increase logic 212. The slow breathing speed pressure increase logic 210 may independently condition, scale, or otherwise process the slow breathing signal from the slow breathing decision logic 198 to produce independent slow breathing information. The independent slow breathing information, for example, may include pressure increase information that is specifically tailored to the current slow breathing condition. The fast breathing speed pressure increase logic 212 may independently condition, scale, or otherwise process the fast breathing signal from the fast breathing decision logic 200 to produce independent fast breathing information. The independent fast breathing information, for example, may include pressure increase information that is specifically tailored to the current fast breathing condition. Any of the aspects of FIG. 6 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 6.

With reference to FIG. 7, an embodiment of an exemplary second portion of a respiratory checks logic 104 from the PAP device 100 of FIG. 4 may include the hypopnea detect logic 138. The hypopnea detect logic 138 may include a bandpass filter 212, a Schmitt trigger 214, a positive surge counter 216, a negative surge counter 218, a positive surge sampler logic 220, a negative surge sampler logic 222, a positive surge decision logic 224, and a negative surge decision logic 226. The bandpass filter 212, for example, may be in operative communication with the noise suppression filter 126 (FIG. 4) to receive the filtered respiration signal. Additionally, the bandpass filter 212 may produce the bandpass signal (i.e., bandpass filtered respiration signal) 236 (FIG. 9) based at least in part on the filtered pressure signal.

The Schmitt trigger 214 is in operative communication with the bandpass filter 212 to receive the bandpass signal 236 (FIG. 9). Additionally, the Schmitt trigger 214 may produce the triggered respiration signal 238 (FIG. 9) that alternates between a first logic level (e.g., high) and a second logic level (e.g., low) based at least in part on an amplitude for the bandpass signal 236 (FIG. 9) over time. For example, the high and low logic levels may reflect positive and negative surges, respectively, on the bandpass signal. Since a first positive surge during each inhalation period is normal, components for the bandpass filter 212 and Schmitt trigger 214 may be selected to filter out the first positive surge. However, more than one negative surge and intermediate positive surges during the inhalation period may reflect an irregular breathing pattern known as hypopnea.

The positive surge counter 216, negative surge counter 218, positive surge sampler logic 220, and negative surge sampler logic 222 are in operative communication with the inhaling signal logic 128 (FIG. 4) to receive the breathing cycle signal produced by the Schmitt trigger 163 (FIG. 5). As discussed above, the breathing cycle signal alternates between a first logic level (e.g., high) and a second logic level (e.g., low) based at least in part on an amplitude for the filtered respiration signal from the noise suppression filter 126 (FIG. 4) over time. The positive surge counter 216 and negative surge counter 218 are in operative communication with the Schmitt trigger 214 to receive the triggered respiration signal 238 (FIG. 9).

The positive surge counter 216, for example, may count each rising edge transition of the triggered respiration signal 238 (FIG. 9) to produce a positive surge count. In this example, each rising edge transition of the triggered respiration signal 238 (FIG. 9) is related to an intermediate positive surge. Additionally, the positive surge counter 216, for example, may be reset on each trailing edge transition of the breathing cycle signal. In this example, each trailing edge transition of the breathing cycle signal is related to an end of a corresponding inhalation period. Thus, intermediate positive surge counts during a corresponding inhalation period are counted by the positive surge counter 216. The positive surge count sample logic 220 is in operative communication with the positive surge counter 216 to receive the positive surge count. Additionally, the positive surge count sample logic 220 stores the positive surge count on each trailing edge transition of the breathing cycle signal to produce a stored positive count.

The positive surge decision logic 224 is in operative communication with the positive surge count sample logic 220 to receive the stored positive count. Additionally, the positive surge decision logic 220 may determine if the stored positive count, for example, is not zero. If the stored positive count is not zero, a hypopnea condition may exist due to an unexpected positive inhalation surge and the positive surge decision logic 224 may produce a corresponding hypopnea signal. It should be noted that the positive surge decision logic 220 expects zero positive inhalation surges because the embodiment being described is counting intermediate positive inhalation surges after the initial positive inhalation surge associated with the start of inhalation. In another embodiment, if the initial positive inhalation surge is counted, the positive surge decision logic 224 would expect one positive inhalation surge. Returning to the embodiment of FIG. 7, the corresponding hypopnea signal may by included in the abnormal breathing information either independently or in combination with one or more additional types of abnormal breathing conditions. The Schmitt trigger 163, bandpass filter 212, Schmitt trigger 214, positive surge counter 216, positive surge sampler logic 220, and positive surge decision logic 224 may be combined to form an embodiment of a positive surge hypopnea check logic independent of other abnormal breathing checks.

The negative surge counter 218, for example, may count each trailing edge transition of the triggered respiration signal 238 (FIG. 9) to produce a negative surge count. In this example, each trailing edge transition of the triggered respiration signal 238 (FIG. 9) is related to a negative surge. Additionally, the negative surge counter 218, for example, may be reset on each trailing edge transition of the breathing cycle signal. In this example, each trailing edge transition of the breathing cycle signal is related to an end of a corresponding inhalation period. Thus, negative surge counts during a corresponding inhalation period are counted by the negative surge counter 218. The negative surge count sample logic 222 is in operative communication with the negative surge counter 218 to receive the negative surge count. Additionally, the negative surge count sample logic 222 stores the negative surge count on each trailing edge transition of the breathing cycle signal to produce a stored negative count.

The negative surge decision logic 226 is in operative communication with the negative surge count sample logic 222 to receive the stored negative count. Additionally, the negative surge decision logic 222 may determine if the stored negative count, for example, is not one. If the stored negative count is not one, a hypopnea condition may exist due to an unexpected negative inhalation surge and the negative surge decision logic 226 may produce a corresponding hypopnea signal. The corresponding hypopnea signal may by included in the abnormal breathing information either independently or in combination with one or more additional types of abnormal breathing conditions. The Schmitt trigger 163, bandpass filter 212, Schmitt trigger 214, negative surge counter 218, negative surge sampler logic 222, and negative surge decision logic 226 may be combined to form an embodiment of a negative surge hypopnea check logic independent of other abnormal breathing checks. Any of the aspects of FIG. 7 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 7.

In another embodiment, the hypopnea detection logic 138 may include any known circuit, logic component, or combination thereof currently used to detect a hypopnea condition. For example, the hypopnea detection logic 138 may monitor airflow to identify a decrease in volume of at least 50% from a normal baseline during inhalation. In another example, the hypopnea detection logic 138 may monitor airflow to identify a decrease of at least 50% over a predetermined time, such as 10 seconds. In yet another example, the hypopnea detection logic 138 may monitor airflow to identify a partial cessation of breathing or reduced breathing in the range of about 50% to about 90%.

With reference to FIG. 8, exemplary signal waveforms are shown, including waveforms associated with a monitored respiratory characteristic (e.g., airflow rate signal) 228 and a breathing cycle signal (e.g., inhaling signal) 230 associated with various methods and apparatuses described herein. The monitored respiratory characteristic (e.g., airflow rate signal) 228, for example, is representative of the output signals from the pressure sensor 124 (FIG. 4) and noise suppression filter 126 (FIG. 4). The breathing cycle signal (e.g., inhaling signal) 230, for example, is representative of the output signal from the Schmitt trigger 163 (FIG. 5). Any of the aspects of FIG. 8 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 8.

With reference to FIG. 9, exemplary signal waveforms are shown, including waveforms associated with a monitored respiratory characteristic (e.g., airflow rate signal) 232, an example of a derivate signal of the monitored respiratory characteristic (e.g., dV/dt) 234, a bandpass filtered respiration signal (i.e., bandpass signal) 236, and a triggered respiration signal (e.g., Schmitt trigger signal) 238 associated with various methods and apparatuses described herein in conjunction with detection of abnormal breathing due to a hypopnea condition. The monitored respiratory characteristic (e.g., airflow rate signal) 232, for example, is representative of the output signals from the pressure sensor 124 (FIG. 4) and noise suppression filter 126 (FIG. 4). The exemplary derivative signal (e.g., dV/dt) 234, for example, is representative of an output signal for an embodiment where the monitored respiratory characteristic (e.g., airflow rate signal) 232 is provided to a differentiator and a low pass filter instead of the bandpass filter 212 (FIG. 7). The bandpass signal 236, for example, is representative of the output signal from the bandpass filter 212 (FIG. 7). Notably, the bandpass signal and the derivative signal are similar and may be interchangeable with respect to certain criteria. However, for other criteria, such as recurring material cost, one option may be preferred over the other. The triggered respiration signal (e.g., Schmitt trigger signal) 238, for example, is representative of the output signal from the Schmitt trigger 214 (FIG. 7). Any of the aspects of FIG. 9 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 9.

With reference to FIG. 10, an exemplary signal waveform associated with a monitored respiratory characteristic (e.g., airflow rate signal) 240 is shown, as well as a corresponding signal waveform for a breathing cycle signal (e.g., inhaling signal) 242, and corresponding positive surge counts 244 and negative surge counts 246 associated with various methods and apparatuses described herein in conjunction with normal breathing and the hypopnea check. The monitored respiratory characteristic (e.g., airflow rate signal) 240, for example, is representative of the output signals from the pressure sensor 124 (FIG. 4) and noise suppression filter 128 (FIG. 4). The breathing cycle signal (e.g., inhaling signal) 242, for example, is representative of the output signal from the Schmitt trigger 163 (FIG. 5). The positive surge counts 244, for example, are representative of values read from the positive surge sampler logic 220 (FIG. 7). The negative surge counts 246, for example, are representative of values read from the negative surge sampler logic 222 (FIG. 7). Any of the aspects of FIG. 10 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 10.

With reference to FIG. 11, an exemplary signal waveform associated with a monitored respiratory characteristic (e.g., airflow rate signal) 248 is shown, as well as a corresponding signal waveform for a breathing cycle signal (e.g., inhaling signal) 250, and corresponding positive surge counts 252 and negative surge counts 254 associated with various methods and apparatuses described herein in conjunction with detection of abnormal breathing due to a hypopnea condition. The monitored respiratory characteristic (e.g., airflow rate signal) 248, for example, is representative of the output signals from the pressure sensor 124 (FIG. 4) and noise suppression filter 128 (FIG. 4). The breathing cycle signal (e.g., inhaling signal) 250, for example, is representative of the output signal from the Schmitt trigger 163 (FIG. 5). The positive surge counts 252, for example, are representative of values read from the positive surge sampler logic 220 (FIG. 7). The negative surge counts 254, for example, are representative of values read from the negative surge sampler logic 222 (FIG. 7). The exemplary scenario in FIG. 11 depicts these signals for an inhalation portion of a patient's breathing cycle in which three intermediate positive surges and four negative surges are detected. This reflects an abnormal breathing condition indicative of hypopnea. As described above, no (0) intermediate positive surges and only one (1) negative surge is expected during the inhalation portion of a normal breathing cycle. Any of the aspects of FIG. 11 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 11.

With reference to FIG. 12, another embodiment of an exemplary PAP device 100' may include a mask 101, a pressure control loop circuit 102', an interconnect plenum 103, a respiratory checks logic 104', and a pressure modify logic 106. The pressure control loop circuit 102' may include the components described above for the pressure control loop circuit 102 of FIG. 4, except the intake silencer 108 may not be included in this embodiment. The respiratory checks logic 104' may include the components described above for the respiratory checks logic 104 of FIG. 4, except the pressure sensor 124 may not be included in this embodiment. Rather, as discussed above in conjunction with FIGS. 1 and 3, a $CO_2$ sensor 105 may monitor the breathing gas because the $CO_2$ characteristic of the breathing gas may be indicative of respiration (i.e., patient breathing). The pressure modify logic 106 may include the same components and may function in the essentially the same manner as described above for the pressure modify logic 106 of FIG. 4.

The mask 101 may include a $CO_2$ sensor 105 with an input conduit 107 and an output conduit 109. In this embodiment, during normal operation of the PAP device 100', breathing gas may be drawn into the inlet by the blower 110 (FIG. 4) and pressurized breathing gas may flow to a user airway associated with an interior of the mask 101 via the interconnect plenum 103. This flow within the breathing gas flow path is indicated in FIG. 12 by the solid line arrow pointed toward the user airway. Some pressurized breathing gas may also flow through the input conduit 107, $CO_2$ sensor 105, and output conduit 109 to an area outside the mask 101. During exhalation, $CO_2$-rich gas may be exhaled into the mask by the patient and may be vented from the breathing gas flow path via the input conduit 107, $CO_2$ sensor 105, and output conduit 109. This flow within the breathing gas flow path is indicated in FIG. 12 by the dashed line arrows showing flow through the $CO_2$ sensor 105. Generally, the PAP device 100' may be operated, and the interconnect plenum 103 and input and output conduits 107, 109 may be sized, so that positive pressure within the interconnect plenum 103 and interior of the mask 101 may flush the $CO_2$-rich gas out through the input conduit 107, $CO_2$ sensor 105, and output conduit 109 during exhalation periods.

The $CO_2$ sensor 105, for example, may be any sensor suitable detecting concentrations of $CO_2$ during in a normal exhalation phase of a user's breathing cycle. For example, various types of $CO_2$ sensors may include any of the various infrared (IR) light emitters and detectors such as those employed by a PAP device disclosed in U.S. Pat. No. 6,990,980 to Richey II and assigned to Invacare Corporation, the contents of this patent are fully incorporated herein by reference. The $CO_2$ sensor 105 may produce a detected respiration signal based at least in part on a level of $CO_2$ within the gas passing through the $CO_2$ sensor 105. The detected respiration signal from the $CO_2$ sensor 105 may be similar to the respiration signal detected by the pressure sensor 124 (FIG. 4) and described above in conjunctions with FIGS. 1-11. The $CO_2$ sensor 105, for example, may include an IR light emitter and an IR light detector. In this regard, it is known that $CO_2$ absorbs light in the IR energy spectrum. See, for example, U.S. Pat. No. 4,648,396 to Raemer, the contents of which are fully incorporated herein by reference. Hence, when a breathing gas has higher concentrations of $CO_2$, less IR light is received by the IR detector than when $CO_2$ concentrations are lower. Since $CO_2$ concentrations in the breathing gas are higher during exhalation and lower during inhalation, the detected respiration signal from the $CO_2$ sensor 105 may be indicative of respiration (i.e., patient breathing).

The detected respiration signal from the $CO_2$ sensor 105 may be communicated to the noise suppression filter 126 (FIG. 4). In other embodiments of PAP devices, a $CO_2$ sensor and supporting components may be implemented in other arrangements to produce the detected respiration signal. For additional information on other arrangements for a $CO_2$ sensor and supporting components in other embodiments of PAP devices see U.S. Pat. No. 6,990,980. Any of the aspects of FIG. 12 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 12.

With reference to FIG. 13, yet another embodiment of an exemplary PAP device 100" may include a pressure control loop circuit 102', a respiratory checks logic 104", a pressure modify logic 106, a mask 111, and an interconnect plenum 113, such as a hose. The pressure control loop circuit 102' may include the same components and may function in the essentially the same manner as described above for the pressure control loop circuit 102' of FIG. 12. The pressure modify logic 106 may include the same components and may function in the essentially the same manner as described above for the pressure modify logic 106 of FIG. 4.

The respiratory checks logic 104" may include the components described above for the respiratory checks logic 104 of FIG. 4, except the pressure sensor 124 may not be included in this embodiment. Additionally, the respiratory checks logic 104" may include a $CO_2$ sensor 115, an input conduit 117, an output conduit 119, a vacuum pump 121, and an outlet conduit 123. In this embodiment, during normal operation of the PAP device 100", breathing gas may be drawn into the inlet by the blower 110 (FIG. 4) and pressurized breathing gas may flow to a user airway associated with an interior of the mask 111 via the interconnect plenum 113. Additionally, the vacuum pump 121 may draw gas from the interior of the mask 111 into the input conduit 117 through the $CO_2$ sensor 115 and output conduit 119. The vacuum pump 121 expels this gas in its exhaust via outlet conduit 123. Some pressurized breathing gas may flow through the input conduit 117, $CO_2$ sensor 115, output conduit 119, vacuum pump 121, and output conduit 123. Generally, the input and output conduits 117, 119 may be sized so that any amount of pressurized gas that escapes or leaks through the outlet associated with the vacuum pump 121 during inhalation may be considered negligible in relation to the overall flow of breathing gas to the patient.

During exhalation, $CO_2$-rich gas may be exhaled into the mask by the patient and may be drawn into the input conduit 117 and through the $CO_2$ sensor 105. As shown, an inlet end of the input conduit 117 may be suitably positioned by feeding it into the interconnect plenum 113 and along the interior of the interconnect plenum 113 to the interior of the mask 111. The $CO_2$ sensor 105, for example, may be any sensor suitable detecting concentrations of $CO_2$ during in a normal exhalation phase of a user's breathing cycle. For example, various types of $CO_2$ sensors may include any of the various IR light emitters and detectors such as those employed by a PAP device disclosed in U.S. Pat. No. 6,990,980 to Richey II and assigned to Invacare Corporation, the contents of which are fully incorporated herein by reference. The $CO_2$ sensor 115 may produce a detected respiration signal based at least in part on a level of $CO_2$ within the gas passing through the $CO_2$ sensor 115. The detected respiration signal from the $CO_2$ sensor 105 may be similar to the respiration signal detected by the pressure sensor 124 (FIG. 4) and described above. Accordingly, the detected respiration signal may be communicated to the noise suppression filter 126 (FIG. 4). Pump 121, for example, may be model no. NMP02 from KNF Neuberger, Inc. of Trenton, N.J.

In one embodiment, the vacuum pump 121 may be operated whenever the PAP device 100" is operated. In other embodiments, the vacuum pump 121 may be operated when the blower motor 122 is operated or at least in relation to the exhalation periods of breathing cycles. Generally, the vacuum pump 121 may be operated at a relatively constant speed. However, in other embodiments, the speed of the vacuum pump 121 may be controlled so that gas flow through the outlet associated with the vacuum pump 121 is reduced in relation to inhalation periods of breathing cycles. In another embodiment, the vacuum pump 121 and outlet conduit 123 may not be included. In this embodiment, the output conduit 119 may be suitably positioned in relation to the input to the blower 110 (FIG. 4) such that a venturi effect associated with operation of the blower 110 (FIG. 4) draws sufficient gas through the $CO_2$ sensor 115. In other embodiments of PAP devices, a $CO_2$ sensor and supporting components may be implemented in other arrangements to produce the detected respiration signal. For additional information on other arrangements for a $CO_2$ sensor and supporting components in other embodiments of PAP devices see U.S. Pat. No. 6,990, 980. Any of the aspects of FIG. 13 described above may be automated, semi-automated, or manual and may be implemented through hardware, software, firmware, or combinations thereof. ADCs or DACs may be accomplished within components, such as sensors, input/output devices, or input/ output ports of a controller or processor, particularly where software or firmware are used to implement certain aspects of FIG. 13.

With reference to FIG. 14, yet another embodiment of an exemplary PAP device 100''' may include a pressure control loop circuit 102, a respiratory checks logic 104, and a pressure modify logic 106'''. The pressure control loop circuit 102 may include the same components and may function in the essentially the same manner as described above for the pressure control loop circuit 102 of FIG. 4. The respiratory checks logic 104 may include the same components and may function in the essentially the same manner as described above for the respiratory checks logic 104 of FIG. 4.

The pressure modify logic 106''' may include the components described above for the pressure modify logic 106 of FIG. 4 and may also include a SoftX™ pressure adjust circuit 125 and a SoftX™ subtractor 127. The SoftX™ pressure adjust circuit 125 may include an inverter 129, a SoftX™ timing logic 131, and a SoftX™ decrease pressure logic 133. The inverter 129 may be in operative communication with the respiratory checks logic 104 to receive the filtered respiration signal produced by the noise suppression filter 126 (FIG. 4). Additionally, the inverter 129 may produce an inverted respiration signal. The SoftX™ timing logic 131 is in operative communication with the inverter 129 to receive the inverted respiration signal. Additionally, the SoftX™ timing logic 131 may determine an appropriate duration for a first portion of each exhalation period of each breathing cycle in which the desired (target) pressure may be softened or reduced. The SoftX™ decrease pressure logic 133 is in operative communication with the SoftX™ timing logic 131. Additionally, the SoftX™ decrease pressure logic 133 may determine an appropriate reduction of the desired pressure during the first portion of each exhalation period, including an initial maximum reduction and gradual adjustments to the reduction until a second portion of the corresponding exhalation period when the desired pressure may be provided without reduction.

The SoftX™ subtractor 127 may be in operative communication with the SoftX™ pressure adjust circuit 125 and the mode switch 144 (FIG. 4) to receive the desired pressure signal and the appropriate reduction to the desired pressure, respectively. Additionally, the SoftX™ subtractor 127 may overlay the appropriate reduction on the desired pressure signal to produce a desired pressure signal with SoftX™. The desired pressure signal with SoftX™ may be communicated to the subtractor 114 (FIG. 4) in the pressure control loop circuit 102.

Other embodiments may implement other SoftX™ control schemes. For additional information describing various SoftX™ control schemes refer to U.S. Patent Application Publication Nos. 2004/0255943 and 2005/0268913, Ser. Nos. 10/601,720 and 11/157,089, respectively, both to Morris et al. and commonly assigned to Invacare Corporation, the contents of which are fully incorporated herein by reference. Any of the aspects of FIG. 14 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 14.

With reference to FIG. 15, still another embodiment of an exemplary PAP device 100'''' may include a pressure control loop circuit 102'''', a respiratory checks logic 104'''', and a pressure modify logic 106'''. The pressure modify logic 106''' may include the same components and may function in the same manner as described above for the pressure modify logic 106''' of FIG. 14. The pressure control loop circuit 102'''' may include the components described above for the pressure control loop circuit 102 of FIG. 4, except blower motor power or blower motor speed signals may be communicated from the blower motor 122 to the respiratory checks logic 104''''.

The respiratory checks logic 104''' may include the components described above for the respiratory checks logic 104 of FIG. 4, except the pressure sensor 124 may not be included in this embodiment. Additionally, respiratory checks logic 104''' may include a blower motor sensing logic 135. The blower motor sensing logic 135 may be in operative communication with the blower motor 122 to receive the blower motor power or blower motor speed signals. The blower motor sensing logic 135 may produce a detected respiration signal based at least in part on blower motor power or blower motor speed signals. The detected respiration signal from the blower motor sensing logic 135 may be similar to the respiration signal detected by the pressure sensor 124 (FIG. 4) and described above. Accordingly, the detected respiration signal may be communicated to the noise suppression filter 126 (FIG. 4). Any of the aspects of FIG. 15 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 15.

With reference to FIG. 16, an embodiment of an exemplary process 300 for adjusting a desired pressure in a PAP device starts at 301. This process 300, for example, may be initiated in conjunction with a normal power-up sequence or a normal reset sequence. The PAP device, for example, may be configured as a CPAP device (i.e., standard CPAP, CPAP with SoftX™, etc.), a BiPAP device, a PPAP device, an auto-titrating PAP device, a ventilator device, a gas therapy device, an oxygen therapy device, or another type of PAP device. Next, operation of the PAP device may be initialized (302). At 303, the current desired pressure may be set to a predetermined startup pressure. Next, at 304, a blower may be operated to pressurize the breathing gas. Next, breathing gas under positive pressure may be provided to a patient via the PAP device based at least in part on a current desired pressure (305). At 306, a characteristic of the breathing gas, a physiological characteristic of the patient, or a characteristic of the PAP device that is indicative of respiration may be monitored. Pressure, flow, flow rate, temperature, humidity, $O_2$, and $CO_2$ are examples of characteristics of the breathing gas that may be indicative of respiration. For example, any of the characteristics monitored during a PSG are examples of patient physiological characteristics that may be indicative of respiration. Blower motor Hall effect, blower motor voltage or current, blower motor speed, breathing gas valve position, and breathing gas vent position are examples of characteristics associated with the PAP device that may be indicative of respiration. Of course, any combination of such breathing gas characteristics, PAP device characteristics, and patient physiological characteristics may be monitored.

Monitoring a characteristic that is indicative of respiration provides a monitored respiration characteristic. Next, a breathing cycle signal having a first level associated with inhalation and a second level different from the first level and associated with exhalation may be created (308). The breathing cycle signal may be based at least in part on the monitored respiration characteristic. In one embodiment, the first and second levels of the breathing cycle signal may correspond to voltage levels associated with opposing digital signal logic levels.

At 310, one or more abnormal breathing checks based at least in part on the monitored respiration characteristic or the breathing cycle signal may be performed. In one embodiment, the one or more abnormal breathing checks include at least one of an apnea check, an irregular breathing cycle check, an irregular inhalation period check, a PFL check, a slow breathing check, a fast breathing check, and a hypopnea check. In one embodiment, at least one abnormal breathing check may be based at least in part on the monitored respiration characteristic and the breathing cycle signal during a single breathing cycle (e.g., apnea check, PFL check, slow breathing check, fast breathing check, hypopnea check, etc.). In another embodiment, at least one abnormal breathing check may be based at least in part on the monitored respiration characteristic and the breathing cycle signal during two consecutive breathing cycles (e.g., irregular breathing cycle check, irregular inhalation period check, etc.). Next, the process may determine if abnormal breathing was detected (312). If abnormal breathing was not detected, at 314, the process may determine if the current desired pressure is at the minimum desired pressure. If the current desired pressure is not at the minimum desired pressure, the current desired pressure may be decreased (316). This decrease may be a prompt decrease in target pressure (as shown) or may be a more gradual reduction, such as a gradual ramp down of target pressure in the absence of abnormal breathing. Next, the process returns to 305.

If abnormal breathing was not detected at 312, the process may determine if the current desired pressure is at the maximum desired pressure (320). If the current desired pressure is not at the maximum desired pressure, the current desired pressure may be increased (322). Next, the process returns to 305. In one embodiment, each incremental increasing (322) or decreasing (316) of the current desired pressure may be associated with transition of the breathing cycle signal from the second level to the first level.

If the current desired pressure is at the minimum desired pressure at 314, the current desired pressure may be left at the minimum desired pressure and the process returns to 305. Similarly, if the current desired pressure is at the maximum desired pressure at 322, the current desired pressure may be left at the maximum desired pressure and the process returns to 305.

It is understood that items 305, 306, 308, and 310 may be independent tasks that may initiated in the sequence shown and then may continuously operate during operation of the process 300. Overall control of the process 300 to adjust the desired pressure and these independent tasks may be interrupted and ended by any suitable mechanism or process for resetting or shutting down the PAP device. Any such reset or shutdown process may end the process 300 and independent tasks in an orderly fashion, for example, to preserve data and settings for subsequent operation. Any of the aspects of FIG. 16 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 16.

With reference to FIG. 17, an embodiment of an exemplary process 305 for providing a breathing gas to a patient based on a desired pressure begins at 338 where a characteristic of the breathing gas indicative of breathing gas pressure may be monitored. Next, at 340, a variable mechanism of the PAP device may be controlled using a closed loop control process based at least in part on a difference between the current desired pressure and the monitored pressure characteristic to reduce the difference. Next, the process may determine if a runaway low pressure condition exists (342). A runaway low pressure condition may be caused by an improper fit between a patient interface and the patient or when the patient interface is not being worn by a patient. If a runaway low pressure condition is not detected, at 344, the current desired pressure may be adjusted based at least in part on a currently-selected operating mode associated with the PAP device. Conversely, if a runaway low pressure condition is detected, the process may advance to 346 where the current desired pressure may be reset to a predetermined reset pressure, such as the startup pressure associated with 303 (FIG. 16).

In another embodiment, at 344, the current desired pressure may be adjusted based at least in part on at least one of a currently-selected operating mode for the PAP device and a corresponding desired pressure profile. In one embodiment, the desired pressure profile may correspond to a breathing cycle and may include a first desired pressure associated with at least a portion of inhalation and a second desired pressure associated with at least a portion of exhalation. In this embodiment, the second desired pressure may be less than the first desired pressure. In another embodiment, the desired pressure profile may correspond to a ramp period and may include a first desired pressure associated with a time when the patient is presumed awake, a second desired pressure associated with a time when the patient is presumed asleep, and a ramp function to adjust the current desired pressure over the ramp period in relation to ramping from the first desired pressure to the second desired pressure. In this embodiment, the first desired pressure may be less than the second desired pressure. In other embodiments, these exemplary pressure profiles may be combined together or with other pressure profiles associated with various operations of the PAP device.

The process 305 continuously operate while the overall process 300 (FIG. 16) is operating. The overall process 300 (FIG. 16) may utilize certain effects resulting from operation of the process 305, for example, in conjunction with 306 (FIG. 16). Any of the aspects of FIG. 17 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 17.

With reference to FIG. 18, an embodiment of an exemplary process 308 for creating a breathing cycle signal begins at 352 where a start of inhalation may be detected based at least in part on a first transition of the monitored respiration characteristic in relation to a first predetermined threshold. Next, in response to detecting the start of inhalation, the breathing cycle signal may be set to the first level (354). At 356, an end of inhalation may be detected based at least in part on a second transition of the monitored respiration characteristic in relation to a second predetermined threshold. Next, in response to detecting the end of inhalation, the breathing cycle signal may be set to the second level (358). At 352, if the start of inhalation is not detected, the process 308 may bypass adjusting the breathing cycle signal in 354 and advance to 356. Similarly, at 356, if the end of inhalation is not detected, the process 308 may bypass adjusting the breathing cycle signal in 358.

The process 308 may continuously operate while the overall process 300 (FIG. 16) is operating. The overall process (FIG. 16) may utilize certain effects resulting from operation of the process 308, for example, in conjunction with the abnormal breathing check(s) process 310 (FIG. 16). Any of the aspects of FIG. 18 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 18.

With reference to FIG. 19, an embodiment of an exemplary process 310 for performing one or more abnormal breathing checks that may include performing any combination of at least seven exemplary checks. The seven exemplary abnormal breathing checks include an apnea check (362), an irregular breathing cycle check (364), an irregular inhalation period check (366), a PFL check (368), a slow breathing check (370), a fast breathing check (372), and a hypopnea check (374). Each of these seven exemplary abnormal breathing checks is discussed in more detail below in reference to FIGS. 18-25. It is understood that each abnormal breathing check may be an independent task. Each abnormal breathing check may essentially be performed in parallel, for example, via parallel processors or parallel execution using a task scheduler. In other embodiments, multiple abnormal breathing checks may share common processes while processes that are not common may operate independently. Moreover, any one or any two or more of the routines in FIG. 19 may be used in exemplary systems. Exemplary systems, for example, may only need a single instance of "operate system timer" (see FIG. 21, item 404; FIG. 22, item 434; FIG. 23, item 464; FIG. 24, item 494; FIG. 25, item 514) if two or more routines using that timer are used together. Although the routines in FIG. 19 are shown as executing in parallel (i.e., independently), they may very well be executed in a serial fashion, as shown in the exemplary embodiments of FIGS. 28-39.

Any combination of the exemplary breathing checks for process 310 may continuously operate while the overall process 300 (FIG. 16) may utilize certain effects resulting from operation of the exemplary breathing checks, for example, in conjunction with 312 (FIG. 16). Any of the aspects of FIG. 19 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 19.

With reference to FIG. 20, an embodiment of an exemplary process 362 for performing an apnea check begins with monitoring a breathing cycle signal (382) and operating a free running counter (384) having a count value that changes over time. At 386, the process may determine if the count value exceeds an apnea threshold (e.g., a count indicating no respiration for ten seconds). If the count value exceeds the apnea threshold, abnormal breathing is detected based on the apnea check (388). If the count value does not exceed the apnea threshold at 386, the process did not detect abnormal breathing for a breathing cycle. During operation of the free running counter, the process may determine if the breathing cycle signal transitions from the second level to the first level (390). Such a transition is related to the start of an inhalation period for a new breathing cycle. In response to each transition of the breathing cycle signal from the second level to the first level, at 392, the count value of the free running counter (384) may be reset. Otherwise, the process may continue from 390 to 384 without resetting the free running counter.

The apnea check process 362 may continuously operate while the overall process 300 (FIG. 16) is operating. The overall process 300 (FIG. 16) may utilize certain effects resulting from operation of the apnea check process 362, for example, in conjunction with 312-322 (FIG. 16). Similarly, the abnormal breathing check(s) process 310 may utilize certain results or information from the apnea check process 362, for example, in conjunction with another abnormal breathing check (e.g., any of 364-374 or any combination thereof). Any of the aspects of FIG. 20 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 20.

With reference to FIG. 21, an embodiment of an exemplary process 364 for performing an irregular breathing cycle check begins with monitoring a breathing cycle signal (402) and operating a system timer (404) having a timer value that changes over time. At 406, the process may determine if the breathing cycle signal transitions from the second level to the first level. Such a transition is related to the start of a new breathing cycle. In response to transition of the breathing cycle signal from the second level to the first level, at 408, the current timer value may be stored in a first storage location to identify a start time for a current breathing cycle.

Next, the process may determine a running breathing cycle time based at least in part on a difference between the start time and the current timer value (410). In response to transition of the breathing cycle signal from the second level to the first level, at 412, the running breathing cycle time may be stored in a second storage location to store a current breathing cycle time. In response to transition of the breathing cycle signal from the second level to the first level, at 414, the current breathing cycle time may be stored in a third storage location to store a previous breathing cycle time. At 406, if the breathing cycle signal did not transition from the second level to the first level, the process may continue to 404 without changing the values stored in the first, second, and third storage locations.

Next, the process may determine a variance between consecutive breathing cycle times based at least in part on a difference between the previous breathing cycle time and the current breathing cycle time (416). At 418, an absolute value function may be applied to the variance. Next, the process may determine if the absolute value of the variance exceeds an irregular breathing cycle threshold (420). At 422, if the absolute value exceeds the irregular breathing cycle threshold, abnormal breathing is detected based on the irregular breathing cycle check. If the absolute value does not exceed the irregular breathing cycle threshold at 420, the process did not detect abnormal breathing in consecutive breathing cycles.

The irregular breathing cycle check process 364 may continuously operate while the overall process 300 (FIG. 16) is operating. The overall process 300 (FIG. 16) may utilize certain effects resulting from operation of the irregular breathing cycle check process 364, for example, in conjunction with 312-322 (FIG. 16). Similarly, the abnormal breathing check(s) process 310 may utilize certain results or information from the irregular breathing cycle check process 364, for example, in conjunction with another abnormal breathing check (e.g., any of 362 and 366-374 or any combination thereof). Any of the aspects of FIG. 21 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 21.

With reference to FIG. 22, an embodiment of an exemplary process 366 for performing an irregular inhalation period check begins with monitoring a breathing cycle signal (432) and operating a system timer (434) having a current timer value that changes over time. At 436, the process may determine if the breathing cycle signal transitions from the second level to the first level. Such a transition is related to the start of a new inhalation period for a new breathing cycle. In response to transition of the breathing cycle signal from the second level to the first level, at 438, the current timer value may be stored in a first storage location to identify a start time for a current inhalation period.

Next, the process may determine a running inhalation period time based at least in part on a difference between the start time and the current timer value (440). At 442, the process may determine if the breathing cycle signal transitions from the first level to the second level. Such a transition is related to the end of the new inhalation period. In response to transition of the breathing cycle signal from the first level to the second level, at 444, the running inhalation period time may be stored in a fourth storage location to store a current inhalation period time. In response to transition of the breathing cycle signal from the first level to the second level, at 446, the current inhalation period time may be stored in a fifth storage location to store a previous inhalation period time. At 436, if the breathing cycle signal did not transition from the second level to the first level, the process may continue to 434 without changing the values stored in the first, fourth, and fifth storage locations.

Next, the process may determine a variance between consecutive inhalation period times based at least in part on a difference between the previous inhalation period time and the current inhalation period time (448). At 450, an absolute value function may be applied to the variance. Next, the process may determine if the absolute value of the variance exceeds an irregular inhalation period threshold (452). At 454, if the absolute value exceeds the irregular inhalation period threshold, abnormal breathing is detected based on the irregular inhalation period check. At 442, if the breathing cycle signal did not transition from the first level to the second level, the process may continue to 448 without changing the values stored in the fourth and fifth storage locations. At 452, if the absolute value does not exceed the irregular inhalation period threshold, the process did not detect abnormal breathing during consecutive breathing cycles.

The irregular inhalation period check process 366 may continuously operate while the overall process 300 (FIG. 16) is operating. The overall process 300 (FIG. 16) may utilize certain effects resulting from operation of the irregular inhalation period check process 366, for example, in conjunction with 312-322 (FIG. 16). Similarly, the abnormal breathing check(s) process 310 may utilize certain results or information from the irregular inhalation period check process 366, for example, in conjunction with another abnormal breathing check (e.g., any of 362, 364, and 368-374 or any combination thereof). Any of the aspects of FIG. 22 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 22.

With reference to FIG. 23, an embodiment of an exemplary process 368 for performing a PFL check begins with monitoring a breathing cycle signal (462) and operating a system timer (464) having a current timer value that changes over time. At 466, the process may determine if the breathing cycle signal transitions from the second level to the first level. Such a transition is related to the start of a new inhalation period for a new breathing cycle. In response to transition of the breathing cycle signal from the second level to the first level, at 468, the current timer value may be stored in a first storage location to identify a start time for a current breathing cycle and a current inhalation period time.

Next, the process may determine a running breathing cycle time based at least in part on a difference between the start time and the current timer value (470). In response to transition of the breathing cycle signal from the second level to the first level, at 472, the running breathing cycle time may be stored in a second storage location to store a current breathing cycle time. Next, the process may determine a running inhalation period time based at least in part on a difference between the start time and the current timer value (474). At 476, the process may determine if the breathing cycle signal transitions from the first level to the second level. Such a transition is related to the end of the new inhalation period. In response to transition of the breathing cycle signal from the first level to the second level, at 478, the running inhalation period time may be stored in a fourth storage location to store a current inhalation period time. At 466, if the breathing cycle signal did not transition from the second level to the first level, the process may continue to 464 without changing the values stored in the first, second, and fourth storage locations.

Next, the process may determine a ratio of the current inhalation period time to the current breathing cycle time (480). At 482, the process may determine if the ratio exceeds a PFL threshold. If the ratio exceeds the PFL threshold, abnormal breathing is detected based on the PFL check (484). At 476, if the breathing cycle does not transition from the first level to the second level, the process may continue to 480 without changing the value stored in the fourth storage location. At 482, if the ratio does not exceed the PFL threshold, the process did not detect abnormal breathing for a breathing cycle.

The PFL check process 368 may continuously operate while the overall process 300 (FIG. 16) is operating. The overall process 300 (FIG. 16) may utilize certain effects resulting from operation of the PFL check process 368, for example, in conjunction with 312-322 (FIG. 16). Similarly, the abnormal breathing check(s) process 310 may utilize certain results or information from the PFL check process 368, for example, in conjunction with another abnormal breathing check (e.g., any of 362-366 and 370-374 or any combination thereof). Any of the aspects of FIG. 23 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 23.

With reference to FIG. 24, an embodiment of an exemplary process 370 for performing a slow breathing check begins with monitoring a breathing cycle signal 492 and operating a system timer 494 having a current timer value that changes over time. At 496, the process may determine if the breathing cycle signal transitions from the second level to the first level. Such a transition is related to the start of a new breathing cycle. In response to transition of the breathing cycle signal from the second level to the first level, at 498, the current timer value may be stored in a first storage location to identify a start time for a current breathing cycle.

Next, the process may determine a running breathing cycle time based at least in part on a difference between the start time and the current timer value (500). In response to transition of the breathing cycle signal from the second level to the first level, at 502, the running breathing cycle time may be stored in a second storage location to store a current breathing cycle time. At 496, if the breathing cycle signal did not transition from the second level to the first level, the process may continue to 494 without changing the values stored in the first and second storage locations.

Next, the process may determine if the current breathing cycle time exceeds a maximum threshold (504). At 506, if the current breathing cycle time exceeds the maximum threshold, abnormal breathing is detected based on the slow breathing check. If the current breathing cycle does not exceed the maximum threshold at 504, the process did not detect abnormal breathing for a breathing cycle.

The slow breathing check process 370 may continuously operate while the overall process 300 (FIG. 16) is operating. The overall process 300 (FIG. 16) may utilize certain effects resulting from operation of the slow breathing check process 370, for example, in conjunction with 312-322 (FIG. 16). Similarly, the abnormal breathing check(s) process 310 may utilize certain results or information from the slow breathing check process 370, for example, in conjunction with another abnormal breathing check (e.g., any of 362-368, 372, and 374 or any combination thereof). Any of the aspects of FIG. 24 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 24.

With reference to FIG. 25, an embodiment of an exemplary process 372 for performing a fast breathing check begins with monitoring a breathing cycle signal 512 and operating a system timer 514 having a current timer value that changes over time. At 516, the process may determine if the breathing cycle signal transitions from the second level to the first level. Such a transition is related to the start of a new breathing cycle. In response to transition of the breathing cycle signal from the second level to the first level, at 518, the current timer value may be stored in a first storage location to identify a start time for a current breathing cycle.

Next, the process may determine a running breathing cycle time based at least in part on a difference between the start time and the current timer value (520). In response to transition of the breathing cycle signal from the second level to the first level, at 522, the running breathing cycle time may be stored in a second storage location to store a current breathing cycle time. At 516, if the breathing cycle signal did not transition from the second level to the first level, the process may continue to 514 without changing the values stored in the first and second storage locations.

Next, the process may determine if the current breathing cycle time is less than a minimum threshold (524). At 526, if the current breathing cycle time is less than the minimum threshold, abnormal breathing is detected based on the fast breathing check. If the current breathing cycle is not less than the minimum threshold at 524, the process did not detect abnormal breathing for a breathing cycle.

The fast breathing check process 372 may continuously operate while the overall process 300 (FIG. 16) is operating.

The overall process 300 (FIG. 16) may utilize certain effects resulting from operation of the fast breathing check process 372, for example, in conjunction with 312-322 (FIG. 16). Similarly, the abnormal breathing check(s) process 310 may utilize certain results or information from the fast breathing check process 372, for example, in conjunction with another abnormal breathing check (e.g., any of 362-370 and 374 or any combination thereof). Any of the aspects of FIG. 25 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 25.

With reference to FIG. 26, an embodiment of an exemplary process 374 for performing a hypopnea check begins with creating a filtered respiration signal based at least in part on bandpass filtering the monitored respiration characteristic (532) and monitoring a breathing cycle signal (534). Next, a triggered respiration signal with a first level associated with a positive surge and a second level different from the first level and associated with a negative surge may be created (536). The triggered respiration signal being based at least in part on the filtered respiration signal. In one embodiment, the first and second levels of the triggered respiration signal may correspond to voltage levels associated with opposing digital signal logic levels. At 538, the process may determine if the breathing cycle signal transitions from the second level to the first level. Such a transition is related to the start of a new inhalation period for a new breathing cycle. In response to transition of the breathing cycle signal from the second level to the first level, at 540, a positive surge counter and a negative surge counter may be cleared to reset the hypopnea check at the start of each breathing cycle.

At 542, the triggered respiration signal may be monitored. Next, the process may determine if the triggered respiration signal transitions from the second level to the first level (544). Such a transition is related to a positive surge in the monitored respiration characteristic during the inhalation period. Each time the triggered respiration signal transitions from the second level to the first level, the positive surge counter may be incremented to count the positive surge (546). Next, the process may determine if the triggered respiration signal transitions from the first level to the second level (548). Such a transition is related to a negative surge in the monitored respiration characteristic during the inhalation period. Each time the triggered respiration signal transitions from the first level to the second level, the negative surge counter may be incremented to count the positive surge (550). If the triggered respiration signal did not transition from the second level to the first level, the process may advance to 548 to respond to a transition from the first level to the second level. Similarly, at 548, if the triggered respiration signal did not transition from the first level to the second level, the process may advance to 552. At 552, the process may determine if the positive and negative surge counter have been read during for the current breathing cycle. Normally, the counters are operated in relation to the inhalation period and read in relation to transition from the inhalation period to the exhalation period. If the surge counters have not been read, from 552, the process returns to 542 to continue monitoring the triggered respiration signal. Otherwise, monitoring of the triggered respiration signal may be ended until the next iteration of the hypopnea check process 374 is performed for the next breathing cycle.

At 554, the process may determine if the breathing cycle signal transitions from the first level to the second level. Such a transition is related to the end of the new inhalation period. In response to transition of the breathing cycle signal from the first level to the second level, at 556, the positive surge counter and the negative surge counter may be read. Next, the process may determine if the positive surge count is not equal to zero or the negative surge count is not equal to one (558). If either the positive surge count is not equal to zero or the negative surge count is not equal to one, abnormal breathing is detected based on the hypopnea check (560). If the positive surge count is equal to zero and the negative surge count is equal to one, the process did not detect abnormal breathing during the current breathing cycle. At 538, if the breathing cycle signal did not transition from the second level to the first level, the process may advance to 554. Similarly, at 554, if the breathing cycle signal did not transition from the first level to the second level, the process may advance to 558.

The hypopnea check process 374 may continuously operate while the overall process 300 (FIG. 16) is operating. The overall process 300 (FIG. 16) may utilize certain effects resulting from operation of the hypopnea check process 374, for example, in conjunction with 312-322 (FIG. 16). Similarly, the abnormal breathing check(s) process 310 may utilize certain results or information from the hypopnea check process 374, for example, in conjunction with another abnormal breathing check (e.g., any of 362-372 or any combination thereof). Any of the aspects of FIG. 26 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 26.

With reference to FIG. 27, an embodiment of an exemplary process 536 for creating a triggered respiration signal begins at 562 where a positive surge may be detected based at least in part on a first transition of the filtered respiration signal in relation to a first predetermined threshold. Next, in response to detecting the positive surge, the triggered respiration signal may be set to the first level (564). At 566, a negative surge may be detected based at least in part on a second transition of the filtered respiration characteristic in relation to a second predetermined threshold. Next, in response to detecting the negative surge, the triggered respiration signal may be set to the second level (358). At 562, if no positive surge on the filtered respiration signal is detected, the process 536 may bypass adjusting the triggered respiration signal in 564 and advance to 566. Similarly, at 566, if no negative surge on the filtered respiration signal is detected, the process 536 may bypass adjusting the triggered respiration signal in 568 and return to the hypopnea check process 374 (FIG. 26).

The process 536 may continuously operate while the overall process 300 (FIG. 16) and the hypopnea check process 374 (FIG. 26) are operating. The overall process 300 (FIG. 16) or the hypopnea check process 374 (FIG. 26) may utilize certain effects resulting from operation of the process 536, for example, in conjunction with 312-322 (FIG. 16) or 542-552 (FIG. 26). Any of the aspects of FIG. 27 described above may be automated, semi-automated, or manual and may be implemented through hardware, software, firmware, or combinations thereof. ADCs or DACs may be accomplished within components, such as sensors, input/output devices, or input/output ports of a controller or processor, particularly where software or firmware are used to implement certain aspects of FIG. 27.

FIG. 28 provides a block diagram of an embodiment of an exemplary PAP device. This embodiment is similar to the embodiment described above in reference to FIG. 4.

FIGS. 29-33 provide another embodiment of an exemplary PAP device with respect to the flow charts of FIGS. 16-27. This embodiment shows alternate arrangements for FIGS. 18, 20, 21, 26, and 27. Alternate arrangements for FIGS. 22-25 are also envisioned. These alternate arrangements would modify FIGS. 22-25 in similar fashion to the alternate arrangements of FIGS. 20 and 21. The reference numbers used in FIGS. 29-33 correspond to the reference numbers used in FIGS. 16-27.

FIGS. 34-39 provide yet another embodiment of an exemplary PAP device with respect to the flow charts of FIGS. 16-27. This embodiment shows alternate arrangements for FIGS. 16-20 and 26. Alternate arrangements for FIGS. 21-25 are also envisioned. These alternate arrangements would modify FIGS. 21-25 in similar fashion to the alternate arrangement of FIG. 20. The reference numbers used in FIGS. 34-39 correspond to the reference numbers used in FIGS. 16-27.

While the invention is described herein in conjunction with one or more exemplary embodiments, it is evident that many alternatives, modifications, and variations will be apparent to those skilled in the art. For example, the exemplary embodiments herein may be modified to provide an index of detected breathing events, such as an apnea-hypopnea index (AHI) or some other index. This may take the form of a count of apnea and hypopnea events per hour, and/or a count of any of the other detected breathing events herein, such as persistent flow limitations, etc. For example, an AHI counter may increment on every "hypopnea" event (e.g., the waveform checks, above, or a more traditional hypopnea detection such as a decrease in the area of the flow curve during inhalation below a predetermined threshold) and on every "apnea" event (cessation of respiratory activity for a predetermined time period). Exemplary systems may allow optional inclusion of any one or any two or more of the other pressure-increasing events such as "PFL", breath cycle time, deviation checks etc. to increment this counter (or separate counter(s)) as well. Since an "AHI" index denotes "apnea" and "hypopnea" only, the AHI index may be limited to apea and hypopnea events and other indexes may also be generated and presented to a user that include these other detected events. The final index values may be the number of counted events per hour, or over some other measure of time. Exemplary embodiments may also in addition, or in the alternative, count events for a shorter period of time, e.g., one minute, and scale back to an hour, e.g., multiply by 60, to get a momentary AHI reading or other momentary index reading. Accordingly, exemplary embodiments in the preceding description are intended to be illustrative, rather than limiting, of the spirit and scope of the invention. More specifically, it is intended that the invention embrace all alternatives, modifications, and variations of the exemplary embodiments described herein that fall within the spirit and scope of the appended claims or the equivalents thereof. Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

The invention claimed is:

1. A method for adjusting a desired pressure in a positive airway pressure device, the method comprising:

a) providing a breathing gas under positive pressure to a patient via a positive airway pressure device based at least in part on a current desired pressure;
b) monitoring a characteristic of the breathing gas that is indicative of respiration;
c) creating a breathing cycle signal with a first level associated with inhalation and a second level different from the first level and associated with exhalation, the breathing cycle signal being based at least in part on the monitored respiration characteristic;
d) performing one or more abnormal breathing checks based at least in part on the monitored respiration characteristic and the breathing cycle signal, wherein one or more abnormal breathing checks comprises a hypopnea check, the hypopnea check comprising:
   creating a filtered respiration signal based at least in part on bandpass filtering the monitored respiration characteristic;
   monitoring the breathing cycle signal;
   clearing a positive surge counter and a negative surge counter each time the breathing cycle signal transitions from the second level to the first level to reset the hypopnea check at a start of each breathing cycle;
   creating a triggered respiration signal with a first level associated with a positive surge and a second level different from the first level and associated with a negative surge, the triggered respiration signal being based at least in part on the filtered respiration signal;
   monitoring the triggered respiration signal;
   incrementing the positive surge counter each time the triggered respiration signal transitions from the second level to the first level to count a positive surge after an initial positive surge associated with inhalation;
   incrementing the negative surge counter each time the triggered respiration signal transitions from the first level to the second level to count a negative surge;
   reading the positive surge counter and the negative surge counter each time the breathing cycle signal transitions from the first level to the second level;
   determining if the positive surge count is not equal to zero or the negative surge count is not equal to one; and
   if either the positive surge count is not equal to zero or the negative surge count is not equal to one, abnormal breathing is detected based on the hypopnea check; and
e) if abnormal breathing is detected, increasing the current desired pressure by a first increment until a maximum desired pressure is reached, otherwise, decreasing the current desired pressure by a second increment until a minimum desired pressure is reached.

2. The method of claim 1, a) further comprising:
f) monitoring a characteristic of the breathing gas indicative of breathing gas pressure and
g) controlling a variable mechanism of the positive airway pressure device using a closed loop control process based at least in part on a difference between the current desired pressure and the monitored pressure characteristic to reduce the difference.

3. The method of claim 1 wherein the current desired pressure is based at least in part on a desired pressure profile.

4. The method of claim 3 wherein the desired pressure profile corresponds to a breathing cycle and comprises a first desired pressure associated with at least a portion of inhalation and a second desired pressure associated with at least a portion of exhalation, the second desired pressure being less than the first desired pressure.

5. The method of claim 3 wherein the desired pressure profile corresponds to a ramp period and comprises a first desired pressure associated with a time when the patient is presumed awake, a second desired pressure associated with a time when the patient is presumed asleep, and a ramp function to adjust the current desired pressure over the ramp period in relation to ramping from the first desired pressure to the second desired pressure, the first desired pressure being less than the second desired pressure.

6. The method of claim 1, c) further comprising:
   f) detecting a start of inhalation based at least in part on a first transition of the monitored respiration characteristic in relation to a first predetermined threshold;
   g) in response to detecting the start of inhalation, setting the breathing cycle signal to the first level;
   h) detecting an end of inhalation based at least in part on a second transition of the monitored respiration characteristic in relation to a second predetermined threshold; and
   i) in response to detecting the end of inhalation, setting the breathing cycle signal to the second level.

7. The method of claim 1 wherein at least one of the one or more abnormal breathing checks is based at least in part on the monitored respiration characteristic and the breathing cycle signal during a single breathing cycle.

8. The method of claim 1 wherein d) further comprises at least one selected from the group consisting of an apnea check, a persistent flow limitation check, a slow breathing check, and a fast breathing check.

9. The method of claim 1 wherein at least one of the one or more abnormal breathing checks is based at least in part on the monitored respiration characteristic and the breathing cycle signal during two consecutive breathing cycles.

10. The method of claim 1 wherein d) further comprises at least one selected from the group consisting of an irregular breathing cycle check and an irregular inhalation period check.

11. The method of claim 1 wherein d) further comprises at least one selected from the group consisting of an apnea check, an irregular breathing cycle check, an irregular inhalation period check, a persistent flow limitation check, a slow breathing check, and a fast breathing check.

12. The method of claim 1, d) further comprising an apnea check, the apnea check comprising:
   f) monitoring the breathing cycle signal;
   g) operating a free running counter having a count value that changes over time;
   h) determining if the count value exceeds an apnea threshold;
   i) if the count value exceeds the apnea threshold, abnormal breathing is detected based on the apnea check; and
   j) resetting the count value of the free running counter each time the breathing cycle signal transitions from the second level to the first level.

13. The method of claim 1, d) further comprising an irregular breathing cycle check, the irregular breathing cycle check comprising:
   f) monitoring the breathing cycle signal;
   g) operating a system timer having a current timer value that changes over time;
   h) latching the current timer value in a first storage location each time the breathing cycle signal transitions from the second level to the first level to identify a start time for a current breathing cycle;
   i) determining a running breathing cycle time based at least in part on a difference between the start time and the current timer value;
   j) latching the running breathing cycle time in a second storage location each time the breathing cycle signal transitions from the second level to the first level to store a current breathing cycle time;
   k) latching the current breathing cycle time in a third storage location each time the breathing cycle signal transitions from the second level to the first level to store a previous breathing cycle time;
   l) determining a variance between consecutive breathing cycle times based at least in part on a difference between the previous breathing cycle time and the current breathing cycle time;
   m) determining if an absolute value of the variance exceeds an irregular breathing cycle threshold; and
   n) if the absolute value exceeds the irregular breathing cycle threshold, abnormal breathing is detected based on the irregular breathing cycle check.

14. The method of claim 1, d) further comprising an irregular inhalation period check, the irregular inhalation period check comprising:
   f) monitoring the breathing cycle signal;
   g) operating a system timer having a current timer value that changes over time;
   h) latching the current timer value in a first storage location each time the breathing cycle signal transitions from the second level to the first level to identify a start time for a current inhalation period;
   i) determining a running inhalation period time based at least in part on a difference between the start time and the current timer value;
   j) storing the running inhalation period time in a fourth storage location each time the breathing cycle signal transitions from the first level to the second level to store a current inhalation period time;
   k) storing the current inhalation period time in a fifth storage location each time the breathing cycle signal transitions from the first level to the second level to store a previous inhalation period time;
   l) determining a variance between consecutive inhalation period times based at least in part on a difference between the previous inhalation period time and the current inhalation period time;
   m) determining if an absolute value of the variance exceeds an irregular inhalation period threshold; and
   n) if the absolute value exceeds the irregular inhalation period threshold, abnormal breathing is detected based on the irregular inhalation period check.

15. The method of claim 1, d) further comprising a persistent flow limitation check, the persistent flow limitation check comprising:
   f) monitoring the breathing cycle signal;
   g) operating a system timer having a current timer value that changes over time;
   h) storing the current timer value in a first storage location each time the breathing cycle signal transitions from the second level to the first level to identify a start time for a current breathing cycle and a current inhalation period time;
   i) determining a running breathing cycle time based at least in part on a difference between the start time and the current timer value;
   j) storing the running breathing cycle time in a second storage location each time the breathing cycle signal transitions from the second level to the first level to store a current breathing cycle time;

k) determining a running inhalation period time based at least in part on a difference between the start time and the current timer value;

l) storing the running inhalation period time in a fourth storage location each time the breathing cycle signal transitions from the first level to the second level to store a current inhalation period time;

m) determining a ratio of the current inhalation period time to the current breathing cycle time;

n) determining if the ratio exceeds an persistent flow limitation threshold; and o) if the ratio exceeds the persistent flow limitation threshold, abnormal breathing is detected based on the persistent flow limitation check.

16. The method of claim 1, d) further comprising a slow breathing check, the slow breathing check comprising:

f) monitoring the breathing cycle signal;

g) operating a system timer having a current timer value that changes over time;

h) storing the current timer value in a first storage location each time the breathing cycle signal transitions from the second level to the first level to identify a start time for a current breathing cycle;

i) determining a running breathing cycle time based at least in part on a difference between the start time and the current timer value;

j) storing the running breathing cycle time in a second storage location each time the breathing cycle signal transitions from the second level to the first level to store a current breathing cycle time;

k) determining if the current breathing cycle time exceeds a maximum threshold; and l) if the current breathing cycle time exceeds the maximum threshold, abnormal breathing is detected based on the slow breathing check.

17. The method of claim 1, d) further comprising a fast breathing check, the fast breathing check comprising:

f) monitoring the breathing cycle signal;

g) operating a system timer having a current timer value that changes over time;

h) storing the current timer value in a first storage location each time the breathing cycle signal transitions from the second level to the first level to identify a start time for a current breathing cycle;

i) determining a running breathing cycle time based at least in part on a difference between the start time and the current timer value;

j) storing the running breathing cycle time in a second storage location each time the breathing cycle signal transitions from the second level to the first level to store a current breathing cycle time;

k) determining if the current breathing cycle time is less than a minimum threshold; and l) if the current breathing cycle time is less than the minimum threshold, abnormal breathing is detected based on the fast breathing check.

18. The method of claim 1, wherein the creating a triggered respiration signal further comprises:

detecting a positive surge based at least in part on a first transition of the filtered respiration signal in relation to a first predetermined threshold;

in response to detecting the positive surge, setting the triggered respiration signal to the first level;

detecting a negative surge based at least in part on a second transition of the filtered respiration signal in relation to a second predetermined threshold; and in response to detecting the negative surge, setting the triggered respiration signal to the second level.

19. The method of claim 18 wherein the first and second levels of the triggered respiration signal correspond to voltage levels associated with opposing digital signal logic levels.

20. The method of claim 1 wherein each incremental increasing or decreasing in e) is associated with transition of the breathing cycle signal from the second level to the first level.

21. The method of claim 1, wherein the creating the breathing cycle signal comprises a Schmitt trigger to produce the breathing cycle signal.

22. The method of claim 1, wherein the creating the triggered respiration signal comprises a Schmitt trigger to produce the triggered respiration signal.

23. A method for adjusting a desired pressure in a positive airway pressure device, the method comprising:

a) providing a breathing gas under positive pressure to a patient via a positive airway pressure device based at least in part on a current desired pressure;

b) monitoring a characteristic of the breathing gas, a characteristic of the patient, or a characteristic of the positive airway pressure device that is indicative of respiration;

c) creating a breathing cycle signal having a first level associated with inhalation and a second level different from the first level and associated with exhalation, the breathing cycle signal being based at least in part on the monitored respiration characteristic;

d) performing an abnormal breathing check based at least in part on the monitored respiration characteristic and the breathing cycle signal, wherein performing the abnormal breathing check comprises:

creating a processed respiration signal based at least in part on the monitored respiration characteristic;

monitoring the breathing cycle signal;

creating a triggered respiration signal with a first level associated with a positive surge and a second level different from the first level and associated with a negative surge, the triggered respiration signal being based at least in part on the processed respiration signal;

monitoring the triggered respiration signal;

incrementing a peak counter each time the triggered respiration signal transitions from the second level to the first level;

reading the peak counter each time the breathing cycle signal transitions from the first level to the second level;

comparing the peak counter to a threshold level; and based on the comparing, determining if abnormal breathing is detected; and e) if abnormal breathing is detected, increasing the current desired pressure by a first increment until a maximum desired pressure is reached, otherwise, decreasing the current desired pressure by a second increment until a minimum desired pressure is reached.

24. The method of claim 23, a) further comprising:

f) monitoring a characteristic of the breathing gas indicative of breathing gas pressure;

g) controlling a variable mechanism of the positive airway pressure device using a closed loop control process based at least in part on a difference between the current desired pressure and the monitored pressure characteristic to reduce the difference;

h) determining if a runaway low pressure condition exists; and i) if a runaway low pressure condition is detected, setting the current desired pressure to a desired startup pressure.

25. The method of claim 23, wherein the first and second levels of the triggered respiration signal correspond to voltage levels associated with opposing digital signal logic levels.

26. The method of claim 23, wherein the processed respiration signal is based at least in part on bandpass filtering the monitored respiration characteristic.

27. The method of claim 23, wherein the processed respiration signal is based at least in part on differentiating the monitored respiration characteristic.

28. The method of claim 23, wherein the creating the breathing cycle signal comprises a Schmitt trigger to produce the breathing cycle signal.

29. The method of claim 23, wherein the creating the triggered respiration signal comprises a Schmitt trigger to produce the triggered respiration signal.

30. An apparatus for adjusting a desired pressure in a positive airway pressure device, the apparatus comprising:

a breathing gas flow path in operative communication with a closed loop control logic, the breathing gas flow path and closed loop control logic being adapted to provide a breathing gas under positive pressure to a patient based at least in part on a current desired pressure;

a respiration characteristic monitoring logic in operative communication with the breathing gas flow path to monitor a characteristic of the breathing gas, a characteristic of the patient, or a characteristic of the apparatus that is indicative of respiration;

a breathing cycle signal logic in operative communication with the respiration characteristic monitoring logic to create a breathing cycle signal having a first level associated with inhalation and a second level different from the first level and associated with exhalation, the breathing cycle signal being based at least in part on the monitored respiration characteristic;

an abnormal breathing check logic in operative communication with at least one of the breathing cycle signal logic and the respiration characteristic monitoring logic to perform an abnormal breathing check based at least in part on the monitored respiration characteristic and the breathing cycle signal, wherein the abnormal breathing check logic comprises:

logic for creating a processed respiration signal based at least in part on the monitored respiration characteristic;

logic for monitoring the breathing cycle signal;

logic for creating a triggered respiration signal with a first level associated with a positive surge and a second level different from the first level and associated with a negative surge, the triggered respiration signal being based at least in part on the processed respiration signal;

logic for monitoring the triggered respiration signal;

logic for incrementing a first counter based on a transition of the triggered respiration signal from the second level to the first level to count a rising edge;

logic for incrementing a second counter based on a transition of the triggered respiration signal from the first level to the second level to count a falling edge;

logic for reading the first counter and the second counter each time the breathing cycle signal transitions from the first level to the second level;

logic for comparing the first counter and second counter to one or more threshold levels; and based on the comparing, logic for determining if abnormal breathing is detected; and a desired pressure adjustment logic in operative communication with the abnormal breathing check logic, breathing cycle signal logic, and closed loop control logic to increase the current desired pressure by a first increment until a maximum desired pressure is reached, if abnormal breathing is detected and to decrease the current desired pressure by a second increment until a minimum desired pressure is reached if abnormal breathing is not detected.

31. The apparatus of claim 30, wherein the first and second levels of the triggered respiration signal correspond to voltage levels associated with opposing digital signal logic levels.

32. The apparatus of claim 30, wherein the logic for creating a processed respiration signal comprises a bandpass filter.

33. The apparatus of claim 30, wherein the logic for creating a processed respiration signal comprises a differentiator.

34. The apparatus of claim 30, wherein the logic for incrementing the first counter comprises logic for incrementing during each transition of the triggered respiration signal from the second level to the first level.

35. The apparatus of claim 30, wherein the breathing cycle signal logic comprises a Schmitt trigger to create the breathing cycle signal.

36. The apparatus of claim 30, wherein the abnormal breathing check logic comprises a Schmitt trigger to create the triggered respiration signal.

37. A method for adjusting a desired pressure in a positive airway pressure device, the method comprising:

a) providing a breathing gas under positive pressure to a patient via a positive airway pressure device based at least in part on a current desired pressure;

b) monitoring a characteristic of the breathing gas that is indicative of respiration;

c) creating a breathing cycle signal with a first level associated with inhalation and a second level different from the first level and associated with exhalation, the breathing cycle signal being based at least in part on the monitored respiration characteristic;

d) performing one or more abnormal breathing checks based at least in part on the monitored respiration characteristic and the breathing cycle signal, wherein one or more abnormal breathing checks comprises a hypopnea check, the hypopnea check comprising:

creating a processed respiration signal based at least in part on the monitored respiration characteristic;

monitoring the breathing cycle signal;

creating a triggered respiration signal with a first level associated with a positive surge and a second level different from the first level and associated with a negative surge, the triggered respiration signal being based at least in part on the processed respiration signal;

monitoring the triggered respiration signal;

incrementing a first counter based on a transition of the triggered respiration signal from the second level to the first level to count a rising edge;

incrementing a second counter based on a transition of the triggered respiration signal from the first level to the second level to count a falling edge;

reading the first counter and the second counter each time the breathing cycle signal transitions from the first level to the second level;

comparing the first counter and second counter to one or more threshold levels; and based on the comparing, determining if abnormal breathing is detected based on the hypopnea check; and e) if abnormal breathing is detected, increasing the current desired pressure by a first increment until a maximum desired pressure is reached, otherwise, decreasing the current desired pressure by a second increment until a minimum desired pressure is reached.

38. The method of claim 37 wherein the first and second levels of the triggered respiration signal correspond to voltage levels associated with opposing digital signal logic levels.

39. The method of claim 37, wherein the processed respiration signal is based at least in part on bandpass filtering the monitored respiration characteristic.

40. The method of claim 37, wherein the processed respiration signal is based at least in part on differentiating the monitored respiration characteristic.

41. The method of claim 37, wherein the first counter is incremented during each transition of the triggered respiration signal from the second level to the first level.

42. The method of claim 37, wherein the creating the breathing cycle signal comprises a Schmitt trigger to produce the breathing cycle signal.

43. The method of claim 37, wherein the creating the triggered respiration signal comprises a Schmitt trigger to produce the triggered respiration signal.

* * * * *